United States Patent
Stachel et al.

(10) Patent No.: US 9,458,181 B2
(45) Date of Patent: Oct. 4, 2016

(54) CATHEPSIN CYSTEINE PROTEASE INHIBITORS

(71) Applicant: Merck Sharp & Dohme Corp., Rahway, NJ (US)

(72) Inventors: Shawn Stachel, Perkasie, PA (US); Daniel V. Paone, Lansdale, PA (US); Jing Li, Lansdale, PA (US); Kausik Nanda, Norristown, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 14/506,760

(22) Filed: Oct. 6, 2014

(65) Prior Publication Data

US 2015/0099719 A1    Apr. 9, 2015

Related U.S. Application Data

(60) Provisional application No. 61/888,029, filed on Oct. 8, 2013.

(51) Int. Cl.

| | | |
|---|---|---|
| *A61K 31/421* | (2006.01) | |
| *C07D 263/32* | (2006.01) | |
| *C07D 263/34* | (2006.01) | |
| *C07D 277/30* | (2006.01) | |
| *C07D 413/04* | (2006.01) | |
| *C07D 413/10* | (2006.01) | |
| *C07D 417/10* | (2006.01) | |
| *C07D 417/14* | (2006.01) | |
| *C07D 495/08* | (2006.01) | |
| *C07F 7/08* | (2006.01) | |
| *A61K 31/695* | (2006.01) | |
| *A61K 31/422* | (2006.01) | |
| *A61K 31/547* | (2006.01) | |
| *A61K 31/541* | (2006.01) | |
| *A61K 31/5377* | (2006.01) | |
| *A61K 31/496* | (2006.01) | |
| *C07D 513/08* | (2006.01) | |
| *A61K 31/427* | (2006.01) | |
| *A61K 45/06* | (2006.01) | |
| *C07D 413/12* | (2006.01) | |

(52) U.S. Cl.

CPC .......... *C07F 7/0807* (2013.01); *A61K 31/421* (2013.01); *A61K 31/422* (2013.01); *A61K 31/427* (2013.01); *A61K 31/496* (2013.01); *A61K 31/5377* (2013.01); *A61K 31/541* (2013.01); *A61K 31/547* (2013.01); *A61K 31/695* (2013.01); *A61K 45/06* (2013.01); *C07D 263/32* (2013.01); *C07D 263/34* (2013.01); *C07D 277/30* (2013.01); *C07D 413/04* (2013.01); *C07D 413/10* (2013.01); *C07D 413/12* (2013.01); *C07D 417/10* (2013.01); *C07D 417/14* (2013.01); *C07D 495/08* (2013.01); *C07D 513/08* (2013.01)

(58) Field of Classification Search
None
See application file for complete search history.

(56) References Cited

FOREIGN PATENT DOCUMENTS

| WO | 2005000800 | 1/2005 |
|---|---|---|
| WO | WO2007003056 A1 | 1/2007 |

OTHER PUBLICATIONS

International Search Report for PCT/US2014/059215 mailed Nov. 27, 2014, 12 pages.
Robichaud, J. et al., "B-Substituted cyclohexanecarboxamide cathepsin K inhibitors: Modification of the 1,2-disubstituted aromatic core," Bioorganic & Medicinal Chemistry Letters, 2007, 3146-3151.

*Primary Examiner* — Nyeemah A Grazier

(74) *Attorney, Agent, or Firm* — Nicole M. Beeler; Catherine D. Fitch

(57) ABSTRACT

This invention relates to a novel class of compounds which are cysteine protease inhibitors, including but not limited to, inhibitors of cathepsins K, L, S and B. These compounds are useful for treating diseases in which inhibition of bone resorption is indicated, such as osteoporosis.

15 Claims, No Drawings

CATHEPSIN CYSTEINE PROTEASE INHIBITORS

BACKGROUND OF THE INVENTION

A variety of disorders in humans and other mammals involve or are associated with abnormal bone resorption. Such disorders include, but are not limited to, osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, hypercalcemia of malignancy or multiple myeloma. One of the most common of these disorders is osteoporosis, which in its most frequent manifestation occurs in postmenopausal women. Osteoporosis is a systemic skeletal disease characterized by a low bone mass and microarchitectural deterioration of bone tissue, with a consequent increase in bone fragility and susceptibility to fracture. Osteoporotic fractures are a major cause of morbidity and mortality in the elderly population. As many as 50% of women and a third of men will experience an osteoporotic fracture. A large segment of the older population already has low bone density and a high risk of fractures. There is a significant need to both prevent and treat osteoporosis and other conditions associated with bone resorption. Because osteoporosis, as well as other disorders associated with bone loss, are generally chronic conditions, it is believed that appropriate therapy will typically require chronic treatment.

Cathepsins belong to the papain superfamily of cysteine proteases. These proteases function in the normal physiological as well as pathological degradation of connective tissue. Cathepsins play a major role in intracellular protein degradation and turnover and remodeling. To date, a number of cathepsin have been identified and sequenced from a number of sources. These cathepsins are naturally found in a wide variety of tissues. For example, cathepsin B, C, F, H, L, K, O, S, V, W, and Z have been cloned. Cathepsin L is implicated in normal lysosomal proteolysis as well as several diseases states, including, but not limited to, metastasis of melanomas. Cathepsin S is implicated in Alzheimer's disease, atherosclerosis, chronic obstructive pulmonary disease and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. Increased Cathepsin B levels and redistribution of the enzyme are found in tumors, suggesting a role in tumor invasion and metastasis. In addition, aberrant Cathepsin B activity is implicated in such disease states as rheumatoid arthritis, osteoarthritis, pneumocystisis *carinii*, acute pancreatitis, inflammatory airway disease and bone and joint disorders.

Mammalian cathepsins are related to the papain-like cysteine proteases expressed by disease-causing parasites including those from the families protozoa, platyhelminthes, nematodes and arthropodes. These cysteine proteases play an essential role in the life cycle of these organisms.

Human type I collagen, the major collagen in bone is a good substrate for cathepsin K. See Kafienah, W., et al., 1998, *Biochem J* 331:727-732, which is hereby incorporated by reference in its entirety. In vitro experiments using antisense oligonucleotides to cathepsin K, have shown diminished bone resorption in vitro, which is probably due to a reduction in translation of cathepsin K mRNA. See Inui, T., et al., 1997, *J Biol Chem* 272:8109-8112, which is hereby incorporated by reference in its entirety. The crystal structure of cathepsin K has been resolved. See McGrath, M. E., et al., 1997, *Nat Struct Biol* 4:105-109; Zhao, B., et al., 1997, *Nat Struct Biol* 4: 109-11, which are hereby incorporated by reference in their entirety. Also, selective peptide based inhibitors of cathepsin K have been developed See Bromme, D., et al., 1996, *Biochem J* 315:85-89; Thompson, S. K., et al., 1997, *Proc Natl Acad Sci USA* 94:14249-14254, which are hereby incorporated by reference in their entirety. Accordingly, inhibitors of Cathepsin K can reduce bone resorption. Such inhibitors would be useful in treating disorders involving bone resorption, such as osteoporosis.

What is needed in the art are therapeutic agents to treat diseases associated with Cathepsin K activity including osteoporosis, glucocorticoid induced osteoporosis, Paget's disease, abnormally increased bone turnover, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma.

SUMMARY OF THE INVENTION

The present invention relates to compounds that may be capable of treating and/or preventing cathepsin dependent conditions or disease states in a mammal in need thereof. One embodiment of the present invention is illustrated by a compound of Formula I, and the pharmaceutically acceptable salts, stereoisomers and N-oxide derivatives thereof:

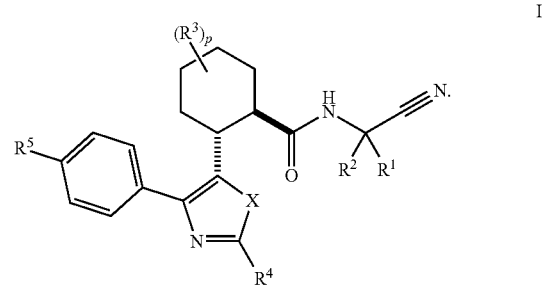

The compounds of Formula I are inhibitors of Cathepsin K. As a result, the compounds of Formula I could be useful for methods of treating, inhibiting or amelioration of one or more disease states that could benefit from inhibition of Cathepsin K, including osteoporosis. The compounds of this invention could further be used in combination with other therapeutically effective agents, including but not limited to, other drugs useful for the treatment of osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy or multiple myeloma. The invention furthermore relates to processes for preparing compounds of Formula I, and pharmaceutical compositions which comprise compounds of Formula I.

DETAILED DESCRIPTION OF THE INVENTION

The present invention relates to compounds of the following chemical formula:

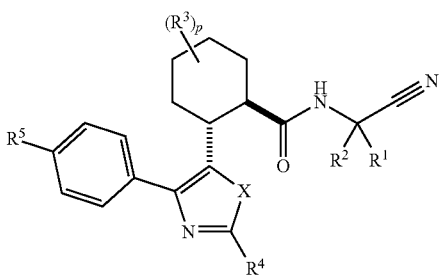

wherein X is oxygen, sulfur, or nitrogen;
$R^1$ is hydrogen, $C_{1-6}$ alkyl, $C_{2-6}$ alkenyl, $C_{3-8}$ cycloalkyl or heterocyclyl, wherein said alkyl and alkenyl groups are optionally substituted with $C_{3-6}$ cycloalkyl, one to six halo, hydroxy or $R^8$; and wherein said cycloalkyl and heterocyclyl groups are optionally substituted with one or two substituents selected from the group consisting of $C_{1-6}$ alkyl, halo, $OR^6$ and keto;
$R^2$ is hydrogen, $C_{1-6}$ alkyl or $C_{2-6}$ alkenyl wherein said alkyl and alkenyl groups are optionally substituted with $C_{3-6}$ cycloalkyl, one to six halo or $R^8$;
or $R^1$ and $R^2$ can be taken together with the carbon atom to which they are attached to form a $C_{3-8}$ cycloalkyl or heterocyclyl ring wherein said cycloalkyl and heterocyclyl rings are optionally substituted with one or two substituents independently selected from the group consisting of $R^6$, $C_{1-6}$ haloalkyl and halo;
Each $R^3$ is independently selected from the group consisting of hydrogen, halo and $C_{1-2}$ alkyl, wherein said alkyl group is optionally substituted with one to three halo; or
two $R^3$ groups can be taken together with the carbon atom to which they are attached to form a $C_{3-4}$ cycloalkyl ring, wherein said ring is optionally substituted with one to three halo;
$R^4$ is hydrogen, $C_{1-6}$ alkyl, $C_{2-6}$ alkenyl, $C_{2-3}$ alkynyl, $NR^6R^7$, $OR^6$, $OR^8$ or $R^8$ wherein said alkyl groups are optionally substituted with one to six substituents independently selected from the group consisting of $OR^7$, halo, hydroxy, cyano and $R^8$;
$R^5$ is hydrogen, $C_{1-6}$ alkyl, $C_{2-6}$ alkenyl, aryl, heteroaryl, $C_{3-8}$ cycloalkyl, heterocyclyl, $C(O)NR^6R^8$, $C(O)R^8$, $NR^6C(O)OR^7$ or $SO_mR^6$, wherein said aryl, heteroaryl, $C_{3-8}$ cycloalkyl and heterocyclyl groups are optionally substituted with one to five substituents independently selected from the group consisting of $C_{1-6}$ alkyl, halo, oxo, cyano, $C_{1-6}$ haloalkyl and $SO_mR^6$; $R^6$ is hydrogen or $C_{1-6}$ alkyl which is optionally substituted with one to three substituents independently selected from the group consisting of halo, hydroxy, cyano and $O(C_{1-6}$ alkyl);
$R^7$ is hydrogen or $C_{1-6}$ alkyl which is optionally substituted with one to three substituents independently selected from the group consisting of halo, hydroxy, cyano and $O(C_{1-6}$ alkyl);
$R^8$ is $C_{3-8}$ cycloalkyl, aryl, heteroaryl or heterocyclyl, wherein said cycloalkyl, aryl, heteroaryl and heterocyclyl groups are optionally substituted with one to four substituents independently selected from the group consisting of halo, cyano, oxo, $C_{1-6}$ haloalkyl, $R^6$, $OR^6$, $C_{3-6}$ cycloalkyl, aryl, heteroaryl, heterocyclyl, $SO_mR^6$ and $SF_5$;
m is an integer from zero to two;
p is an integer from zero to two.

In an embodiment of the invention, X is oxygen. In another embodiment of the invention, X is sulfur. In another embodiment of the invention, X is or nitrogen.

In an embodiment of the invention, $R^1$ is hydrogen, $C_{1-3}$ alkyl, $C_{3-8}$ cycloalkyl or heterocyclyl, wherein said alkyl group is optionally substituted with one to six halo or hydroxy. In a class of the invention, $R^1$ is hydrogen, $C_{1-3}$ alkyl, $C_{3-8}$ cycloalkyl or heterocyclyl, wherein said alkyl group is optionally substituted with one to six halo. In a class of the invention, $R^1$ is hydrogen. In another class of the invention, $R^1$ is methyl. In another class of the invention, $R^1$ is ethyl. In another class of the invention, $R^1$ is isopropyl. In another class of the invention, $R^1$ is heterocyclyl. In another class of the invention $R^1$ is tetrahydropyranyl.

In an embodiment of the invention, $R^2$ is hydrogen or $C_{1-3}$ alkyl, wherein said alkyl group is optionally substituted with one to six halo. In a class of the invention, $R^2$ is hydrogen. In another class of the invention, $R^2$ is methyl.

In an embodiment of the invention, $R^1$ and $R^2$ can be taken together with the carbon atom to which they are attached to form a $C_{3-6}$ cycloalkyl ring, which is optionally substituted with one or two $R^6$. In a class of the invention, $R^1$ and $R^2$ can be taken together with the carbon atom to which they are attached to form a cyclopropyl ring. In another class of the invention, $R^1$ and $R^2$ can be taken together with the carbon atom to which they are attached to form a cyclopropyl ring which is substituted with two methyl groups.

In an embodiment of the invention, each $R^3$ is independently selected from the group consisting of hydrogen or halo, or two $R^3$ groups can be taken together with the carbon atom to which they are attached to form a $C_{3-4}$ cycloalkyl ring, wherein said ring is optionally substituted with one to three halo. In a class of the invention, $R^3$ is hydrogen. In a class of the invention, $R^3$ is halo. In a subclass of the invention, $R^3$ is fluoro. In a class of the invention, two $R^3$ groups can be taken together with the carbon atom to which they are attached to form a cyclopropyl ring.

In an embodiment of the invention, $R^4$ is hydrogen, $C_{1-6}$ alkyl, $OR^6$ or $R^8$, wherein said alkyl groups are optionally substituted with one to six substituents independently selected from the group consisting of $OR^7$, halo, hydroxy, cyano and $R^8$. In a class of the invention, $R^4$ is hydrogen. In a class of the invention, $R^4$ is $C_{1-6}$ alkyl. In a class of the invention, $R^4$ is $OR^6$. In a class of the invention, $R^4$ is $R^8$. In a subclass of the invention, $R^4$ is aryl, which is optionally substituted with one to three substituents independently selected from the group consisting of halo, methyl, ethyl, cyano or $SO_2CH_3$. In a further subclass of the invention, $R^4$ is phenyl, which is optionally substituted with halo.

In an embodiment of the invention, $R^5$ is heteroaryl, heterocyclyl, $C(O)NR^6R^8$, $C(O)R^8$ or $NR^6C(O)OR^7$, wherein said heteroaryl and heterocyclyl groups are optionally substituted with one to five substituents independently selected from the group consisting of $C_{1-6}$ alkyl, halo, oxo, cyano, $C_{1-6}$haloalkyl and $SO_mR^6$. In a class of the invention, $R^5$ is heterocyclyl or $C(O)R^8$. In a class of the invention, $R^5$ is heterocyclyl, which is optionally substituted with one to five substituents independently selected from the group consisting of $C_{1-6}$ alkyl, halo, oxo, cyano, $C_{1-6}$haloalkyl and $SO_mR^6$. In a subclass of the invention, $R^5$ is 1,1-dioxidothiomorphonlinyl.

In an embodiment of the invention, $R^6$ is hydrogen. In another embodiment of the invention, $R^6$ is $C_{1-6}$ alkyl which is optionally substituted with one to three substituents independently selected from the group consisting of halo, hydroxy, cyano and $O(C_{1-6}$ alkyl). In a class of the invention, $R^6$ is methyl. In another class of the invention, $R^6$ is trifluoromethyl.

In an embodiment of the invention, m is two. In another embodiment of the invention, m is one.

In an embodiment of the invention, p is zero. In another embodiment of the invention, p is one. In another embodiment of the invention, p is two.

Reference to the preferred classes and subclasses set forth above is meant to include all combinations of particular and preferred groups unless stated otherwise.

Specific embodiments of the present invention include, but are not limited to the compounds identified herein as Examples 1 to 159, or pharmaceutically acceptable salts thereof Also included within the scope of the present invention is a pharmaceutical composition which is comprised of a compound of Formula I as described above and a pharmaceutically acceptable carrier. The invention is also contemplated to encompass a pharmaceutical composition which is comprised of a pharmaceutically acceptable carrier and any of the compounds specifically disclosed in the present application. These and other aspects of the invention will be apparent from the teachings contained herein.

Utilities

The compounds of the present invention are inhibitors of cathepsins and may be useful to treat or prevent cathepsin dependent diseases or conditions in mammals, preferably humans. Specifically, the compounds of the present invention are inhibitors of Cathepsin K and may be useful to treat or prevent Cathepsin K dependent diseases or conditions in mammals, preferably humans.

The compounds of the present invention have advantages over structurally similar compounds known in the art in that they have a marked improved selectivity profiles toward related cathepsins, especially cathepsin F.

"Cathepsin dependent diseases or conditions" refers to pathologic conditions that depend on the activity of one or more cathepsins. "Cathepsin K dependent diseases or conditions" refers to pathologic conditions that depend on the activity of Cathepsin K. Diseases associated with Cathepsin K activities include osteoporosis, glucocorticoid induced osteoporosis, Paget's disease, abnormally increased bone turnover, tooth loss, bone fractures, rheumatoid arthritis, osteoarthritis, periprosthetic osteolysis, osteogenesis imperfecta, atherosclerosis, obesity, glaucoma, chronic obstructive pulmonary disease and cancer including metastatic bone disease, hypercalcemia of malignancy, and multiple myeloma. In treating such conditions with the instantly claimed compounds, the required therapeutic amount will vary according to the specific disease and is readily ascertainable by those skilled in the art. Although both treatment and prevention are contemplated by the scope of the invention, the treatment of these conditions is the preferred use.

An embodiment of the invention is a method of inhibiting cathepsin activity in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of treating or preventing cathepsin dependent conditions in a mammal in need thereof, comprising administering to the mammal a therapeutically effective amount of any of the compounds or any of the pharmaceutical compositions described above.

A class of the embodiment is the method wherein the cathepsin activity is cathepsin K activity.

Another embodiment of the invention is a method of inhibiting bone loss in a mammal in need thereof, comprising administering to the mammal a therapeutically effective amount of any of the compounds or any of the pharmaceutical compositions described above. Another embodiment of the invention is a method of reducing bone loss in a mammal in need thereof, comprising administering to the mammal a therapeutically effective amount of any of the compounds or any of the pharmaceutical compositions described above. The utility of cathepsin K inhibitors in the inhibition of bone resorption, which includes abnormally increased bone turnover, bone fractures, Paget's disease, osteogenesis imperfecta and periprosthetic osteolysis, is known in the literature, see Stroup, G. B., Lark, M. W., Veber, D F., Bhattacharrya, A., Blake, S., Dare, L. C., Erhard, K. F., Hoffman, S. J., James, I. E., Marquis, R. w., Ru, Y., Vasko-Moser, J. A., Smith, B. R., Tomaszek, T. and Gowen, M. Potent and selective inhibition of human cathepsin K leads to inhibition of bone resorption in vivo in a nonhuman primate. J. Bone Miner. Res., 16:1739-1746; 2001; and Votta, B. J., Levy, M. A., Badger, A., Dodds, R. A., James, I. E., Thompson, S., Bossard, M. J., Carr, T., Connor, J. R., Tomaszek, T. A., Szewczuk, L., Drake, F. H., Veber, D., and Gowen, M. Peptide aldehyde inhibitors of cathepsin K inhibit bone resorption both in vivo and in vitro. J. Bone Miner. Res. 12:1396-1406; 1997.

Another embodiment of the invention is a method of treating or preventing osteoporosis, including glucocorticoid induced osteoporosis, in a mammal in need thereof, comprising administering to the mammal a therapeutically effective amount of any of the compounds or any of the above pharmaceutical compositions described above. The utility of cathepsin K inhibitors in the treatment or prevention of osteoporosis is known in the literature, see Saftig, P., Hunziker, E., Wehmeyer, O., Jones, S., Boyde, A., Rommerskirch, W., Moritz, J. D., Schu, P., and Vonfigura, K. Impaired osteoclast bone resorption leads to osteopetrosis in cathepsin K-deficient mice. Proc. Natl. Acad. Sci. USA 95:13453-13458; 1998.

Another embodiment of the invention is a method of treating or preventing periodontal disease, including tooth loss, in a mammal in need thereof, comprising administering to the mammal a therapeutically effective amount of any of the compounds or any of the above pharmaceutical compositions described above. The utility of cathepsin K inhibitors in the treatment or prevention of periodontal disease and tooth loss is known in the literature, see Tsuji Y, et al., Expression of cathepsin K mRNA and protein in odontoclasts after experimental tooth movement in the mouse maxilla by in situ hybridization and immunoelectron microscopy. Cell Tissue Res. 2001 March; 303(3):359-69.

Another embodiment of the invention is a method of treating or preventing rheumatoid arthritic condition in a mammal in need thereof, comprising administering to the mammal a therapeutically effective amount of any of the compounds or any of the pharmaceutical compositions described above. It is known in the literature that progressive destruction of the periarticular bone is a major cause of joint dysfunction and disability in patients with rheumatoid arthritis (RA), see Goldring S R, "Pathogenesis of bone erosions in rheumatoid arthritis". Curr. Opin. Rheumatol. 2002; 14:

406-10. Analysis of joint tissues from patients with RA have provided evidence that cathepsin K positive osteoclasts are the cell types that mediate the focal bone resorption associated with rheumatoid synovial lesion, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74. In addition, generalized bone loss is a major cause of morbidity associated with severe RA. The frequency of hip and spinal fractures is substantially increased in patients with chronic RA, see Gould A, Sambrook, P, Devlin J et al, "Osteoclastic activation is the principal mechanism leading to secondary osteoporosis in rheumatoid arthritis". J. Rheumatol. 1998; 25: 1282-9. The utility of cathepsin K inhibitors in the treatment or prevention of resorption in subarticular bone and of generalized bone loss represent a rational approach for pharmacological intervention on the progression of rheumatoid arthritis.

Another embodiment of the invention is a method of treating or preventing the progression of osteoarthritis in a mammal in need thereof, comprising administering to the mammal a therapeutically effective amount of any of the compounds or any of the pharmaceutical compositions described above. It is known in the literature that osteoarthritis (OA) is accompanied with well-defined changes in the joints, including erosion of the articular cartilage surface, peri-articular endochondral ossification/osteophytosis, and subchondral bony sclerosis and cyst formation, see Oettmeier R, Abendroth, K, "Osteoarthritis and bone: osteologic types of osteoarthritis of the hip", Skeletal Radiol. 1989; 18: 165-74. Recently, the potential contribution of subchondral bone sclerosis to the initiation and progression of OA have been suggested. Stiffened subchondral bone as the joint responding to repetitive impulsive loading, is less able to attenuate and distribute forces through the joint, subjecting it to greater mechanical stress across the articular cartilage surface. This in turn accelerates cartilage wear and fibrillate, see Radin, E L and Rose R M, "Role of subchondral bone in the initiation and progression of cartilage damage", Clin. Orthop. 1986; 213: 34-40. Inhibition of excessive subarticular bone resorption by an anti-resorptive agent such as a cathepsin K inhibitor, will lead to inhibition of subchondral bone turnover, thus may have a favorable impact on OA progression.

In addition to the above hypothesis, cathepsin K protein expression was recently identified in synovial fibroblasts, macrophage-like cells, and chondrocytes from synovium and articular cartilage specimens derived from OA patients, see Hou, W-S, Li, W, Keyszer, G, Weber, E, Levy, R, Klein, M J, Gravallese, E M, Goldring, S R, Bromme, D, "Comparison of Cathepsin K and S expression within the Rheumatoid and Osteoarthritic Synovium", Arthritis Rheumatism 2002; 46: 663-74; and Dodd, R A, Connor, J R, Drake, F H, Gowen, M, "Expression of Cathepsin K messenger RNA in giant cells and their precursors in human osteoarthritic synovial tissues". Arthritis Rheumatism 1999; 42: 1588-93; and Konttinen, Y T, Mandelin, J, Li, T-F, Salo, J, Lassus, J et al. "Acidic cysteine endoproteinase cathepsin K in the degeneration of the superficial articular hyaline cartilage in osteoarthritis", Arthritis Rheumatism 2002; 46: 953-60. These recent studies thus implicated the role of cathepsin K in the destruction of collagen type II in the articular cartilage associated with the progression of osteoarthritis. The utility of cathepsin K inhibitors in the treatment or prevention of osteoarthritis as described in this invention thus comprise of two different mechanisms, one is on the inhibition of osteoclast-driven subchondral bone turnover, and two is on the direct inhibition of collagen type II degeneration in the synovium and cartilage of patients with OA.

Another embodiment of the invention is a method of treating cancer in a mammal in need thereof, comprising administering to the mammal a therapeutically effective amount of any of the compounds or any of the pharmaceutical compositions described above. It is known in the literature that cathepsin K is expressed in human breast carcinoma, prostate cancer and chordoma and has matrix degrading capabilities, see Littlewood-Evans A J, Bilbe G, Bowler W B, Farley D, Wlodarski B, Kokubo T, Inaoka T, Sloane J, Evans D B, Gallagher J A, "The osteoclast-associated protease cathepsin K is expressed in human breast carcinoma." Cancer Res 1997 Dec. 1; 57(23):5386-90, Brubaker K D, Vessella R L, True L D, Thomas R, Corey E "Cathepsin K mRNA and protein expression in prostate cancer progression." J Bone Miner Res 2003 18, 222-30, Haeckel C, Krueger S, Kuester D, Ostertag H, Samii M, Buehling F, Broemme D, Czerniak B, Roessner A. "Expression of cathepsin K in chordoma." Hum Pathol 2000 July; 31(7):834-40.

Another embodiment of the invention is a method of treating atherosclerosis in a mammal in need thereof, comprising administering to the mammal a therapeutically effective amount of any of the compounds or any of the pharmaceutical compositions described above. It is known in the literature that cathepsin K is expressed in human atheroma and has significant elastase activity, see Sukhova G K, Shi G P, Simon D I, Chapman H A, Libby P. "Expression of the elastolytic cathepsins S and K in human atheroma and regulation of their production in smooth muscle cells." J Clin Invest 1998 August 102, 576-83. It is also known that the Cat K null mouse when crossed with an ApoE null mouse shows reduced atherosclerotic plaque area and increased resistance to plaque rupture, see E. Lutgens, S. P. M. Lutgens, B. C. G. Faber, S. Heeneman, M. M. J. Gijbels, M. P. J. de Winther, P. Frederik, I. van der Made, D. Black, M. J. A. P. Daemen, K. B. J. M. Cleutjens "Disruption of the Cathepsin K Gene Reduces Atherosclerosis Progression and Induces Plaque Fibrosis but Accelerates Macrophage Foam Cell Formation." Circulation 2006 113:98-107. Increased plaque stability would lead to a decrease in heart attack and stroke in a patient administered a therapeutically effective amound of any of the compounds or any of the pharmaceutical compositions described above.

Another embodiment of the invention is a method of treating obesity in a mammal in need thereof, comprising administering to the mammal a therapeutically effective amount of any of the compounds or any of the pharmaceutical compositions described above. It is known in the literature that cathepsin K mRNA is increased in adipose tissue in several mouse models of obesity and also in adipose tissue of obese human males, see Chiellini C, Costa M, Novelli S E, Amri E Z, Benzi L, Bertacca A, Cohen P, Del Prato S, Friedman J M, Maffei M. "Identification of cathepsin K as a novel marker of adiposity in white adipose tissue," J Cell Physiol 2003, 195, 309-21.

Another embodiment of the invention is a method of treating glaucoma in a mammal in need thereof, comprising administering to the mammal a therapeutically effective amound of any of the compounds or any of the pharmaceutical compositions described above. Cathepsin K is highly expressed in the iris, ciliary body and retinal pigment epithelium, and as such can be useful in the treatment of glaucoma, see Ortega, J., et al., "Gene Expression of Proteases and Protease Inhibitors in the Human Ciliary Epithelium and ODM-2 cells," Exp. Eye Res (1997) 65, 289-299; International Publication WO 2004/058238 (Alcon, Inc.).

Another embodiment of the invention is a method of treating chronic obstructive pulmonary disease in a mammal in need thereof, comprising administering to the mammal a therapeutically effective amount of any of the compounds or any of the pharmaceutical compositions described above. It is known in the literature that cathepsin K plays a role in lung fibrosis, see Buhling, F., et al., "Pivotal role of cathepsin K in lung fibrosis," Am J Pathol. 2004 June; 164(6): 2203-16.

Another embodiment of the invention is a method of treating parasitic infections in a mammal in need thereof, comprising administering to the mammal a therapeutically effective amount of any of the compounds or any of the pharmaceutical compositions described above. It is known in the literature that mammalian cathepsins are related to the papain-like cysteine proteases which play an important role in the life cycle of these parasites. Such parasites are involved in the diseases of malaria, American trypanosomiasis, African trypanosomiasis, leishmaniasis, giardiasis, trichomoniasis, amoebiasis, schistosomiasis, fascioliasis, paragonimiasis and intestinal roundworms, see Lecaille F, Kaleta J, Bromme D., Human and parasitic papain-like cysteine proteases: their role in physiology and pathology and recent developments in inhibitor design. Chem Rev 2002 102, 4459-88.

Another embodiment of the invention is a method of treating severe acute respiratory syndrome (SARS) in a mammal in need thereof, comprising administering to the mammal a therapeutically effective amount of any of the compounds or any of the pharmaceutical compositions described above.

Another embodiment of the invention is a method of treating metastatic bone disease in a mammal in need thereof, comprising administering to the mammal a therapeutically effective amount of any of the compounds or any of the pharmaceutical compositions described above. It is known in the literature that osteoclasts are responsible for bone resorption and that bone destruction and hypercalcemia induced by metastatic tumors are carried out by osteoclasts. Accordingly, the inhibition of osteoclasts can prevent bone destruction and bone metastasis, see Miyamoto, T. and Suda, T., "Differentiation and function of osteoclasts," Keio J Med 2003 March; 52(1):1-7.

Another embodiment of the invention is a method of preventing metastatic bone disease in a mammal with a primary tumor that carries a risk of bone metastasis, comprising administering to the mammal a therapeutically effective amount of any of the compounds or any of the pharmaceutical compositions described above. It is described in the literature that compounds that inhibit osteoclasts function can prevent tumor cell adhesion to bone, see S. Boissier, M. Ferreras, O. Peyruchaud, S. Magnetto, F. H. Ebetino, M. Colombel, P. Delmas, J.-M. Delaissé and P. Clézardin "Bisphosphonates Inhibit Breast and Prostate Carcinoma Cell Invasion, an Early Event in the Formation of Bone Metastases" *Cancer Research* 60, 2949-2954, 2000

Another embodiment of the invention is a method of treating hypercalcemia of malignancy or multiple myeloma in a mammal in need thereof, comprising administering to the mammal a therapeutically effective amount of any of the compounds or any of the pharmaceutical compositions described above. It is known in the literature that cathepsin K plays a role in hypercalcemia of malignancy and multiple myeloma, see Faust, J. et al., Multiple myeloma cells and cells of the human osteoclast lineage share morphological and cell surface markers. J Cell Biochem. 1998 Dec. 15; 71(4):559-68; A. lipton, New therapeutic agents for the treatment of bone diseases. Expert Opin Biol Ther. 2005 June; 5(6):817-32.

Another embodiment of the invention is administering to a mammal a therapeutically effective amount of any of the compounds or any of the pharmaceutical compositions described above for the treatment of mammalian diseases associated with cathepsin S including Alzheimer's disease, atherosclerosis, chronic obstructive pulmonary disease, cancer and certain autoimmune disorders, including, but not limited to juvenile onset diabetes, multiple sclerosis, pemphigus vulgaris, Graves' disease, myasthenia gravis, systemic lupus erythemotasus, rheumatoid arthritis and Hashimoto's thyroiditis; allergic disorders, including, but not limited to asthma; and allogenic immune responses, including, but not limited to, rejection of organ transplants or tissue grafts. It is known in the literature that cathepsin S activity is associated with the above disease states, see Munger J S, Haass C, Lemere C A, Shi G P, Wong W S, Teplow D B, Selkoe D J, Chapman H A. Lysosomal processing of amyloid precursor protein to A beta peptides: a distinct role for cathepsin S. Biochem J 1995 311, 299-305, Sukhova G K, Zhang Y, Pan J H, Wada Y, Yamamoto T, Naito M, Kodama T, Tsimikas S, Witztum J L, Lu M L, Sakara Y, Chin M T, Libby P, Shi G P. Deficiency of cathepsin S reduces atherosclerosis in LDL receptor-deficient mice. J Clin Invest 2003 111, 897-906, Zheng T, Zhu Z, Wang Z, Homer R J, Ma B, Riese R J Jr, Chapman H A Jr, Shapiro S D, Elias J A. Inducible targeting of IL-13 to the adult lung causes matrix metalloproteinase- and cathepsin-dependent emphysema. J Clin Invest 2000 106, 1081-93, Shi G P, Sukhova G K, Kuzuya M, Ye Q, Du J, Zhang Y, Pan J H, Lu M L, Cheng X W, Iguchi A, Perrey S, Lee A M, Chapman H A, Libby P. Deficiency of the cysteine protease cathepsin S impairs microvessel growth. Circ Res 2003 92, 493-500, Nakagawa T Y, Brissette W H, Lira P D, Griffiths R J, Petrushova N, Stock J, McNeish J D, Eastman S E, Howard E D, Clarke S R, Rosloniec E F, Elliott E A, Rudensky A Y. Impaired invariant chain degradation and antigen presentation and diminished collagen-induced arthritis in cathepsin S null mice. Immunity 1999 10, 207-17.

Exemplifying the invention is the use of any of the compounds described above in the preparation of a medicament for the treatment and/or prevention of osteoporosis in a mammal in need thereof. Still further exemplifying the invention is the use of any of the compounds described above in the preparation of a medicament for the treatment and/or prevention of: bone loss, bone resorption, bone fractures, metastatic bone disease and/or disorders related to cathepsin functioning.

The compounds of this invention may be administered to mammals, preferably humans, either alone or, preferably, in combination with pharmaceutically acceptable carriers or diluents, optionally with known adjuvants, such as alum, in a pharmaceutical composition, according to standard pharmaceutical practice. The compounds can be administered orally or parenterally, including the intravenous, intramuscular, intraperitoneal, subcutaneous, rectal and topical routes of administration.

In the case of tablets for oral use, carriers which are commonly used include lactose and corn starch, and lubricating agents, such as magnesium stearate, are commonly added. For oral administration in capsule form, useful diluents include lactose and dried corn starch. For oral use of a therapeutic compound according to this invention, the selected compound may be administered, for example, in the form of tablets or capsules, or as an aqueous solution or suspension. For oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. When aqueous suspensions are required for oral use, the active ingredient is combined with emulsifying and suspending agents. If desired, certain sweetening and/or flavoring agents may be added. For intramuscular, intraperitoneal, subcutaneous and intravenous use, sterile solutions of the active ingredient are usually prepared, and the pH of the solutions should be suitably adjusted and buffered. For intravenous use, the total concentration of solutes should be controlled in order to render the preparation isotonic.

The compounds of the present invention may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

Compounds of the present invention may also be delivered by the use of monoclonal antibodies as individual carriers to which the compound molecules are coupled. The compounds of the present invention may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polyactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

The instant compounds may also be useful in combination with known agents useful for treating or preventing osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, metastatic bone disease, hypercalcemia of malignancy, and multiple myeloma. Combinations of the presently disclosed compounds with other agents useful in treating or preventing osteoporosis or other bone disorders are within the scope of the invention. A person of ordinary skill in the art would be able to discern which combinations of agents would be useful based on the particular characteristics of the drugs and the disease involved. Such agents include the following: an organic bisphosphonate; a selective estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; Vitamin D; a synthetic Vitamin D analogue; a Nonsteroidal anti-inflammatory drug; a selective cyclooxygenase-2 inhibitor; an inhibitor of interleukin-1 beta; a LOX/COX inhibitor; and the pharmaceutically acceptable salts and mixtures thereof. A preferred combination is a compound of the present invention and an organic bisphosphonate. Another preferred combination is a compound of the present invention and a selective estrogen receptor modulator. Another preferred combination is a compound of the present invention and an androgen receptor modulator. Another preferred combination is a compound of the present invention and an osteoblast anabolic agent. "Organic bisphosphonate" includes, but is not limited to, compounds of the chemical formula

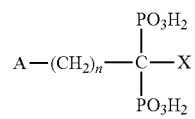

wherein n is an integer from 0 to 7 and wherein A and X are independently selected from the group consisting of H, OH, halogen, $NH_2$, SH, phenyl, $C_1$-$C_{30}$ alkyl, $C_3$-$C_{30}$ branched or cycloalkyl, bicyclic ring structure containing two or three N, $C_1$-$C_{30}$ substituted alkyl, $C_1$-$C_{10}$ alkyl substituted $NH_2$, $C_3$-$C_{10}$ branched or cycloalkyl substituted $NH_2$, $C_1$-$C_{10}$ dialkyl substituted $NH_2$, $C_1$-$C_{10}$ alkoxy, $C_1$-$C_{10}$ alkyl substituted thio, thiophenyl, halophenylthio, $C_1$-$C_{10}$ alkyl substituted phenyl, pyridyl, furanyl, pyrrolidinyl, imidazolyl, imidazopyridinyl, and benzyl, such that both A and X are not selected from H or OH when n is 0; or A and X are taken together with the carbon atom or atoms to which they are attached to form a $C_3$-$C_{10}$ ring.

In the foregoing chemical formula, the alkyl groups can be straight, branched, or cyclic, provided sufficient atoms are selected for the chemical formula. The $C_1$-$C_{30}$ substituted alkyl can include a wide variety of substituents, nonlimiting examples which include those selected from the group consisting of phenyl, pyridyl, furanyl, pyrrolidinyl, imidazonyl, $NH_2$, $C_1$-$C_{10}$ alkyl or dialkyl substituted $NH_2$, OH, SH, and $C_1$-$C_{10}$ alkoxy.

The foregoing chemical formula is also intended to encompass complex carbocyclic, aromatic and hetero atom structures for the A and/or X substituents, nonlimiting examples of which include naphthyl, quinolyl, isoquinolyl, adamantyl, and chlorophenylthio.

Pharmaceutically acceptable salts and derivatives of the bisphosphonates are also useful herein. Non-limiting examples of salts include those selected from the group consisting alkali metal, alkaline metal, ammonium, and mono-, di-, tri-, or tetra-$C_1$-$C_{10}$-alkyl-substituted ammonium. Preferred salts are those selected from the group consisting of sodium, potassium, calcium, magnesium, and ammonium salts. More preferred are sodium salts. Non-limiting examples of derivatives include those selected from the group consisting of esters, hydrates, and amides.

It should be noted that the terms "bisphosphonate" and "bisphosphonates", as used herein in referring to the therapeutic agents of the present invention are meant to also encompass diphosphonates, biphosphonic acids, and diphosphonic acids, as well as salts and derivatives of these materials. The use of a specific nomenclature in referring to the bisphosphonate or bisphosphonates is not meant to limit the scope of the present invention, unless specifically indicated. Because of the mixed nomenclature currently in use by those of ordinary skill in the art, reference to a specific weight or percentage of a bisphosphonate compound in the present invention is on an acid active weight basis, unless indicated otherwise herein. For example, the phrase "about 5 mg of a bone resorption inhibiting bisphosphonate selected from the group consisting of alendronate, pharmaceutically acceptable salts thereof, and mixtures thereof, on an alendronic acid active weight basis" means that the amount of the bisphosphonate compound selected is calculated based on 5 mg of alendronic acid.

Non-limiting examples of bisphosphonates useful herein include the following:

Alendronate, which is also known as alendronic acid, 4-amino-1-hydroxybutylidene-1,1-bisphosphonic acid, alendronate sodium or alendronate monosodium trihydrate, 4-amino-1-hydroxybutylidene-1,1-bisphosphonic acid monosodium trihydrate.

Alendronate is described in U.S. Pat. No. 4,922,007, to Kieczykowski et al., issued May 1, 1990; U.S. Pat. No. 5,019,651, to Kieczykowski et al., issued May 28, 1991; U.S. Pat. No. 5,510,517, to Dauer et al., issued Apr. 23, 1996; U.S. Pat. No. 5,648,491, to Dauer et al., issued Jul. 15, 1997, all of which are incorporated by reference herein in their entirety.

Cycloheptylaminomethylene-1,1-bisphosphonic acid, YM 175, Yamanouchi (incadronate, formerly known as cimadronate), as described in U.S. Pat. No. 4,970,335, to Isomura et al., issued Nov. 13, 1990, which is incorporated by reference herein in its entirety.

1,1-dichloromethylene-1,1-diphosphonic acid (clodronic acid), and the disodium salt (clodronate, Procter and Gamble), are described in Belgium Patent 672,205 (1966) and *J. Org. Chem* 32, 4111 (1967), both of which are incorporated by reference herein in their entirety.

1-hydroxy-3-(1-pyrrolidinyl)-propylidene-1,1-bisphosphonic acid (EB-1053).

1-hydroxyethane-1,1-diphosphonic acid (etidronic acid).

1-hydroxy-3-(N-methyl-N-pentylamino)propylidene-1,1-bisphosphonic acid, also known as BM-210955, Boehringer-Mannheim (ibandronate), is described in U.S. Pat. No. 4,927,814, issued May 22, 1990, which is incorporated by reference herein in its entirety.

1-hydroxy-2-imidazo-(1,2-a)pyridin-3-yethylidene (minodronate).

6-amino-1-hydroxyhexylidene-1,1-bisphosphonic acid (neridronate).

3-(dimethylamino)-1-hydroxypropylidene-1,1-bisphosphonic acid (olpadronate).

3-amino-1-hydroxypropylidene-1,1-bisphosphonic acid (pamidronate).

[2-(2-pyridinyl)ethylidene]-1,1-bisphosphonic acid (piridronate) is described in U.S. Pat. No. 4,761,406, which is incorporated by reference in its entirety.

1-hydroxy-2-(3-pyridinyl)-ethylidene-1,1-bisphosphonic acid (risedronate).

(4-chlorophenyl)thiomethane-1,1-disphosphonic acid (tiludronate) as described in U.S. Pat. No. 4,876,248, to Breliere et al., Oct. 24, 1989, which is incorporated by reference herein in its entirety.

1-hydroxy-2-(1H-imidazol-1-yl)ethylidene-1,1-bisphosphonic acid (zoledronate).

Nonlimiting examples of bisphosphonates include alendronate, cimadronate, clodronate, etidronate, ibandronate, incadronate, minodronate, neridronate, olpadronate, pamidronate, piridronate, risedronate, tiludronate, and zolendronate, and pharmaceutically acceptable salts and esters thereof. A particularly preferred bisphosphonate is alendronate, especially a sodium, potassium, calcium, magnesium or ammonium salt of alendronic acid. Exemplifying the preferred bisphosphonate is a sodium salt of alendronic acid, especially a hydrated sodium salt of alendronic acid. The salt can be hydrated with a whole number of moles of water or non whole numbers of moles of water. Further exemplifying the preferred bisphosphonate is a hydrated sodium salt of alendronic acid, especially when the hydrated salt is alendronate monosodium trihydrate.

It is recognized that mixtures of two or more of the bisphosphonate actives can be utilized.

The precise dosage of the organic bisphosphonate will vary with the dosing schedule, the particular bisphosphonate chosen, the age, size, sex and condition of the mammal or human, the nature and severity of the disorder to be treated, and other relevant medical and physical factors. Thus, a precise pharmaceutically effective amount cannot be specified in advance and can be readily determined by the caregiver or clinician. Appropriate amounts can be determined by routine experimentation from animal models and human clinical studies. Generally, an appropriate amount of bisphosphonate is chosen to obtain a bone resorption inhibiting effect, i.e. a bone resorption inhibiting amount of the bisphosphonate is administered. For humans, an effective oral dose of bisphosphonate is typically from about 1.5 to about 6000 µg/kg body weight and preferably about 10 to about 2000 µg/kg of body weight. For alendronate monosodium trihydrate, common human doses which are administered are generally in the range of about 2 mg/day to about 40 mg/day, preferably about 5 mg/day to about 40 mg/day. In the U.S. presently approved dosages for alendronate monosodium trihydrate are 5 mg/day for preventing osteoporosis, 10 mg/day for treating osteoporosis, and 40 mg/day for treating Paget's disease.

In alternative dosing regimens, the bisphosphonate can be administered at intervals other than daily, for example once-weekly dosing, twice-weekly dosing, biweekly dosing, and twice-monthly dosing. In a once weekly dosing regimen, alendronate monosodium trihydrate would be administered at dosages of 35 mg/week or 70 mg/week.

"Selective estrogen receptor modulators" refers to compounds which interfere or inhibit the binding of estrogen to the receptor, regardless of mechanism. Examples of estrogen receptor modulators include, but are not limited to, estrogen, progestogen, estradiol, droloxifene, raloxifene, lasofoxifene, TSE-424, tamoxifen, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

An "estrogen receptor beta modulator" is a compound that selectively agonizes or antagonizes estrogen receptor beta (ERβ Agonizing ERβ increases transcription of the tryptophan hydroxylase gene (TPH, the key enzyme in serotonin synthesis) via an ERβ mediated event. Examples of estrogen receptor beta agonists can be found in PCT International publication WO 01/82923, which published on Nov. 8, 2001, and WO 02/41835, which published on May 20, 2002, both of which are hereby incorporated by reference in their entirety.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"An inhibitor of osteoclast proton ATPase" refers to an inhibitor of the proton ATPase, which is found on the apical membrane of the osteoclast, and has been reported to play a significant role in the bone resorption process. This proton pump represents an attractive target for the design of inhibitors of bone resorption which are potentially useful for the treatment and prevention of osteoporosis and related metabolic diseases. See C. Farina et al., "Selective inhibitors of the osteoclast vacuolar proton ATPase as novel bone antiresorptive agents," DDT, 4: 163-172 (1999)), which is hereby incorporated by reference in its entirety.

"HMG-CoA reductase inhibitors" refers to inhibitors of 3-hydroxy-3-methylglutaryl-CoA reductase. Compounds which have inhibitory activity for HMG-CoA reductase can be readily identified by using assays well-known in the art. For example, see the assays described or cited in U.S. Pat. No. 4,231,938 at col. 6, and WO 84/02131 at pp. 30-33. The terms "HMG-CoA reductase inhibitor" and "inhibitor of HMG-CoA reductase" have the same meaning when used herein.

Examples of HMG-CoA reductase inhibitors that may be used include but are not limited to lovastatin (MEVACOR; see U.S. Pat. Nos. 4,231,938, 4,294,926 and 4,319,039), simvastatin (ZOCOR®; see U.S. Pat. Nos. 4,444,784, 4,820, 850 and 4,916,239), rosuvastatin (particularly the calcium salt sold in CRESTOR®), pravastatin (PRAVACHOL®; see U.S. Pat. Nos. 4,346,227, 4,537,859, 4,410,629, 5,030,447 and 5,180,589), fluvastatin (LESCOL®; see U.S. Pat. Nos. 5,354,772, 4,911,165, 4,929,437, 5,189,164, 5,118,853, 5,290,946 and 5,356,896), atorvastatin (LIPITOR®; see U.S. Pat. Nos. 5,273,995, 4,681,893, 5,489,691 and 5,342, 952) and cerivastatin (also known as rivastatin and BAYCHOL®; see U.S. Pat. No. 5,177,080). The structural formulas of these and additional HMG-CoA reductase inhibitors that may be used in the instant methods are described at page 87 of M. Yalpani, "Cholesterol Lowering Drugs", Chemistry & Industry, pp. 85-89 (5 Feb. 1996) and U.S. Pat. Nos. 4,782,084 and 4,885,314. The term HMG-CoA reductase inhibitor as used herein includes all pharmaceutically acceptable lactone and open-acid forms (i.e., where the lactone ring is opened to form the free acid) as well as salt and ester forms of compounds which have HMG-CoA reductase inhibitory activity, and therefor the use of such salts, esters, open-acid and lactone forms is included within the scope of this invention. An illustration of the lactone portion and its corresponding open-acid form is shown below as structures I and II.

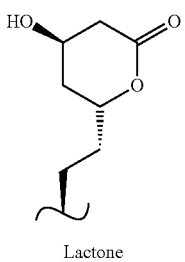

Lactone

I

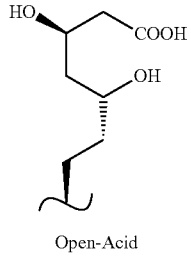

Open-Acid

II

In HMG-CoA reductase inhibitors where an open-acid form can exist, salt and ester forms may preferably be formed from the open-acid, and all such forms are included within the meaning of the term "HMG-CoA reductase inhibitor" as used herein. Preferably, the HMG-CoA reductase inhibitor is selected from lovastatin and simvastatin, and most preferably simvastatin. Herein, the term "pharmaceutically acceptable salts" with respect to the HMG-CoA reductase inhibitor shall mean non-toxic salts of the compounds employed in this invention which are generally prepared by reacting the free acid with a suitable organic or inorganic base, particularly those formed from cations such as sodium, potassium, aluminum, calcium, lithium, magnesium, zinc and tetramethylammonium, as well as those salts formed from amines such as ammonia, ethylenediamine, N-methylglucamine, lysine, arginine, ornithine, choline, N,N'-dibenzylethylenediamine, chloroprocaine, diethanolamine, procaine, N-benzylphenethylamine, 1-p-chlorobenzyl-2-pyrrolidine-1'-yl-methylbenz-imidazole, diethylamine, piperazine, and tris(hydroxymethyl) aminomethane. Further examples of salt forms of HMG-CoA reductase inhibitors may include, but are not limited to, acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynapthoate, iodide, isothionate, lactate, lactobionate, laurate, malate, maleate, mandelate, mesylate, methylsulfate, mucate, napsylate, nitrate, oleate, oxalate, pamaote, palmitate, panthothenate, phosphate/diphosphate, polygalacturonate, salicylate, stearate, subacetate, succinate, tannate, tartrate, teoclate, tosylate, triethiodide, and valerate.

Ester derivatives of the described HMG-CoA reductase inhibitor compounds may act as prodrugs which, when absorbed into the bloodstream of a warm-blooded animal, may cleave in such a manner as to release the drug form and permit the drug to afford improved therapeutic efficacy.

As used above, "integrin receptor antagonists" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha_v\beta_3$ integrin and the $\alpha_v\beta_5$ integrin, and to compounds which antagonize, inhibit or counteract the activity of the particular integrin(s) expressed on capillary endothelial cells. The term also refers to antagonists of the $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_1\beta_4$ integrins. The term also refers to antagonists of any combination of $\alpha_v\beta_3$, $\alpha_v\beta_5$, $\alpha_v\beta_6$, $\alpha_v\beta_8$, $\alpha_1\beta_1$, $\alpha_2\beta_1$, $\alpha_5\beta_1$, $\alpha_6\beta_1$ and $\alpha_6\beta_4$ integrins. H. N. Lode and coworkers in PNAS USA 96: 1591-1596 (1999) have observed synergistic effects between an antiangiogenic a v integrin antagonist and a tumor-specific antibody-cytokine (interleukin-2) fusion protein in the eradication of spontaneous tumor metastases. Their results suggested this combination as having potential for the treatment of cancer and metastatic tumor growth. $\alpha_v\beta_3$ integrin receptor antagonists inhibit bone resorption through a new mechanism distinct from that of all currently available drugs. Integrins are heterodimeric transmembrane adhesion receptors that mediate cell-cell and cell-matrix interactions. The $\alpha$ and $\beta$ integrin subunits interact non-covalently and bind extracellular matrix ligands in a divalent cation-dependent manner. The most abundant integrin on osteoclasts is $\alpha_v\beta_3$ ($>10^7$/osteoclast), which appears to play a rate-limiting role in cytoskeletal organization important for cell migration and polarization. The $\alpha_v\beta_3$ antagonizing effect is selected from inhibition of bone resorption, inhibition of restenosis, inhibition of macular degeneration, inhibition of arthritis, and inhibition of cancer and metastatic growth.

"An osteoblast anabolic agent" refers to agents that build bone, such as PTH. The intermittent administration of parathyroid hormone (PTH) or its amino-terminal fragments and analogues have been shown to prevent, arrest, partially reverse bone loss and stimulate bone formation in animals and humans. For a discussion refer to D. W. Dempster et al., "Anabolic actions of parathyroid hormone on bone," Endocr Rev 14: 690-709 (1993). Studies have demonstrated the clinical benefits of parathyroid hormone in stimulating bone formation and thereby increasing bone mass and strength. Results were reported by R M Neer et al., in New Eng J Med 344 1434-1441 (2001).

In addition, parathyroid hormone-related protein fragments or analogues, such as PTHrP-(1-36) have demonstrated potent anticalciuric effects [see M. A. Syed et al., "Parathyroid hormone-related protein-(1-36) stimulates renal tubular calcium reabsorption in normal human volunteers: implications for the pathogenesis of humoral hypercalcemia of malignancy," JCEM 86: 1525-1531 (2001)] and may also have potential as anabolic agents for treating osteoporosis.

"Vitamin D" includes, but is not limited to, vitamin $D_3$ (cholecalciferol) and vitamin $D_2$ (ergocalciferol), which are naturally occurring, biologically inactive precursors of the hydroxylated biologically active metabolites of vitamin D: 1α-hydroxy vitamin D; 25-hydroxy vitamin D, and 1α,25-dihydroxy vitamin D. Vitamin $D_2$ and vitamin $D_3$ have the same biological efficacy in humans. When either vitamin $D_2$ or $D_3$ enters the circulation, it is hydroxylated by cytochrome $P_{450}$-vitamin D-25-hydroxylase to give 25-hydroxy vitamin D. The 25-hydroxy vitamin D metabolite is biologically inert and is further hydroxylated in the kidney by cytochrome P450-monooxygenase, 25 (OH) D-1α-hydroxylase to give 1,25-dihydroxy vitamin D. When serum calcium decreases, there is an increase in the production of parathyroid hormone (PTH), which regulates calcium homeostasis and increases plasma calcium levels by increasing the conversion of 25-hydroxy vitamin D to 1,25-dihydroxy vitamin D.

1,25-dihydroxy vitamin D is thought to be responsible for the effects of vitamin D on calcium and bone metabolism. The 1,25-dihydroxy metabolite is the active hormone required to maintain calcium absorption and skeletal integrity. Calcium homeostasis is maintained by 1,25-dihydroxy vitamin D by inducing monocytic stem cells to differentiate into osteoclasts and by maintaining calcium in the normal range, which results in bone mineralization by the deposition of calcium hydroxyapatite onto the bone surface, see Holick, M F, Vitamin D photobiology, metabolism, and clinical applications, In: DeGroot L, Besser H, Burger H G, eg al., eds. Endocrinology, $3^{rd}$ ed., 990-1013 (1995). However, elevated levels of 1α,25-dihydroxy vitamin $D_3$ can result in an increase of calcium concentration in the blood and in the abnormal control of calcium concentration by bone metabolism, resulting in hypercalcemia. 1α,25-dihydroxy vitamin $D_3$ also indirectly regulates osteoclastic activity in bone metabolism and elevated levels may be expected to increase excessive bone resorption in osteoporosis.

"Synthetic vitamin D analogues" includes non-naturally occurring compounds that act like vitamin D.

"Nonsteroidal anti-inflammatory drugs" or NSAIDs, inhibit the metabolism of arachidonic acid to proinflammatory prostaglandins via cyclooxygenase (COX)-1 and COX-2. Nonlimiting examples of NSAIDs include: aspirin, ibuprofen, naproxen, diclofenac, etodolac, fenoporfen, flubiprofen, indomethacin, ketoprofen, ketorolac, meloxicam, nabumetone, oxaprozin, piroxicam, sulindac, tolmetin, diflunisal, meclofenamate and phenylbutazone.

A "selective cyclooxygenase-2 inhibitor," or COX-2 inhibitor, refers to a type of nonsteroidal anti-inflammatory drug (NSAID), that inhibit the COX-2 coenzyme, which contributes to pain and inflammation in the body. Nonlimiting examples of COX-2 inhibitos include: celecoxib, etoricoxib, parecoxib, rofecoxib, valdecoxib and lumiracoxib.

An "inhibitor of interleukin-1 beta" or IL-1β refers to in inhibitors of IL-1, which is a soluble factor produced by monocytes, macrophages, and other cells which activates T-lymphocytes and potentiates their response to mitogens or antigens. Nonlimiting examples of IL-1B inhibitors include diacerein and rhein.

A "LOX/COX inhibitor" refers to an inhibitor or all three of the major enzymes involved in arachidonic acid pathway—namely, 5-LOX, COX-1 and COX-2. A nonlimiting example of a LOX/COX inhibitor is licofelone.

If formulated as a fixed dose, such combination products employ the compounds of this invention within the dosage range described below and the other pharmaceutically active agent(s) within its approved dosage range. Compounds of the instant invention may alternatively be used sequentially with known pharmaceutically acceptable agent(s) when a combination formulation is inappropriate.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents. The present invention includes within its scope prodrugs of the compounds of this invention. In general, such prodrugs will be functional derivatives of the compounds of this invention which are readily convertible in vivo into the required compound. Thus, in the methods of treatment of the present invention, the term "administering" shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985, which is incorporated by reference herein in its entirety. Metabolites of these compounds include active species produced upon introduction of compounds of this invention into the biological milieu.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The terms "treating" or "treatment" of a disease as used herein includes: inhibiting the disease, i.e., arresting or reducing the development of the disease or its clinical symptoms; or relieving the disease, i.e., causing regression of the disease or its clinical symptoms.

The terms "preventing" or "prevention" of a disease as used herein includes: causing the clinical symptoms of the disease not to develop in a mammal that may be exposed to or predisposed to the disease but does not yet experience or display symptoms of the disease.

The term "bone resorption," as used herein, refers to the process by which osteoclasts degrade bone.

The present invention also encompasses a pharmaceutical composition useful in the treatment of osteoporosis or other bone disorders, comprising the administration of a therapeutically effective amount of a compound of Formula I of this invention, with or without pharmaceutically acceptable carriers or diluents. Suitable compositions of this invention include aqueous solutions comprising compounds of this invention and pharmacologically acceptable carriers, e.g., saline, at a pH level, e.g., 7.4. The solutions may be introduced into a patient's bloodstream by local bolus injection.

When a compound according to this invention is administered into a human subject, the daily dosage will normally be determined by the prescribing physician with the dosage generally varying according to the age, weight, and response of the individual patient, as well as the severity of the patient's symptoms.

In one exemplary application, a suitable amount of compound is administered to a mammal undergoing treatment for a cathepsin dependent condition. Oral dosages of the present invention, when used for the indicated effects, will range between about 0.01 mg per kg of body weight per day (mg/kg/day) to about 100 mg/kg/day, preferably 0.01 to 10 mg/kg/day, and most preferably 0.1 to 5.0 mg/kg/day. For oral administration, the compositions are preferably provided in the form of tablets containing 0.01, 0.05, 0.1, 0.5, 1.0, 2.5, 5.0, 10.0, 15.0, 25.0, 50.0, 100 and 500 milligrams of the active ingredient for the symptomatic adjustment of the dosage to the patient to be treated. A medicament typically contains from about 0.01 mg to about 500 mg of the active ingredient, preferably, from about 1 mg to about 100 mg of active ingredient. Intravenously, the most preferred doses will range from about 0.1 to about 10 mg/kg/minute during a constant rate infusion. Advantageously, compounds of the present invention may be administered in a single daily dose, or the total daily dosage may be administered in divided doses of two, three or four times daily. Furthermore, preferred compounds for the present invention can be administered in intranasal form via topical use of suitable intranasal vehicles, or via transdermal routes, using those forms of transdermal skin patches well known to those of ordinary skill in the art. To be administered in the form of a transdermal delivery system, the dosage administration will, of course, be continuous rather than intermittent throughout the dosage regimen.

The compounds of the present invention can be used in combination with other agents useful for treating cathepsin-mediated conditions. The individual components of such combinations can be administered separately at different times during the course of therapy or concurrently in divided or single combination forms. The instant invention is therefore to be understood as embracing all such regimes of simultaneous or alternating treatment and the term "administering" is to be interpreted accordingly. It will be understood that the scope of combinations of the compounds of this invention with other agents useful for treating cathepsin-mediated conditions includes in principle any combination with any pharmaceutical composition useful for treating disorders related to estrogen functioning.

The scope of the invention therefore encompasses the use of a compound of Formula I in combination with a second agent selected from: an organic bisphosphonate; a selective estrogen receptor modulator; an androgen receptor modulator; an inhibitor of osteoclast proton ATPase; an inhibitor of HMG-CoA reductase; an integrin receptor antagonist; an osteoblast anabolic agent, such as PTH; Vitamin D; a synthetic Vitamin D analogue; a Nonsteroidal anti-inflammatory drug; a selective cyclooxygenase-2 inhibitor; an inhibitor of interleukin-1 beta; a LOX/COX inhibitor and the pharmaceutically acceptable salts and mixtures thereof.

These and other aspects of the invention will be apparent from the teachings contained herein.

Definitions

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to comprehend all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Tautomers of compounds defined in Formula I are also included within the scope of the present invention. For example, compounds including carbonyl —$CH_2C(O)$— groups (keto forms) may undergo tautomerism to form hydroxyl —CH=C(OH)— groups (enol forms). Both keto and enol forms are included within the scope of the present invention.

When any variable (e.g. $R^3$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. An example is silinane. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

"Celite®" (Fluka) diatomite is diatomaceous earth, and can be referred to as "celite."

As used herein, "alkyl" is intended to include both branched and straight-chain saturated aliphatic hydrocarbon groups having one to ten carbon atoms unless otherwise specified. For example, $C_1$-$C_{10}$, as in "$C_1$-$C_{10}$ alkyl" is defined to include groups having 1, 2, 3, 4, 5, 6, 7, 8, 9 or 10 carbons in a linear or branched arrangement. For example, "$C_1$-$C_{10}$ alkyl" specifically includes methyl, ethyl, propyl, butyl, pentyl, hexyl, heptyl, octyl, nonyl, decyl, and so on.

The term "haloalkyl" means an alkyl radical as defined above, unless otherwise specified, that is substituted with one to five, preferably one to three halogen. Representative examples include, but are not limited to difluoromethyl, trifluoromethyl, trifluoroethyl, perfluoroethyl, dichloroethyl, and the like.

The term "cycloalkyl" means a monocyclic or bicyclic saturated aliphatic hydrocarbon group having the specified number of carbon atoms. For example, "cycloalkyl" includes cyclopropyl, methyl-cyclopropyl, 2,2-dimethyl-cyclobutyl, 2-ethyl-cyclopentyl, cyclohexyl, and so on. The term "cycloalkyl" includes bridged systems, including bicycle[1.1.1]pnetanyl, bicyclo[3.1.0]hexanyl, azabicyclo[3.2.1]heptanyl and bicyclo[3.2.1]octanyl.

If no number of carbon atoms is specified, the term "alkenyl" refers to a non-aromatic hydrocarbon radical, straight or branched, containing from 2 to 10 carbon atoms and at least 1 carbon to carbon double bond. Preferably 1 carbon to carbon double bond is present, and up to 4 non-aromatic carbon-carbon double bonds may be present. Thus, "$C_2$-$C_6$ alkenyl" means an alkenyl radical having from 2 to 6 carbon atoms. Alkenyl groups include ethenyl, propenyl, butenyl and cyclohexenyl. As described above with respect to alkyl, the straight or branched portion of the alkenyl group may contain double bonds and may be substituted if a substituted alkenyl group is indicated.

If no number of carbon atoms is specified, the term "alkynyl" refers to a non-aromatic hydrocarbon radical, straight or branched, containing from 2 to 10 carbon atoms and at least 1 carbon to carbon triple bond. Preferably 1 carbon to carbon triple bond is present, and up to 4 non-aromatic carbon-carbon triple bonds may be present. Thus, "$C_2$-$C_6$ alkynyl" means an alkynyl radical having from 2 to 6 carbon atoms. Alkynyl groups include ethynyl, propynyl, butynyl and cyclohexynyl. As described above with respect to alkyl, the straight or branched portion of the alkynyl group may contain triple bonds and may be substituted if a substituted alkynyl group is indicated.

As used herein, "aryl" is intended to mean any stable monocyclic or bicyclic carbon ring of up to 12 atoms in each ring, wherein at least one ring is aromatic. Examples of such aryl elements include phenyl, naphthyl, tetrahydronaphthyl, indanyl, biphenyl, phenanthryl, anthryl or acenaphthyl.

The term "heteroaryl", as used herein, represents a stable monocyclic, bicyclic or tricyclic ring of up to 10 atoms in each ring, wherein at least one ring is aromatic and contains from 1 to 4 heteroatoms selected from the group consisting of O, N and S. The term "heteroaryl" includes bicyclic rings wherein one ring is aromatic and the other is not; in these instances, the heteroatom(s) can be in either the aromatic or nonaromatic ring, for example, indolinyl. Heteroaryl groups within the scope of this definition include but are not limited to: benzoimidazolyl, benzofuranyl, benzofurazanyl, benzopyrazolyl, benzotriazolyl, benzothiophenyl, benzoxazolyl, carbazolyl, carbolinyl, cinnolinyl, furanyl, indolinyl, indolyl, indolazinyl, indazolyl, isobenzofuranyl, isoindolyl, isoquinolyl, isothiazolyl, isoxazolyl, naphthpyridinyl, oxadiazolyl, oxazolyl, oxazoline, isoxazoline, pyranyl, pyrazinyl, pyrazolyl, pyridazinyl, pyridopyridinyl, pyridyl, pyrimidinyl, pyrrolyl, quinazolinyl, quinolyl, quinoxalinyl, tetrazolyl, tetrazolopyridyl, thiadiazolyl, thiazolyl, thienyl, triazolyl, dihydrobenzoimidazolyl, dihydrobenzofuranyl, dihydrobenzothiophenyl, dihydrobenzoxazolyl, dihydroindolyl, dihydroquinolinyl, methylenedioxybenzene, benzothiazolyl, benzothienyl, quinolinyl, isoquinolinyl, oxazolyl, and tetra-hydroquinoline. If the heteroaryl contains nitrogen atoms, it is understood that the corresponding N-oxides thereof are also encompassed by this definition.

The term "heterocycle" or "heterocyclyl" as used herein is intended to mean a 5- to 10-membered nonaromatic ring, unless otherwise specified, containing from 1 to 4 heteroatoms selected from the group consisting of O, N, S, SO, or $SO_2$ and includes bicyclic groups. "Heterocyclyl" therefore includes, but is not limited to the following: piperazinyl, piperidinyl, pyrrolidinyl, morpholinyl, thiomorpholinyl, dioxidomorpholinyl, iminooxidothiomorpholinyl, tetrahydropyranyl, dihydropiperidinyl, tetrahydrothiophenyl and the like. If the heterocycle contains a nitrogen, it is understood that the corresponding N-oxides thereof are also emcompassed by this definition.

As appreciated by those of skill in the art, "halo" or "halogen" as used herein is intended to include chloro, fluoro, bromo and iodo.

In certain instances, substituents may be defined with a range of carbons that includes zero, such as $(C_0-C_6)$alkylene-aryl. If aryl is taken to be phenyl, this definition would include phenyl itself as well as —$CH_2Ph$, —$CH_2CH_2Ph$, $CH(CH_3)$ $CH_2CH(CH_3)Ph$, and so on.

The present invention also includes N-oxide derivatives and protected derivatives of compounds of Formula I. For example, when compounds of Formula I contain an oxidizable nitrogen atom, the nitrogen atom can be converted to an N-oxide by methods well known in the art. Also when compounds of Formula I contain groups such as hydroxy, carboxy, thiol or any group containing a nitrogen atom(s), these groups can be protected with a suitable protecting groups. A comprehensive list of suitable protective groups can be found in T. W. Greene, Protective Groups in Organic Synthesis, John Wiley & Sons, Inc. 1981, the disclosure of which is incorporated herein by reference in its entirety. The protected derivatives of compounds of Formula I can be prepared by methods well known in the art.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. It will be understood that, as used herein, references to the compounds of Formula I are meant to also include the pharmaceutically acceptable salts.

For purposes of this specification, the following abbreviations have the indicated meanings:

Bn=benzyl
CuCN=copper (I) cyanide
DAST=diethylaminosulfur trifluoride
DCE=1,2-dichloroethane
DCM=dichloromathane
DIEA=diisopropylethylamine
DIPEA=diisopropylethylamine
DMF=N,N-dimethylformamide
DMSO=dimethylsulfoxide
DTT=dithiothreitol
EDTA=ethylenediaminetetraacetic acid
EtOAc=ethyl acetate
$Et_3N$=triethylamine
EtOH=ethanol
HATU=2-(3H-[1,2,3]triazolo[4,5-b]pyridin-3-yl)-1,1,3,3-tetramethylisouronium hexafluorophosphate (V)
HBTU=O-(Benzotriazol-1-yl)-N,N,N',N'-tetramethyluronium hexafluorophosphate (V)
Hunig's Base=diisopropylethylamine
HPLC=high performance liquid chromatography
IPA=isopropyl alcohol
LG=leaving group
Lawesson's reagent=2,4-bis(4-methoxyphenyl)-1,3,2,4-dithiadiphosphetane 2,4-disulfide
MeCN=acetonitrile
MeOH=methanol
MES=2-(N-morpholino)ethanesulfonic acid
MTBE=methyl tert-butyl ether
NCS=N-cholorosuccinimide
$PdCl_2$(dppf)=[1,1'-bis(diphenylphosphino)ferrocene]dichloropalladium(II)
PG=protecting group
Ph=phenyl
$Pr_2NEt$=N,N-diisopropylethylamine
RT or rt=room temperature
sat. aq.=saturated aqueous
SFC=supercritical fluid chromatography
TBAF=tetrabutylammonium fluoride
TFA=trifluoroacetic acid
THF=tetrahydrofuran tlc=thin layer chromatography
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl The compounds disclosed in the present application exhibited activity in the following assays. In addition, the compounds disclosed in the present application have an enhanced pharmacological profile relative to previously disclosed compounds.

Cathepsin K Assay (hrbCat K)

Serial dilutions (⅓) from 500 μM down to 0.025 μM of test compounds were prepared in dimethyl sulfoxide (DMSO). Then 0.5 μL of DMSO from each dilution were added to 18.75 μL of assay buffer (MES, 50 mM (pH 5.5); EDTA, 2.5 mM; DTT, 2.5 mM and 10% DMSO) containing human cathepsin K (0.4 nM) in assay buffer solution. The assay solutions were mixed for 5-10 seconds on a shaker plate and incubated for 15 minutes at room temperature. Z-Leu-Arg-AMC (8 μM) in 6.25 μL of assay buffer was added to the assay solutions. Hydrolysis of the coumarin leaving group (AMC) was followed by spectrofluorometry (Exλ=360 nm; Emλ=460 nm) for 30 minutes. Percent of inhibition were calculated by fitting experimental values to standard mathematical model for dose response curve.

Cathepsin L Assay

Serial dilutions (1/3) from 500 μM down to 0.025 μM of test compounds were prepared in dimethyl sulfoxide (DMSO). Then 0.5 μL of DMSO from each dilution were added to 18.75 μL of assay buffer (MES, 50 mM (pH 5.5); EDTA, 2.5 mM; DTT, 2.5 mM and 10% DMSO) containing human cathepsin L (0.027 nM) in assay buffer solution. The assay solutions were mixed for 5-10 seconds on a shaker plate and incubated for 15 minutes at room temperature. Z-Leu-Arg-AMC (8 μM) in 6.25 μL of assay buffer was added to the assay solutions. Hydrolysis of the coumarin leaving group (AMC) was followed by spectrofluorometry (Exλ=360 nm; Emλ=460 nm) for 30 minutes. Percent of inhibition were calculated by fitting experimental values to standard mathematical model for dose response curve.

Cathepsin B Assay

Serial dilutions (⅓) from 500 μM down to 0.025 μM of test compounds were prepared in dimethyl sulfoxide (DMSO). Then 0.5 μL of DMSO from each dilution were added to 18.75 μL of assay buffer (MES, 50 mM (pH 5.5); EDTA, 2.5 mM; DTT, 2.5 mM and 10% DMSO) containing human cathepsin B (0.1 nM) in assay buffer solution. The assay solutions were mixed for 5-10 seconds on a shaker plate and incubated for 15 minutes at room temperature. Boc-Leu-Lys-Arg-AMC (8 μM) in 6.25 μL of assay buffer was added to the assay solutions. Hydrolysis of the coumarin leaving group (AMC) was followed by spectrofluorometry (Exλ=360 nm; Emλ=460 nm) for 30 minutes. Percent of inhibition were calculated by fitting experimental values to standard mathematical model for dose response curve.

Cathepsin S Assay

Serial dilutions (⅓) from 500 μM down to 0.025 μM of test compounds were prepared in dimethyl sulfoxide (DMSO). Then 0.5 μL of DMSO from each dilution were added to 18.75 μL of assay buffer (MES, 50 mM (pH 5.5); EDTA, 2.5 mM; DTT, 2.5 mM and 10% DMSO) containing human cathepsin S (0.66 nM) in assay buffer solution. The assay solutions were mixed for 5-10 seconds on a shaker plate and incubated for 15 minutes at room temperature. Z-Val-Val-Arg-AMC (8 μM) in 6.25 μL of assay buffer was added to the assay solutions. Hydrolysis of the coumarin leaving group (AMC) was followed by spectrofluorometry (Exλ=360 nm; Emλ=460 nm) for 20 minutes. Percent of inhibition were calculated by fitting experimental values to standard mathematical model for dose response curve.

Cathepsin F assay (hCat F)

Serial dilutions (⅓) from 500 μM down to 0.025 μM of test compounds were prepared in dimethyl sulfoxide (DMSO). Then 0.5 μL of DMSO from each dilution were added to 18.75 μL of assay buffer (MES, 50 mM (pH 5.5); EDTA, 2.5 mM; DTT, 2.5 mM and 10% DMSO) containing human cathepsin F (10 nM) in assay buffer solution. The assay solutions were mixed for 5-10 seconds on a shaker plate and incubated for 15 minutes at room temperature. Z-Phe-Arg-AMC (8 μM) in 6.25 μL of assay buffer was added to the assay solutions. Hydrolysis of the coumarin leaving group (AMC) was followed by spectrofluorometry (Exp, =360 nm; EmX=460 nm) for 20 minutes. Percent of inhibition were calculated by fitting experimental values to standard mathematical model for dose response curve.

Pharmacokinetics in Rats

Per Os (PO) Pharmacokinetics in Rats

Procedure:

The animals are housed, fed and cared for according to the Guidelines of the Canadian Council on Animal Care.

Male Sprague Dawley rats (250-400 g) are fasted overnight prior to each PO blood level study. The rats are placed in the restrainer one at a time and the box firmly secured. The zero blood sample is obtained by nicking a small (1 mm or less) piece off the tip of the tail. The tail is then stroked with a firm but gentle motion from the top to the bottom to milk out the blood. Approximately 0.5 mL of blood is collected into a heparinized vacutainer tube.

Compounds are prepared as required, in a standard dosing volume of 10 mL/kg, and administered orally by passing a 16 gauge, 3" gavaging needle into the esophagus.

Subsequent blood collections are taken in the same manner as the zero blood sample except that there is no need to nick the tail again. The tail is cleaned with a piece of gauze and milked/stroked as described above into the appropriately labeled tubes.

Immediately after sampling, blood is centrifuged, separated, the plasma put into clearly marked vials and stored in a freezer until analyzed.

Typical time points for determination of rat blood levels after PO dosing are:

0, 15 min, 30 min, 1 h, 2 h, 4 h, 6 h, 8 h, 24 h

After the 4 hr time point bleed, food is provided to the rats ad libitum. Water is provided at all times during the study.

Vehicles:

The following vehicles (with corresponding dose volumes) may be used in PO rat blood level determinations:

PEG 200/300/400 (0-60% in water): equal or less than 10 mL/kg

Methocel (0.5%-1.0% in water): equal or less than 10 mL/kg

Tween 80 (1-10% in water): equal or less than 10 mL/kg

Compounds for PO blood levels can be in suspension form. For better homogeneity, the suspension can be placed in a sonicator for approximately 5 minutes.

For analysis, aliquots are diluted with 1.2 to 1.5 volumes of acetonitrile optionally containing an internal standard and centrifuged to remove protein precipitate. The supernatant is injected directly onto a C-18 HPLC column with mass spectrometry (MS) or ultra-violet absorbance (UV) or fluorescence (Fluo) detection. Quantization is done relative to a standard curve prepared using clean blood samples spiked with a known quantities of drug in acetonitrile optionally containing an internal standard. Additional acetonitrile optionally containing internal standard is added to amount 1.2 to 1.5 volumes of the initial blood amount to correspond to what was done in the case of the samples. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

and $$AUC = (C1 + C2)^* (T2 - T1)/2$$

where C is the measured concentration by MS or UV or Fluo at a given time T

Intravenous Pharmacokinetics in Rats

Procedure:

The animals are housed, fed and cared for according to the Guidelines of the Canadian Council on Animal Care.

Male Sprague Dawley (325-375 g) non-fasted rats are used in theses studies.

The compound is prepared as required, in a standard dosing volume of 1 mL/kg.

Dosing of the conscious rats for intravenous administration is done via the jugular vein using a 25 gauge needle. This constitutes the zero time point.

The 5 min bleed is taken by nicking a piece (1-2 mm) off the tip of the tail. The tail is then stroked with a firm but gentle motion from the top of the tail to the bottom to milk the blood out of the tail. Approximately 0.5 mL of blood is collected into a heparinized collection vial. Subsequent bleeds are taken in the same fashion, except that there is no need to nick the tail again. The tail is cleaned with a piece of gauze and bled, as described above, into the appropriate labeled tubes.

Typical time points for determination of rat blood levels after I.V. dosing are either:
  0, 5 min, 15 min, 30 min, 1 h, 2 h, 4 h, 6 h
  or 0, 5 min, 30 min, 1 h, 2 h, 4 h, 6 h, 8 h, 24 h Vehicles:

The following vehicles may be used in IV rat blood level determinations:

Dextrose: 1 mL/kg

Moleculosol 25%: 1 mL/kg

DMSO (dimethylsulfoxide): Restricted 10% of the dose volume up to 0.1 mL per kilogram of animal PEG 200: Not more than 80% mixed with 20% sterile water—1 mL/kg With Dextrose, either sodium bicarbonate can be added if the solution is cloudy.

For analysis, aliquots are diluted with 1.2 to 1.5 volumes of acetonitrile optionally containing an internal standard and centrifuged to remove protein precipitate. The supernatant is injected directly onto a C-18 HPLC column with mass spectrometry (MS) or ultra-violet absorbance (UV) or fluorescence (Fluo) detection. Quantization is done relative to a standard curve prepared using clean blood samples spiked with a known quantities of drug in acetonitrile optionally containing an internal standard. Additional acetonitrile optionally containing internal standard is added to amount 1.2 to 1.5 volumes of the initial blood amount to correspond to what was done in the case of the samples. Bioavailability (F) is assessed by comparing area under the curve (AUC) i.v. versus p.o.

$$F = \frac{AUCpo}{AUCiv} \times \frac{DOSEiv}{DOSEpo} \times 100\%$$

and $$AUC = (C1 + C2)^* (T2 - T1)/2$$

where C is the measured concentration by MS or UV or Fluo at a given time T.

Hepatocyte Incubations

For rat hepatocyte incubations, $1 \times 10^6$ cells diluted in 0.5 mL of Krebs-Henseleit buffer were first prepared at 37° C. for 20 min under 95%:5% $O_2$:$CO_2$ (BOC gases: Montreal, Canada) in a 48-well plate, and the 5 μL of a 10 mM solution of compound dissolved in acetonitrile were added to each well to a final concentration of 50 μM. After 2 h of incubation at 37° C. under 95%:5% $O_2$:$CO_2$ atmosphere, one volume of acetonitrile was added in each well. A quenched incubation spiked with the parent compound and a blank were also prepared as controls. Once transferred, samples were centrifuged for 10 min at 14,000 rpm using an Eppendorf 5415C centrifuge (Hamburg, Germany) and the supernatant used for LC/UV/MS analysis.

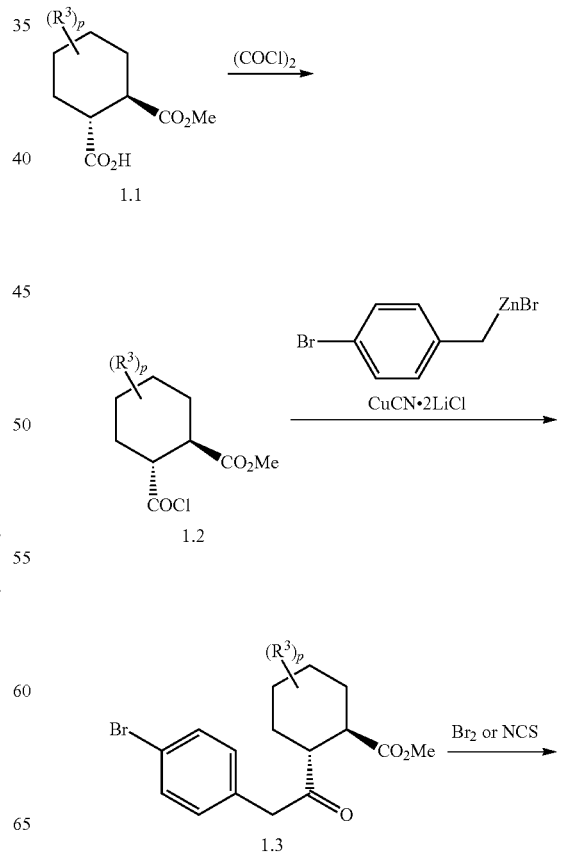

SCHEME 1

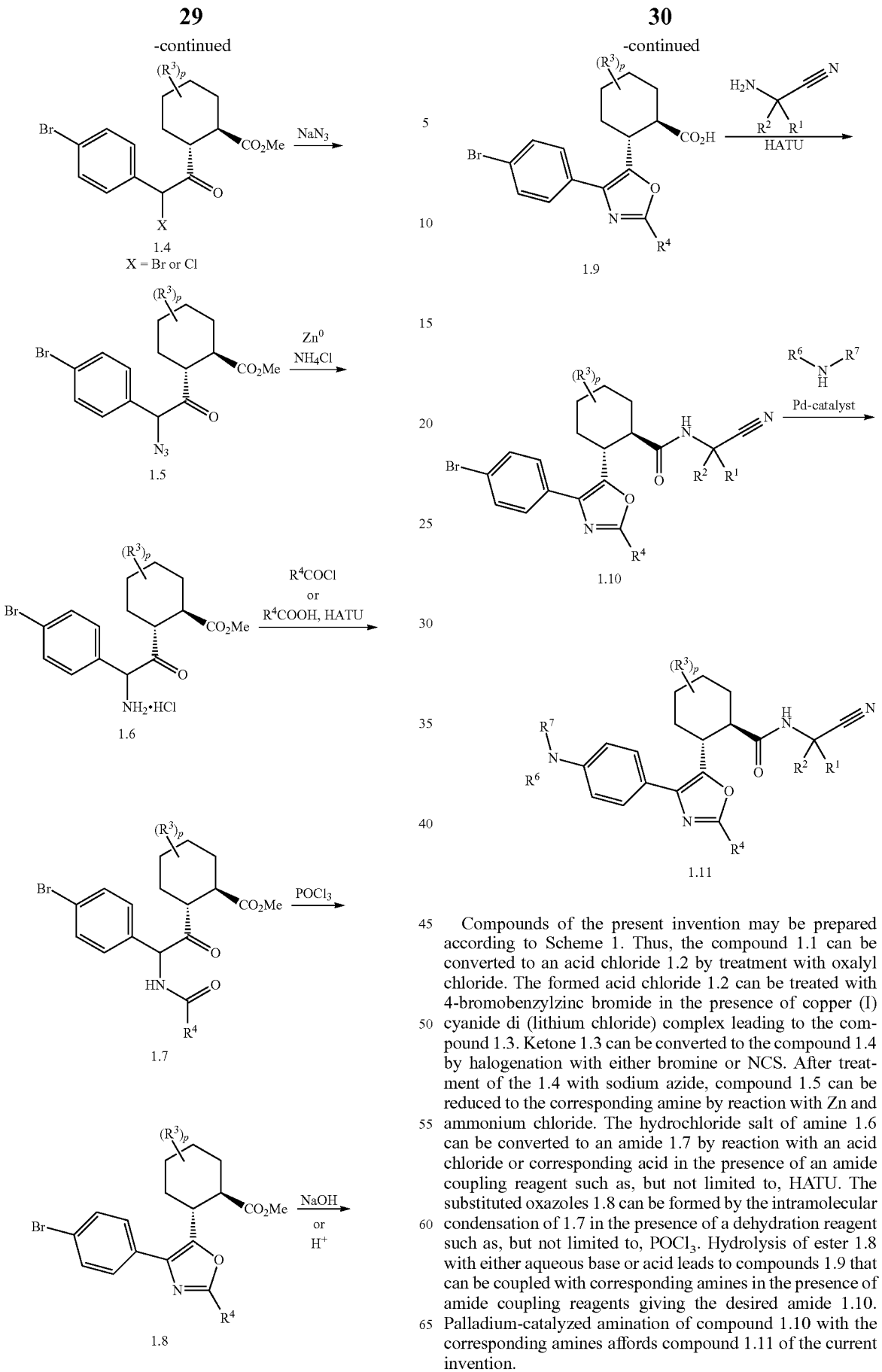

Compounds of the present invention may be prepared according to Scheme 1. Thus, the compound 1.1 can be converted to an acid chloride 1.2 by treatment with oxalyl chloride. The formed acid chloride 1.2 can be treated with 4-bromobenzylzinc bromide in the presence of copper (I) cyanide di (lithium chloride) complex leading to the compound 1.3. Ketone 1.3 can be converted to the compound 1.4 by halogenation with either bromine or NCS. After treatment of the 1.4 with sodium azide, compound 1.5 can be reduced to the corresponding amine by reaction with Zn and ammonium chloride. The hydrochloride salt of amine 1.6 can be converted to an amide 1.7 by reaction with an acid chloride or corresponding acid in the presence of an amide coupling reagent such as, but not limited to, HATU. The substituted oxazoles 1.8 can be formed by the intramolecular condensation of 1.7 in the presence of a dehydration reagent such as, but not limited to, $POCl_3$. Hydrolysis of ester 1.8 with either aqueous base or acid leads to compounds 1.9 that can be coupled with corresponding amines in the presence of amide coupling reagents giving the desired amide 1.10. Palladium-catalyzed amination of compound 1.10 with the corresponding amines affords compound 1.11 of the current invention.

SCHEME 2

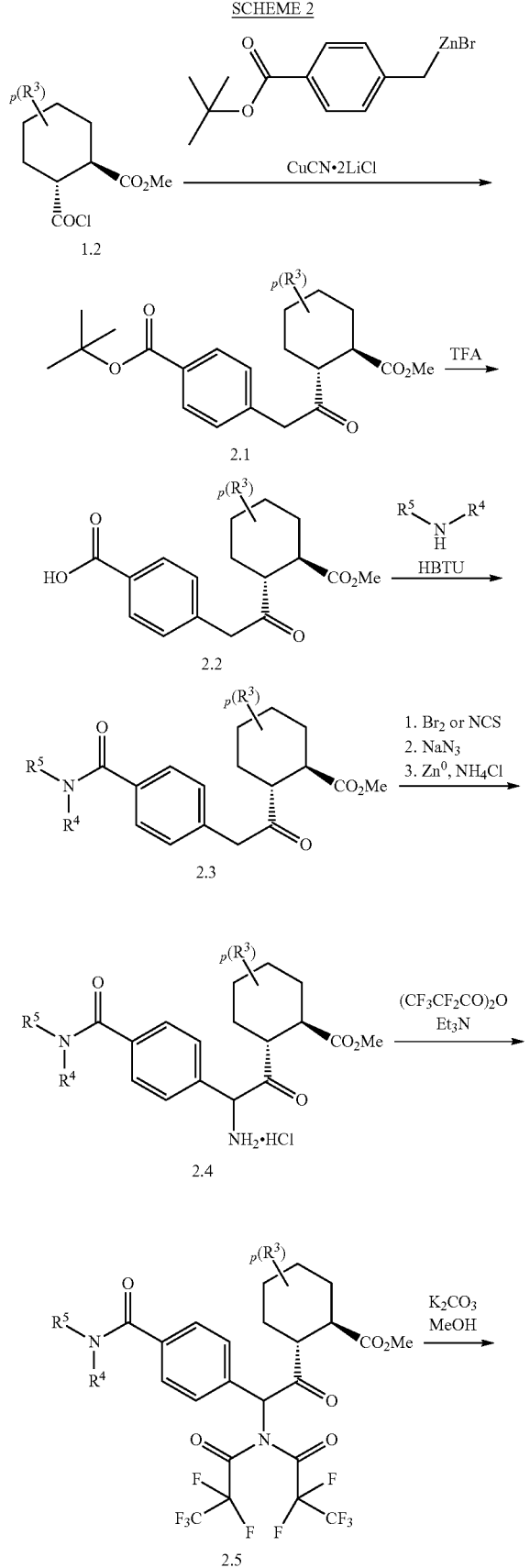

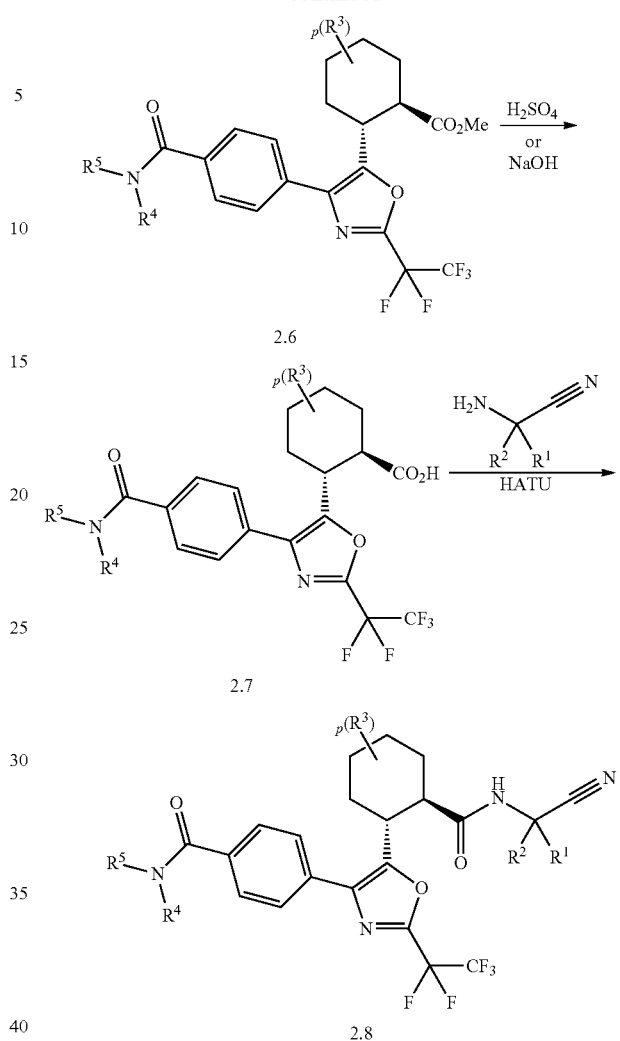

Compounds of the current invention may also be prepared according to Scheme 2. The reaction of an acid chloride 1.2 with (4-(tert-butoxycarbonyl)benzyl) zinc (II) bromide in the presence of copper (I) cyanide di(lithium chloride) complex leads to the compound 2.1. Hydrolysis of the tert-butyl ester with TFA affords benzoic acid derivative 2.2 that is converted to an amide 2.3 by reaction with corresponding amines in the presence of an amide coupling reagent such as, but not limited to, HBTU. An amide 2.3 is converted to compound 2.4 by halogenation of the benzylic position with either bromine or NCS followed by substitution with sodium azide, then reduction of the azide to the corresponding amine with Zn and ammonium chloride. Amine 2.4 is converted to a bis-amide 2.5 by reaction with pentafluoropropanoic anhydride. Partial deprotection by potassium carbonate in methanol leads to the substituted oxazole 2.6. Hydrolysis of the ester functionality with either aqueous base or acid leads to acid 2.7 that can be coupled with amines in the presence of an amide coupling reagent such as, but not limited to, HATU giving the desired compound 2.8 of the current invention.

SCHEME 3

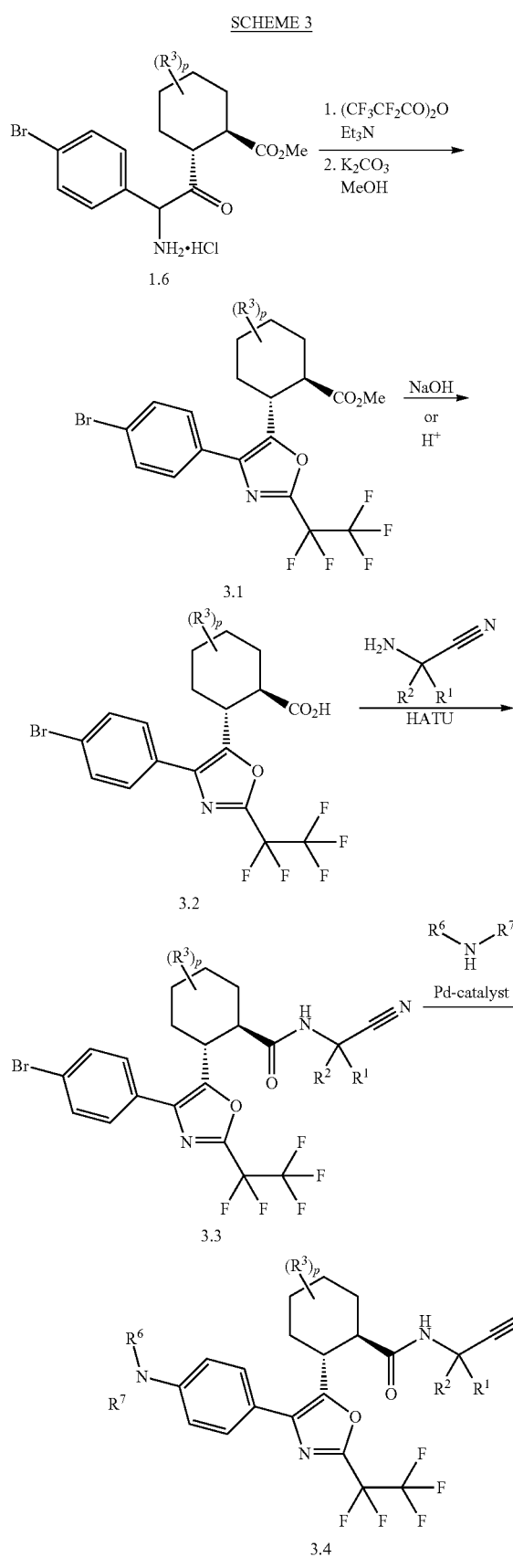

Compounds of the current invention may also be prepared according to Scheme 3. The hydrochloride salt of amine 1.6 is converted to a bis-pentafluoropropyl amide by reaction with pentafluoropropanoic anhydride followed by partial deprotection with potassium carbonate in methanol giving a substituted oxazole 3.1. Hydrolysis of the ester functionality with either aqueous base or acid leads to compound 3.2 that can be coupled with amines in the presence of an amide coupling reagent such as, but not limited to, HATU, giving an amide 3.3. Palladium-catalyzed amination of bromide 3.3 with the corresponding amines affords compound 3.4 of the current invention.

SCHEME 4

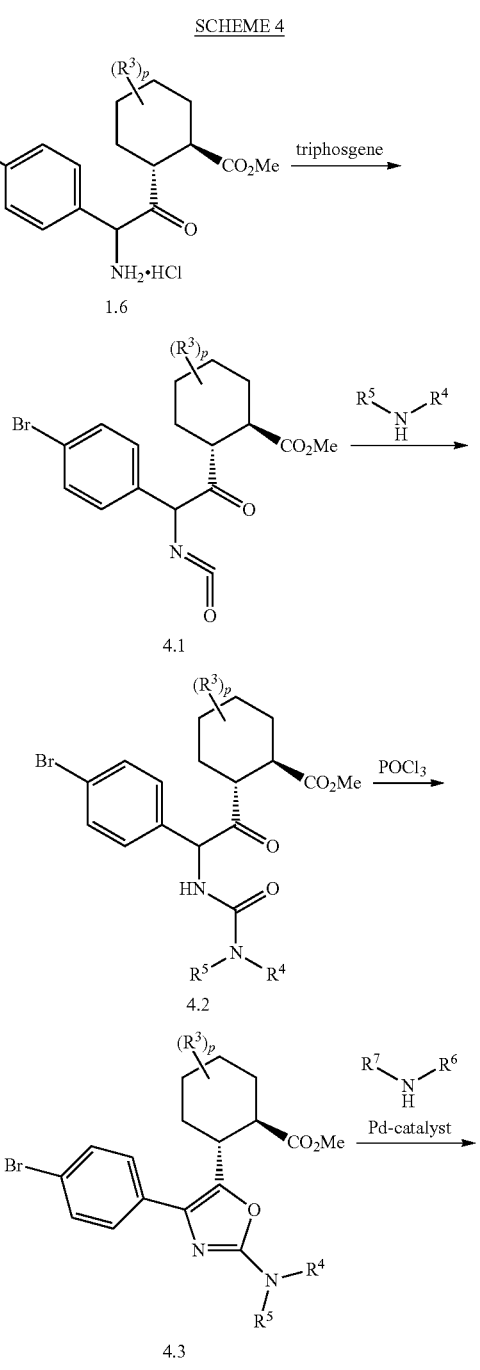

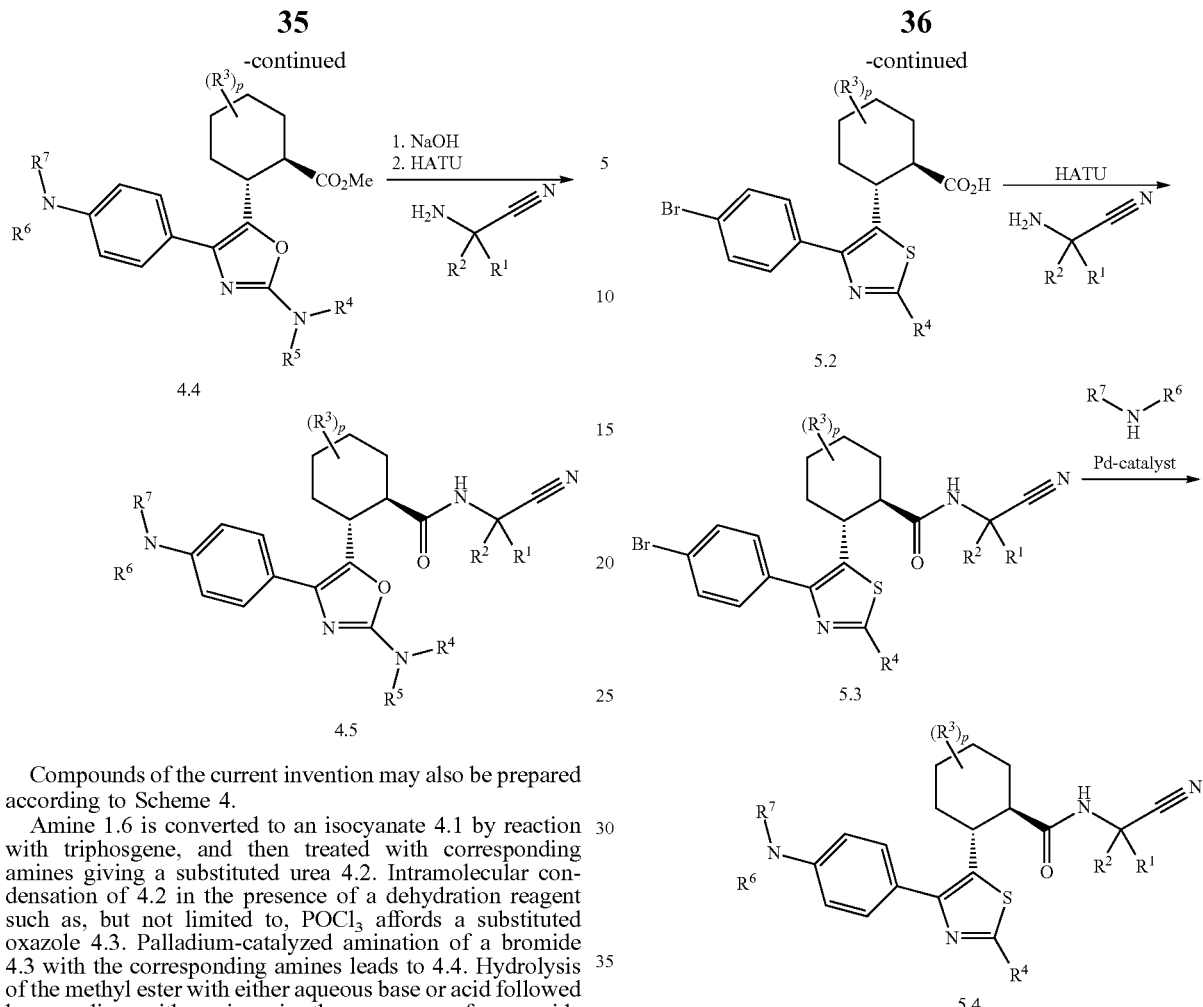

Compounds of the current invention may also be prepared according to Scheme 4.

Amine 1.6 is converted to an isocyanate 4.1 by reaction with triphosgene, and then treated with corresponding amines giving a substituted urea 4.2. Intramolecular condensation of 4.2 in the presence of a dehydration reagent such as, but not limited to, POCl$_3$ affords a substituted oxazole 4.3. Palladium-catalyzed amination of a bromide 4.3 with the corresponding amines leads to 4.4. Hydrolysis of the methyl ester with either aqueous base or acid followed by coupling with amines in the presence of an amide coupling reagent such as, but not limited to, HATU, affords compound 4.5 of the current invention.

SCHEME 5

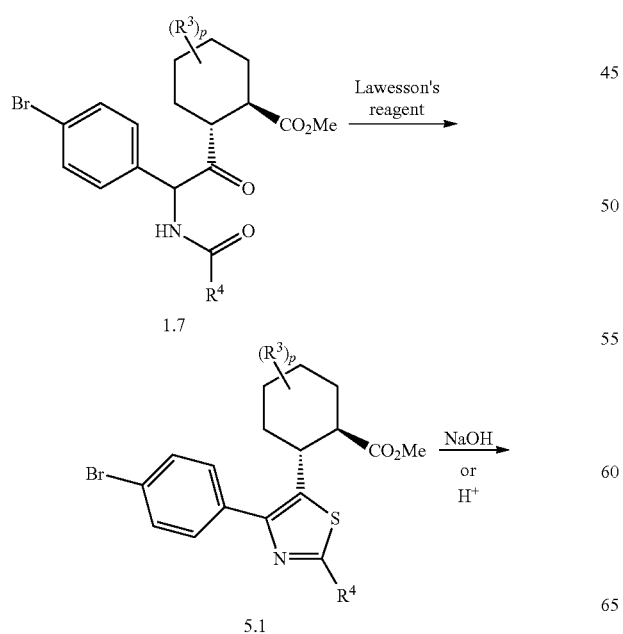

Compounds of the present invention may also be prepared according to Scheme 5. Compound 1.7 can be treated with Lawesson's reagent giving the desired substituted thiazole 5.1. Hydrolysis of the methyl ester of 5.1 with either aqueous base or acid leads to carboxylic acid 5.2 that can be coupled with corresponding amines in the presence of the amide coupling reagent such as, but not limited to, HATU. Palladium-catalyzed amination of bromide 5.3 with the corresponding amines affords compound 5.4 of the current invention.

The following examples describe the synthesis of selected compounds of the current invention:

SYNTHESIS OF INTERMEDIATES

Intermediate 1

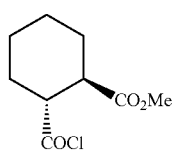

(1R,2R)-Methyl 2-(chlorocarbonyl)cyclohexanecarboxylate

Step A: (1R,2R)-2-(methoxycarbonyl)cyclohexanecarboxylic acid

This compound can be prepared from (1R,2S)-dimethyl cyclohex-4-ene-1,2-dicarboxylate following a similar procedure as described in *J. Am. Chem. SOC.* 1995, 117, 10905-10913 and in HELVETICA CHIMICA ACTA—Vol. 70 (1987), p. 142.

Step B: (1R,2R)-Methyl 2-(chlorocarbonyl)cyclohexanecarboxylate

To a solution of (1R,2R)-2-(methoxycarbonyl)cyclohexanecarboxylic acid (1.99 g, 10.69 mmol) in toluene (5 mL) was added oxalyl chloride (1.424 g, 11.22 mmol) and stirred at rt for 18 h. Bubble nitrogen gas through the reaction mixture for 20 min and then concentrate to give a colorless liquid which was used without further purification.

Intermediate 2

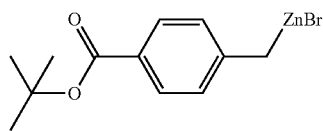

(4-(tert-Butoxycarbonyl)benzyl)zinc(II) bromide

This compound was prepared following a similar procedure as described in *Org. Lett.*, 2008, 6, 1107.

Intermediate 3

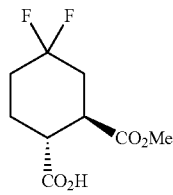

(1R,2R)-4,4-difluoro-2-(methoxycarbonyl)cyclohexanecarboxylic acid

Step A: (1R,2R)-dimethyl 4-oxocyclohexane-1,2-dicarboxylate

Racemic dimethyl 4-oxocyclohexane-1,2-dicarboxylate (660 g) was charged into 11 L of 50 mM phosphate buffer, pH=6.8. Esterase K310-903 (25 mL) was added to the solution and the resulting mixture was stirred at 30° C. overnight. SFC shows the reaction was done. 1N NaOH was added to pH=7 and the solution was extracted with MTBE (4×8 L). The combined organic fraction was washed with brine, dry (Na$_2$SO$_4$), and filtered. Removal of the solvent by evaporation gave 225 g (34% yield, 98% ee) of (1R,2R)-dimethyl 4-oxocyclohexane-1,2-dicarboxylate as oil.

Step B: (1R,2R)-dimethyl 4,4-difluorocyclohexane-1,2-dicarboxylate

To a solution of Et$_3$N.3HF (224 g, 1.38 mol) in DCE (2.8 L) was added DAST.BF$_3$ (630 g, 2.74 mol). The resultant suspension was stirred for 10 min and then (1R,2R)-dimethyl 4-oxocyclohexane-1,2-dicarboxylate (280 g, 1.31 mol) was added. The mixture was heated at 55° C. overnight. The reaction mixture was poured into sat. NaHCO$_3$ (5.6 L) and then extracted with DCM (2 L×3). The organic layer was dried (Na$_2$SO$_4$), concentrated and purified by flash chromatography (petroleum ether/EtOAc=15:1) to afford 260 g of pale yellow oil. The yellow oil was dissolved in 4 L DCM. 3 L of 5% KMnO$_4$ aq. solution was added. The mixture was stirred at 23° C. overnight. The organic layer was separated, washed with 3 L of 5% KMnO$_4$ for another 3 hour. The organic layer was separated, washed with brine, dried (Na$_2$SO$_4$), and concentrated to dryness giving (1R,2R)-dimethyl 4,4-difluorocyclohexane-1,2-dicarboxylate as a white solid (230 g, 74.5%). $^1$H NMR 400 MHz (CDCl$_3$): δ 8.19-8.22 (m, 2H), 7.83 (d, J=8.1 Hz, 1H), 7.65-7.69 (m, 1H), 7.52-7.55 (m, 2H), 7.37 (s, 1H), 7.22 (dd, J=8.1 Hz, J=2.0 Hz, 1H), 3.17-3.20 (m, 2H), 2.73-2.76 (m, 2H).

Step C: (1R,2R)-4,4-difluoro-2-(methoxycarbonyl) cyclohexanecarboxylic acid

Cal B enzyme (26.5 mL) was dissolved in 0.1M phosphate buffer at pH 7.0 (6.8 L). (1R,2R)-dimethyl 4,4-difluorocyclohexane-1,2-dicarboxylate (100 g) in DMSO (300 mL) was added into the reaction mixture and stirred at 25° C. for 6 hours. The solution was washed with brine (1 L) and extracted with MTBE (3 L*4). The combined organic layer was washed with brine, dried (Na$_2$SO$_4$), filtered, and concentrated to dryness giving (1R,2R)-4,4-difluoro-2-(methoxycarbonyl)cyclohexanecarboxylic acid as a white solid (90 g, 94%). $^1$H NMR 400 MHz CDCl$_3$ δ 3.65 (S, 3H), 2.93 (m, 1H), 2.68 (m, 1H), 2.39 (m, 1H), 2.12 (m, 2H), 1.74 (m, 3H).

Intermediate 4

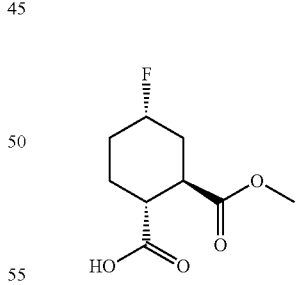

(1R,2R,4S)-4-fluoro-2-(methoxycarbonyl)cyclohexanecarboxylic acid

Step A: (7R,8R)-dimethyl 1,4-dioxaspiro[4.5]decane-7,8-dicarboxylate

The solution of (1R,2R)-dimethyl 4-oxocyclohexane-1,2-dicarboxylate (300 g, 1.4 mol) in toluene (6 L) was added ethylene glycol (117 ml, 2.1 mol) and TsOH (5.29 g, 0.028 mol). The resulted solution was refluxed for 6 hours. The reaction mixture was cool to 23° C. and washed with saturated NaHCO3 (2×5 L) and water once. The organic phase was concentrated giving (7R,8R)-dimethyl 1,4-dioxaspiro[4.5]decane-7,8-dicarboxylate (330 g, 91.2%) as a yellow oil.

Step B: (7R,8R)-7-(methoxycarbonyl)-1,4-dioxaspiro[4.5]decane-8-carboxylic acid

In a 50 L round buttom flask equipped with overhead stirring and pH Stat, NZL-102 enzyme (60 g (5 g/L)) was dissolved in 24 L of phosphate buffer pH 7. (7R,8R)-Dimethyl 1,4-dioxaspiro[4.5]decane-7,8-dicarboxylate (300 g, 1.16 mol) in 300 mL of DMSO solution was added dropwise and aged at 23° C. overnight. The reaction mixtures was dissolved in 3:1 EtOAc: IPA, extracted and the organic layer was washed with brine, dried (Na$_2$SO$_4$), filtered, and concentrated giving (7R,8R)-7-(methoxycarbonyl)-1,4-dioxaspiro[4.5]decane-8-carboxylic acid (220 g, 77.5%) as a yellow solid.

Step C: (7R,8R)-8-benzyl 7-methyl 1,4-dioxaspiro[4.5]decane-7,8-dicarboxylate

To the solution of (7R,8R)-7-(methoxycarbonyl)-1,4-dioxaspiro[4.5]decane-8-carboxylic acid (2.9 g, 11.87 mmol) in DMF (20 ml) was added K$_2$CO$_3$ (2.461 g, 17.81 mmol) and then (bromomethyl)benzene (3.05 g, 17.81 mmol) and KI (394 mg, 2.375 mmol). The resulting suspension was stirred at RT overnight. The reaction mixture was extracted with EtOAc and purified by flash chromatography on silica gel giving 2.95 g (74%) of (7R,8R)-8-benzyl 7-methyl 1,4-dioxaspiro[4.5]decane-7,8-dicarboxylate as oil.

Step D: (1R,2R)-1-benzyl 2-methyl 4-oxocyclohexane-1,2-dicarboxylate

To the solution of (7R,8R)-8-benzyl 7-methyl 1,4-dioxaspiro[4.5]decane-7,8-dicarboxylate (2.95 g, 8.82 mmol) in acetone (40 ml) was added 1N HCl (40 mL) and the resulting mixture was heated at 60° C. for 1 hour. The reaction mixture was diluted with EtOAc/water, organic phase was dried (Na$_2$SO$_4$), filtered, and concentrated. The residue was purified by flash chromatography on silica gel giving 2.56 g (100%) of (1R,2R)-1-benzyl 2-methyl 4-oxocyclohexane-1,2-dicarboxylate as a clear oil.

Step E: (1R,2R,4R)-1-benzyl 2-methyl 4-hydroxycyclohexane-1,2-dicarboxylate

The solution of (1R,2R)-1-benzyl 2-methyl 4-oxocyclohexane-1,2-dicarboxylate (2.6 g, 8.96 mmol) in THF (45 ml) was cooled with salt ice bath (~−5° C.) and NaBH$_4$ (0.678 g, 17.91 mmol) was added. The resulted solution was stirred at 0° C. for 2 hours. The reaction mixture was quenched carefully with water and EtOAc. The organic phase was dried (Na$_2$SO$_4$), filtered, and concentrated. The residue was purified by flash chromatography on silica gel giving 2.05 g (78%) of the desired alcohol (1R,2R,4R)-1-benzyl 2-methyl 4-hydroxycyclohexane-1,2-dicarboxylate.

Step F: (1R,2R,4S)-1-benzyl 2-methyl 4-fluorocyclohexane-1,2-dicarboxylate

To a solution of morpholinodifluorosulfinium tetrafluoroborate (1.704 g, 7.01 mmol) in DCM (4 mL) was added triethylamine trihydrofluoride (2.261 g, 14.03 mmol). The resulting suspension was stirred for 10 min at RT and cooled to −78° C. (1R,2R,4R)-1-Benzyl 2-methyl 4-hydroxycyclohexane-1,2-dicarboxylate (2.05 g, 7.01 mmol) solution in DCM (10 mL) was added at with internal temp kept <−40° C. The mixture was stirred at −40° C. for ~30 min. The reaction was quenched at low temperature with water. The isolated organic phase was washed with water, brine, dried (Na$_2$SO$_4$), filtered, and concentrated. The residue was purified by flash chromatography on silica gel (ISCO column, 12 g silica gel, 0-20% EtOAc/heptane) giving 525 mg (25.4%) of (1R,2R,4S)-1-benzyl 2-methyl 4-fluorocyclohexane-1,2-dicarboxylate as a colorless oil.

Step G: (1R,2R,4S)-4-fluoro-2-(methoxycarbonyl)cyclohexanecarboxylic acid

The suspension of Pd/C (10%) (122 mg, 0.115 mmol) in EtOAc (1 ml) was added to (1R,2R,4S)-1-benzyl 2-methyl 4-fluorocyclohexane-1,2-dicarboxylate (675 mg, 2.293 mmol). The resulting suspension was stirred at 1 atm H$_2$ balloon for 5 hour. The reaction mixture was filtered and concentrated to give 770 mg (100%) of the desired (1R,2R,4S)-4-fluoro-2-(methoxycarbonyl)cyclohexanecarboxylic acid as a colorless oil.

Intermediate 5

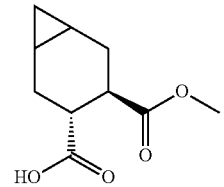

(3R,4R)-4-(methoxycarbonyl)bicyclo[4.1.0]heptane-3-carboxylic acid

Step A: (1R,2S)-1-Benzyl 2-methyl cyclohex-4-ene-1,2-dicarboxylate

Into a 50-mL round-bottom flask, was placed a solution of (1R,6S)-6-(methoxycarbonyl)cyclohex-3-enecarboxylic acid (2.40 g, 13.0 mmol, 1.00 equiv) in N,N-dimethylformamide (30 mL). To this solution was added potassium carbonate (3.59 g, 26.0 mmol, 2.00 equiv). This was followed by the addition of benzyl bromide (3.34 g, 19.5 mmol, 1.50 equiv) dropwise with stirring at ambient temperature. The reaction mixture was stirred for 16 h at ambient temperature. The resulting mixture was diluted with brine (50 mL) and extracted with ethyl acetate (3×50 mL). The combined organic layers was dried over anhydrous sodium sulfate and filtered. The filtrate was concentrated under vacuum. The residue was applied onto silica gel column chromatography with ethyl acetate/petroleum ether (1:30-1:15). This resulted in 3.20 g (90%) of (1R,2S)-1-benzyl 2-methyl cyclohex-4-ene-1,2-dicarboxylate as a colorless oil: $^1$H NMR (300 MHz, CDCl$_3$) δ ppm 7.43-7.30 (m, 5H), 5.69 (s, 2H), 5.14 (s, 2H), 3.58 (s, 3H), 3.14-3.05 (m, 2H), 2.64-2.53 (m, 2H), 2.42-2.34 (m, 2H); MS (ES, m/z): 275.1 (M+1).

Step B: (3R,4S)-3-Benzyl 4-methyl bicyclo[4.1.0]heptane-3,4-dicarboxylate

Into a 500-mL 3-necked round-bottom flask purged and maintained with an inert atmosphere of nitrogen, was placed a solution of diethylzinc (1 M in hexane, 46.8 mL, 4.00 equiv) in anhydrous dichloromethane (150 mL). This was followed by the addition of trifluoroacetic acid (5.34 g, 46.8 mmol, 4.00 equiv) dropwise with stirring at 0° C. To this solution was added diiodomethane (12.5 g, 46.8 mmol, 4.00 equiv) dropwise with stirring at 0° C. and the mixture was stirred for 15 min at 0° C. Then a solution of (1R,2S)-1-benzyl 2-methyl cyclohex-4-ene-1,2-dicarboxylate (3.20 g, 11.7 mmol, 1.00 equiv) in anhydrous dichloromethane (50 mL) was added dropwise with stirring at 0° C. The reaction solution was stirred and warmed slowly to ambient temperature for 16 h. The reaction solution was quenched by the addition of water (300 mL) and extracted with dichloromethane (3×200 mL). The combined organic layers was dried over anhydrous sodium sulfate and filtered. The filtrate was concentrated under vacuum. The residue was applied onto silica gel column chromatography with ethyl acetate/petroleum ether (1:20-1:10). This resulted in 3.10 g (92%) of (3R,4S)-3-benzyl 4-methyl bicyclo[4.1.0]heptane-3,4-dicarboxylate as a light yellow oil: MS (ES, m/z): 289.0 (M+1).

Step C: (3R,4S)-4-(Methoxycarbonyl)bicyclo[4.1.0]heptane-3-carboxylic acid

Into a 250-mL round-bottom flask was placed a solution of (3R,4S)-3-benzyl 4-methyl bicyclo[4.1.0]heptane-3,4-dicarboxylate (3.10 g, 10.8 mmol, 1.00 equiv) in methanol (100 mL), followed by the addition of palladium 10% on carbon (0.300 g, wetted with ca. 55% water). The reaction mixture was degassed with hydrogen for 3 times and stirred under hydrogen balloon for 16 h at ambient temperature. The solid was filtered out. The filtrate was concentrated under vacuum. This resulted in 2.10 g (89%) of crude (3R,4S)-4-(methoxycarbonyl)bicyclo[4.1.0]heptane-3-carboxylic acid as a colorless oil, which was used directly in next step without further purification: MS (ES, m/z): 199.2 (M+1).

Step D: (3R,4R)-4-(Methoxycarbonyl)bicyclo[4.1.0]heptane-3-carboxylic acid

Into a 250-mL 3-necked round-bottom flask purged and maintained with an inert atmosphere of nitrogen, was placed anhydrous methanol (130 mL). This was followed by the addition of sodium (2.00 g, 87.0 mmol, 8.21 equiv) in portions at 0° C. The resulting mixture was stirred for 30 min at ambient temperature until sodium disappeared. To this solution was added a solution of (3R,4S)-4-(methoxycarbonyl)bicyclo[4.1.0]heptane-3-carboxylic acid (2.10 g, 10.6 mmol, 1.00 equiv) in methanol (20 mL). The resulting solution was refluxed for 16 h. The reaction mixture was cooled to 0° C. The pH value was adjusted to 4 with aqueous hydrochloric acid solution (1 M). The resulting mixture was extracted with ethyl acetate (3×200 mL). The combined organic layers was dried over anhydrous sodium sulfate and filtered. The filtrate was concentrated under vacuum. The residue was applied onto silica gel column chromatography with ethyl acetate/petroleum ether (1:5-1:3). This resulted in 1.40 g (60%) of (3R,4R)-4-(methoxycarbonyl)bicyclo[4.1.0]heptane-3-carboxylic acid as a light yellow oil: $^1$H NMR (400 MHz, DMSO-d$_6$) δ ppm 12.30-12.10 (brs, 1H), 3.55 (s, 3H), 2.36-2.25 (m, 3H), 2.12-2.04 (m, 1H), 1.79-1.74 (m, 1H), 1.36-1.34 (m, 1H), 0.99-0.95 (m, 2H), 0.63-0.60 (m, 1H), 0.10-0.08 (m, 1H); MS (ES, m/z): 199.2 (M+1).

Example 1

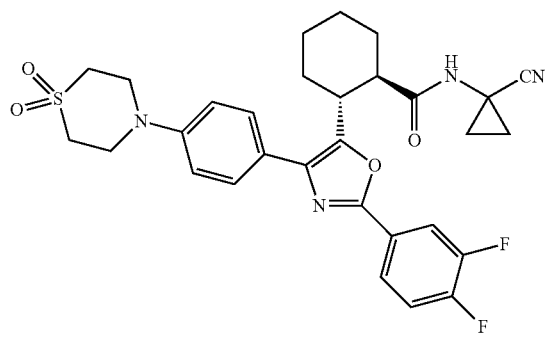 [SMILES: N#CC1(NC(=O)[C@@H]2CCCC[C@H]2c2oc(-c3ccc(F)c(F)c3)nc2-c2ccc(N3CCS(=O)(=O)CC3)cc2)CC1]

(1R,2R)—N-(1-Cyanocyclopropyl)-2-(2-(3,4-difluorophenyl)-4-(4-(1,1-dioxidothiomorpholino)phenyl)oxazol-5-yl)cyclohexanecarboxamide (Compound 1)

Step A: (1R,2R)-Methyl 2-(2-(4-bromophenyl)acetyl)cyclohexanecarboxylate

Preparation of 1 M CuCN.2LiCl: A mixture of CuCN (1.792 g, 20 mmol) and LiCl (1.696 g, 40 mmol) was dried under vacuum at 140° C. for 5 h. After cooling the mixture down to rt, 20 mL THF was added and stirred at rt overnight to give a light green solution.

To a solution of CuCN.2LiCl (1 M, 12.82 mL) in THF at −25° C. was added a solution of 4-bromobenzylzinc bromide (0.5 M, 25.6 mL) in THF dropwise and stirred for 15 min. A solution of (1R,2R)-methyl 2-(chlorocarbonyl)cyclohexanecarboxylate (2.187 g, 10.69 mmol) in THF (7 mL) was added dropwise and the resulting mixture was stirred for 5 min at −25° C., for 15 min at 0° C. and 4 h at rt. Partition the reaction mixture between EtOAc and aqueous NH$_4$OH-aqueous saturated NH$_4$Cl (1:2 v/v, 200 mL). Aqueous layer was extracted with EtOAc (3×). Combined organic solutions were dried over Na$_2$SO$_4$, filtered and concentrated. Purified by flash chromatography (40 g SiO$_2$) using a linear gradient of 3 to 15% EtOAc in hexanes to give a white solid (2.45 g, 67%).

Step B: (1R,2R)-Methyl 2-(2-(4-bromophenyl)-2-chloroacetyl)cyclohexanecarboxylate A solution of (1R,2R)-methyl 2-(2-(4-bromophenyl)acetyl)cyclohexanecarboxylate (5.9 g, 17.39 mmol) and N-chlorosuccinimide (2.79 g, 20.87 mmol) in dry DMF (25 mL) was heated at 65° C. for 1 h and then cooled to rt. Partition between saturated aqueous Na$_2$S$_2$O$_3$ solution and EtOAc. Aqueous layer was extracted with EtOAc (3×). Combined organic solutions were washed with brine, dried over Na$_2$SO$_4$, filtered and concentrated. Purified by flash chromatography (120 g SiO$_2$) using a linear gradient of 3 to 15% EtOAc in hexanes to give a white solid (5.83 g, 90%).

Step C: (1R,2R)-Methyl 2-(2-azido-2-(4-bromophenyl)acetyl)cyclohexanecarboxylate To a solution of (1R,2R)-methyl 2-(2-(4-bromophenyl)-2-chloroacetyl)cyclohexanecarboxylate (4.794 g, 12.83 mmol) in DMSO (30 mL) is added sodium azide (1.001 g, 15.4 mmol). The resulting mixture was stirred at rt for 15 min, diluted with water and extracted with EtOAc (3×). Combined organic solutions were washed with brine, dried over $Na_2SO_4$, filtered and concentrated to give a light yellow viscous liquid which was used without further purification.

Step D: (1R,2R)-Methyl 2-(2-amino-2-(4-bromophenyl)acetyl)cyclohexanecarboxylate hydrochloride To a mixture of (1R,2R)-methyl 2-(2-azido-2-(4-bromophenyl)acetyl)cyclohexanecarboxylate (4.794 g, 12.61 mmol) and $NH_4Cl$ (1.686 g, 31.5 mmol) in EtOH (29 mL) was added $H_2O$ (10 mL) followed by zinc dust (1.154 g, 17.65 mmol). Concentrated after 1 h of stirring at rt. The residue was triturated with THF and filtered. The filtrate was then concentrated to give a light yellow foam which was used without further purification.

Step E: (1R,2R)-Methyl 2-(2-(4-bromophenyl)-2-(3,4-difluorobenzamido)acetyl)cyclohexanecarboxylate To a solution of (1R,2R)-methyl 2-(2-amino-2-(4-bromophenyl)acetyl)cyclohexanecarboxylate hydrochloride (157 mg, 0.402 mmol) in dichloromethane (3 mL) at 0° C. was added 3,4-difluorobenzoyl chloride (284 mg, 1.607 mmol) followed by Hunig's base (312 mg, 2.411 mmol). Stirred at 0° C. for 15 min and then concentrated. The residue was dissolved in DMSO and purified by reverse phase HPLC (Sunfire C18 30×150 mm column; 40 to 95% MeCN in water. 0.1% TFA modifier for MeCN and water) to give desired product as a colorless viscous liquid (77 mg, 39%).

Step F: (1R,2R)-Methyl 2-(4-(4-bromophenyl)-2-(3,4-difluorophenyl)oxazol-5-yl)cyclohexanecarboxylate A solution of (1R,2R)-methyl 2-(2-(4-bromophenyl)-2-(3,4-difluorobenzamido)acetyl)cyclohexanecarboxylate (77 mg, 0.156 mmol) in $POCl_3$ (3 mL) was heated at 100° C. for 10 h and at 80° C. for 60 h. The solution was concentrated and the resulting residue was dissolved in dichloromethane and cooled to 0° C. Saturated aqueous $NaHCO_3$ solution was added to the dichloromethane solution until the aqueous layer became basic. Layers were separated. Aqueous layer was extracted with dichloromethane (3×). Combined organic solutions were dried over $Na_2SO_4$, filtered and concentrated to give a wite solid which was used without further purification.

Step G: (1R,2R)-2-(4-(4-Bromophenyl)-2-(3,4-difluorophenyl)oxazol-5-yl)cyclohexanecarboxylic acid A suspension of (1R,2R)-methyl 2-(4-(4-bromophenyl)-2-(3,4-difluorophenyl)oxazol-5-yl)cyclohexanecarboxylate (74 mg, 0.155 mmol) in MeOH-THF (1:2, 1.8 mL) was treated with 1 N aqueous NaOH solution (0.621 mL) and stirred at 60° C. for 4 h. After cooling down to rt, 0.621 mL of 1 N aqueous HCl was added. The resulting solution was concentrated to a white solid which was used without further purification.

Step H: (1R,2R)-2-(4-(4-bromophenyl)-2-(3,4-difluorophenyl)oxazol-5-yl)-N-(1-cyanocyclopropyl) cyclohexanecarboxamide To a solution of (1R,2R)-2-(4-(4-bromophenyl)-2-(3,4-difluorophenyl)oxazol-5-yl)cyclohexanecarboxylic acid (72 mg, 0.156 mmol) and HATU (89 mg, 0.389 mmol) in DMF (1 mL) was added 1-cyanocyclopropanaminium chloride (46.2 mg, 0.389 mmol) followed by the addition of Hunig's base (101 mg, 0.779 mmol) and stirred at 40° C. overnight. The resulting solution was purified directly by reverse phase HPLC (Sunfire C18 30×150 mm column; 40 to 95% MeCN in water. 0.1% TFA modifier for MeCN and water) to give desired product as a white solid (32 mg, 39%).

Step I: (1R,2R)—N-(1-Cyanocyclopropyl)-2-(2-(3,4-difluorophenyl)-4-(4-(1,1-dioxidothiomorpholino)phenyl)oxazol-5-yl)cyclohexanecarboxamide (Compound 1)

To a mixture of (1R,2R)-2-(4-(4-bromophenyl)-2-(3,4-difluorophenyl)oxazol-5-yl)-N-(1-cyanocyclopropyl)cyclohexanecarboxamide (20 mg, 0.038 mmol), thiomorpholine 1,1-dioxide (15.4 mg, 0.114 mmol), chloro(2-dicyclohexylphosphino-2',4',6'-triisopropyl-1,1'-biphenyl)[2-(2-aminoethyl)phenyl]palladium(II) (2.81 mg, 0.004 mmol) and $K_3PO_4 \cdot H_2O$ (10.5 mg, 0.046 mmol) in a vial under an inert atmosphere was added THF (0.7 mL). The vial was sealed and heated at 100° C. for 5 h. Cooled to rt and concentrated. The residue was taken in DMSO, filtered and the filtrate was subjected to reverse phase HPLC purification (Sunfire C18 30×150 mm column; 30 to 95% MeCN in water. 0.1% TFA modifier for MeCN and water) which did not yield pure product. This impure product was then purified by flash chromatography (4 g $SiO_2$) using a linear gradient of 3 to 90% EtOAc in hexanes to give a white solid (5 mg, 23%). MS $[M+H]^+$ 581.1. $^1H$ NMR (400 MHz, $CDCl_3$) δ 7.88-7.78 (m, 2H), 7.66 (d, J=8.8 Hz, 2H), 7.31-7.27 (m, 1H), 6.99 (d, J=8.8 Hz, 2H), 5.67 (s, 1H), 3.95-3.92 (m, 4H), 3.35-3.24 (m, 1H), 3.14-3.12 (m, 4H), 2.48-2.44 (m, 1H), 2.25-1.64 (m, 6H), 1.48-1.26 (m, 4H), 0.79-0.62 (m, 2H).

Example 2

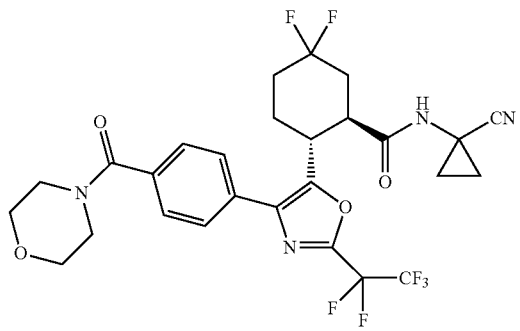 [SMILES: N#CC1(NC(=O)[C@@H]2CC(F)(F)CC[C@H]2c2oc(C(F)(F)C(F)(F)F)nc2-c2ccc(C(=O)N3CCOCC3)cc2)CC1]

(1R,2R)—N-(1-Cyanocyclopropyl)-5,5-difluoro-2-(4-(4-(morpholine-4-carbonyl)phenyl)-2-(perfluoroethyl)oxazol-5-yl)cyclohexanecarboxamide (Compound 2)

Step A: tert-Butyl 4-(2-((1R,2R)-4,4-diflouro-2-methoxycarbonyl)cyclohexyl)-2-oxoethyl)benzoate This compound was prepared from (1R,2R)-4,4-difluoro-2-(methoxycarbonyl)cyclohexanecarboxylic acid (INTERMEDIATE 3) through its acid chloride and (4-(tert-Butoxycarbonyl)benzyl)zinc(II) bromide (INTERMEDIATE 2) using a similar procedure as described in Step A of Example 1.

Step B: 4-(2-((1R,2R)-4,4-Difluoro-2-(methylcarbonyl)cyclohexyl)-2-oxoethyl)benzoic acid To a solution of tert-butyl 4-(2-((1R,2R)-4,4-difluoro-2-(methoxycarbonyl)cyclohexyl)-2-oxoethyl)benzoate (845 mg, 2.132 mmol) in dichloromethane (4 mL) was added TFA (5 mL). After stirring at 23° C. for 30 min, the reaction mixture was diluted with EtOAc, washed with water (2×) and brine (1×), dried over $Na_2SO_4$ and concentrated to give a white solid which was used without further purification.

Step C: (1R,2R)-Methyl 5,5-difluoro-2-(2-(4-(morpholine-4-carbonyl)phenyl)acetyl)cyclohexanecarboxylate To a solution of 4-(2-((1R,2R)-4,4-difluoro-2-(methoxycarbonyl)cyclohexyl)-2-oxoethyl)benzoic acid (725 mg, 2.13 mmol) and HBTU (1.212 g, 3.20 mmol) in DMF (3 mL) was added morpholine (1.3 g, 14.91 mmol). The resulting mixture was stirred at 23° C. for 1.5 h and then purified directly by reverse phase HPLC (Sunfire C18 30×150 mm column; 5 to 85% MeCN in water. 0.1% TFA modifier for MeCN and water) to give desired product as a colorless viscous liquid (434 mg, 50%).

Step D: (1R,2R)-Methyl 2-(2-bromo-2-(4-(morpholine-4-carbonyl)phenyl)acetyl)-5,5-difluorocyclohexanecarboxylate To a solution of (1R,2R)-methyl 5,5-difluoro-2-(2-(4-(morpholine-4-carbonyl)phenyl)acetyl)cyclohexanecarboxylate (434 mg, 1.06 mmol) in dichloromethane (24 mL) was added a solution of $Br_2$ (169 mg, 1.06 mmol) in dichloromethane (1 mL). The reaction mixture was stirred at 60° C. for 6 h and then cooled to rt and partitioned between saturated aqueous $Na_2S_2O_3$ and dichloromethane. Aqueous layer was extracted with dichloromethane (4×). Combined organic solutions were dried over $Na_2SO_4$ and concentrated to give a white foam which was used without further purification.

Step E: (1R,2R)-Methyl 2-(2-azido-2-(4-(morpholine-4-carbonyl)phenyl)acetyl)-5,5-difluorocyclohexanecarboxylate Solid sodium azide (48.5 mg, 0.746 mmol) was added to a solution of (1R,2R)-methyl 2-(2-bromo-2-(4-(morpholine-4-carbonyl)phenyl)acetyl)-5,5-difluorocyclohexanecarboxylate (331 mg, 0.678 mmol) in MeCN (5 mL). After stirring the reaction mixture at 60° C. for 30 min, 50 mg more sodium azide was added and continued stirring at 60° C. for 1 h. Cooled to 23° C. and partitioned between EtOAc and water. Aqueous layer was extracted with EtOAc (2×). Combined organic solutions were dried over $Na_2SO_4$ and concentrated to give a tan solid which was used without further purification.

Step F: (1R,2R)-Methyl 2-(2-amino-2-(4-(morpholine-4-carbonyl)phenyl)acetyl)-5,5-difluorocyclohexanecarboxylate hydrochloride This compound was prepared from (1R,2R)-methyl 2-(2-azido-2-(4-(morpholine-4-carbonyl)phenyl)acetyl)-5,5-difluorocyclohexanecarboxylate using a similar procedure as described for (1R,2R)-methyl 2-(2-amino-2-(4-bromophenyl)acetyl)cyclohexanecarboxylate hydrochloride in Step D of Example 1.

Step G: (1R,2R)-Methyl 5,5-difluoro-2-(2-(4-(morpholine-4-carbonyl)phenyl)-2-(2,2,3,3,3-pentafluoro-N-(2,2,3,3,3-pentafluoropropanoyl)propanamido)acetyl)cyclohexanecarboxylate To a solution of (1R,2R)-methyl 2-(2-amino-2-(4-(morpholine-4-carbonyl)phenyl)acetyl)-5,5-difluorocyclohexanecarboxylate hydrochloride (100 mg, 0.217 mmol) and $Et_3N$ (88 mg, 0.868 mmol) in dichloromethane (3 mL) was added a solution of 2,2,3,3,3-pentafluoropropanoic anhydride (135 mg, 0.434 mmol) in dichloromethane (3 mL) dropwise and stirred for 30 min. The reaction mixture was then concentrated and purified by reverse phase HPLC (Sunfire C18 30×150 mm column; 5 to 95% MeCN in water. 0.1% TFA modifier for MeCN and water) to give desired product as a white solid (44 mg, 28%).

Step H: (1R,2R)-Methyl 5,5-difluoro-2-(4-(4-(morpholine-4-carbonyl)phenyl)-2-(perfluoroethyl)oxazol-5-yl)cyclohexanecarboxylate A solution of (1R,2R)-methyl 5,5-difluoro-2-(2-(4-(morpholine-4-carbonyl)phenyl)-2-(2,2,3,3,3-pentafluoro-N-(2,2,3,3,3-pentafluoropropanoyl)propanamido)acetyl)cyclohexanecarboxylate (44 mg, 0.061 mmol) in MeOH (2 mL) was treated with solid $K_2CO_3$ (212 mg, 1.535 mmol) and stirred at 23° C. for 1 h. The reaction mixture was then partitioned between EtOAc and water. Aqueous layer was extracted with EtOAc (3×). Combined organic solutions were dried over $Na_2SO_4$ and concentrated to give a tan solid which was used without further purification.

Step I: (1R,2R)-5,5-Difluoro-2-(4-(4-(morpholine-4-carbonyl)phenyl)-2-(perfluoroethyl)oxazol-5-yl)cyclohexanecarboxylic acid Concentrated sulfuric acid (0.5 mL) was added dropwise to a solution of (1R,2R)-methyl 5,5-difluoro-2-(4-(4-(morpholine-4-carbonyl)phenyl)-2-(perfluoroethyl)oxazol-5-yl)cyclohexanecarboxylate (34 mg, 0.062 mmol) in THF-water (1:1, 1 mL) and stirred at 60° C. for 2 h. The reaction mixture was then partitioned between EtOAc and water. Aqueous layer was extracted with EtOAc (3×). Combined organic solutions were washed with brine, dried over $Na_2SO_4$ and concentrated to give a tan solid which was used without further purification.

Step J: (1R,2R)—N-(1-Cyanocyclopropyl)-5,5-difluoro-2-(4-(4-(morpholine-4-carbonyl)phenyl)-2-(perfluoroethyl)oxazol-5-yl)cyclohexanecarboxamide (Compound 2)

This compound was prepared from (1R,2R)-5,5-difluoro-2-(4-(4-(morpholine-4-carbonyl)phenyl)-2-(perfluoroethyl)oxazol-5-yl)cyclohexanecarboxylic acid as described for (1R,2R)-2-(4-(4-bromophenyl)-2-(3,4-difluorophenyl)oxazol-5-yl)-N-(1-cyanocyclopropyl)cyclohexanecarboxamide in Step H of Example 1. MS $[M+H]^+$ 603.0. $^1$H NMR (400 MHz, $CDCl_3$) δ 7.77 (d, J=8.3 Hz, 2H), 7.52 (d, J=8.3 Hz, 2H), 6.17 (s, 1H), 3.90-3.42 (m, 10H), 2.88-2.82 (m, 1H), 2.35-1.80 (m, 5H), 1.35-1.43 (m, 2H), 0.68-0.98 (m, 2H).

Example 3

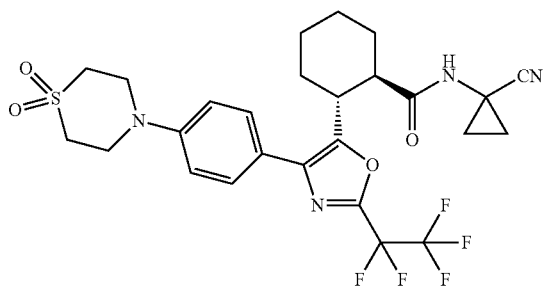 [SMILES: N#CC1(NC(=O)[C@@H]2CCCC[C@H]2c2oc(C(F)(F)C(F)(F)F)nc2-c2ccc(N3CCS(=O)(=O)CC3)cc2)CC1]

(1R,2R)—N-(1-Cyanocyclopropyl)-2-(4-(4-(1,1-dioxidothiomorpholino)phenyl)-2-(perfluoroethyl)oxazol-5-yl)cyclohexanecarboxamide (Compound 3)

Step A: (1R,2R)-Methyl 2-(4-(4-bromophenyl)-2-(perfluoroethyl)oxazol-5-yl)cyclohexanecarboxylate To a solution of (1R,2R)-methyl 2-(2-amino-2-(4-bromophenyl)acetyl)cyclohexanecarboxylate hydrochloride from Step D Example 1 (250 mg, 0.64 mmol) and Et$_3$N (259 mg, 2.56 mmol) in dichloromethane (3 mL) was added a solution of 2,2,3,3,3-pentafluoropropanoic anhydride (397 mg, 1.28 mmol) in dichloromethane (3 mL) dropwise and stirred for 15 min. The reaction mixture was partitioned between dichloromethane and saturated aqueous NaHCO$_3$ solution. Aqueous layer was extracted with dichloromethane (3×). Combined organic solutions were dried over Na$_2$SO$_4$ and concentrated and purified by reverse phase HPLC (Sunfire C18 30×150 mm column; 30 to 95% MeCN in water. 0.1% TFA modifier for MeCN and water) to give desired product as a viscous yellow liquid (60 mg, 20%).

Step B: (1R,2R)-2-(4-(4-Bromophenyl)-2-(perfluoroethyl)oxazol-5-yl)cyclohexanecarboxylic acid This compound was prepared from (1R,2R)-methyl 2-(4-(4-bromophenyl)-2-(perfluoroethyl)oxazol-5-yl)cyclohexanecarboxylate as described for (1R,2R)-2-(4-(4-bromophenyl)-2-(3,4-difluorophenyl)oxazol-5-yl)cyclohexanecarboxylic acid in Step G Example 1.

Step C: (1R,2R)-2-(4-(4-Bromophenyl)-2-(perfluoroethyl)oxazol-5-yl)-N-(1-cyanocyclopropyl)cyclohexanecarboxamide This compound was prepared from (1R,2R)-2-(4-(4-bromophenyl)-2-(perfluoroethyl)oxazol-5-yl)cyclohexanecarboxylic acid as described for (1R,2R)-2-(4-(4-bromophenyl)-2-(3,4-difluorophenyl)oxazol-5-yl)-N-(1-cyanocyclopropyl)cyclohexanecarboxamide in Step H of Example 1.

Step D: (1R,2R)—N-(1-Cyanocyclopropyl)-2-(4-(4-(1,1-dioxidothiomorpholino)phenyl)-2-(perfluoroethyl)oxazol-5-yl)cyclohexanecarboxamide (Compound 3)

This compound was prepared from (1R,2R)-2-(4-(4-bromophenyl)-2-(perfluoroethyl)oxazol-5-yl)-N-(1-cyanocyclopropyl)cyclohexanecarboxamide as described for (1R,2R)—N-(1-cyanocyclopropyl)-2-(2-(3,4-difluorophenyl)-4-(4-(1,1-dioxidothiomorpholino)phenyl)oxazol-5-yl)cyclohexanecarboxamide in Step I of Example 1. MS [M+H]$^+$ 587.5. $^1$H NMR (400 MHz, CDCl$_3$) δ 7.64 (d, J=8.8 Hz, 2H), 6.98 (d, J=8.9 Hz, 2H), 5.82 (s, 1H), 3.95-3.92 (m, 4H), 3.41-3.34 (m, 1H), 3.14-3.11 (m, 4H), 2.50-2.44 (m, 1H), 2.01-1.08 (m, 10H), 0.89-0.73 (m, 2H).

Example 4

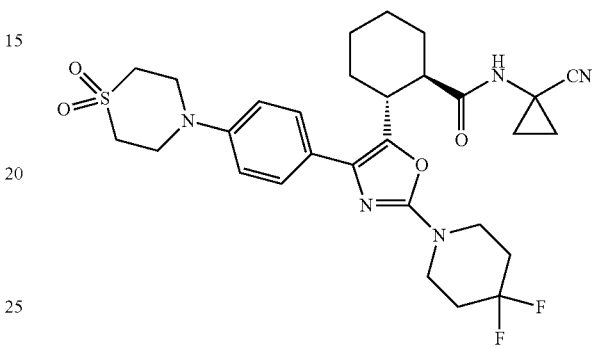

(1R,2R)—N-(1-Cyanocyclopropyl)-2-(2-(4,4-difluoropiperidin-1-yl)-4-(4-(1,1-dioxidothiomorpholino)phenyl)oxazol-5-yl)cyclohexanecarboxamide (Compound 4)

Step A: (1R,2R)-Methyl 2-(2-(4-bromophenyl)-2-isocyanatoacetyl)cyclohexanecarboxylate To a solution of (1R,2R)-methyl 2-(2-amino-2-(4-bromophenyl)acetyl)cyclohexanecarboxylate hydrochloride from Step D Example 1 (100 mg, 0.256 mmol) in dichloromethane (3 mL) at 0° C. was added aqueous saturated NaHCO$_3$ solution (5 mL). Triphosgene (53 mg, 0.179 mmol) was added to this biphasic mixture while stirring rapidly. After 15 min at 0° C., the reaction mixture was stirred at 23° C. for 2 h and then diluted with dichloromethane. Layers were separated. Aqueous layer was extracted with dichloromethane (3×). Combined organic solutions were dried over Na$_2$SO$_4$ and concentrated to give a colorless viscous liquid which was used without further purification.

Step B: (1R,2R)-Methyl 2-(2-(4-bromophenyl)-2-(4,4-difluoropiperidine-1-carboxamido)acetyl)cyclohexanecarboxylate To a suspension of 4,4-difluoropiperidin-1-ium chloride (121 mg, 0.765 mmol) in dichloromethane (0.5 mL) was added Hunig's base (99 mg, 0.765 mmol). This mixture was sonicated until all solids dissolved. To this solution was added a solution of (1R,2R)-methyl 2-(2-(4-bromophenyl)-2-isocyanatoacetyl)cyclohexanecarboxylate (97 mg, 0.255 mmol) in dichloromethane (1.5 mL) and stirred at rt overnight. The reaction mixture was then concentrated and purified by reverse phase HPLC (Sunfire C18 30×150 mm column; 10 to 95% MeCN in water. 0.1% TFA modifier for MeCN and water) to give desired product as a colorless viscous liquid (48 mg, 38%).

Step C: (1R,2R)-Methyl 2-(4-(4-bromophenyl)-2-(4, 4-difluoropiperidin-1-yl)oxazol-5-yl)cyclohexan- ecarboxylate A solution of (1R,2R)-methyl 2-(2-(4-bromophenyl)-2-(4, 4-difluoropiperidine-1-carboxamido)acetyl)cyclohexan- ecarboxylate (48 mg, 0.096 mmol) in POCl$_3$ (1 mL) was stirred at 50° C. for 4 h. The solution was concentrated and the resulting residue was dissolved in dichloromethane and cooled to 0 C. Saturated aqueous NaHCO$_3$ solution was added to the dichloromethane solution until the aqueous layer became basic. Layers were separated. Aqueous layer was extracted with dichloromethane (3×). Combined organic solutions were dried over Na$_2$SO$_4$, filtered and concentrated. Purified by flash chromatography (4 g SiO$_2$) using a linear gradient of 3 to 30% EtOAc in hexanes to give a white solid (22 mg, 48%).

Step D: (1R,2R)-Methyl 2-(2-(4,4-difluoropiperidin- 1-yl)-4-(4-(1,1-dioxidothiomorpholino)phenyl)ox- azol-5-yl)cyclohexanecarboxylate This compound was prepared from (1R,2R)-methyl 2-(4- (4-bromophenyl)-2-(4,4-difluoropiperidin-1-yl)oxazol-5-yl) cyclohexanecarboxylate as described for (1R,2R)—N-(1- cyanocyclopropyl)-2-(2-(3,4-difluorophenyl)-4-(4-(1,1- dioxidothiomorpholino)phenyl)oxazol-5-yl) cyclohexanecarboxamide in Step I of Example 1.

Step E: (1R,2R)-2-(2-(4,4-Difluoropiperidin-1-yl)-4- (4-(1,1-dioxidothiomorpholino)phenyl)oxazol-5-yl) cyclohexanecarboxylic acid To a solution of (1R,2R)-methyl 2-(2-(4,4-difluoropiperi- din-1-yl)-4-(4-(1,1-dioxidothiomorpholino)phenyl)oxazol- 5-yl)cyclohexanecarboxylate (23 mg, 0.043 mmol) in MeOH-THF (1:3, 0.8 mL) was added aqueous NaOH solu- tion (1 N, 0.193 mL) and stirred at 40° C. overnight. The reaction mixture was then partitioned between aqueous saturated NH$_4$Cl solution and dichloromethane. Aqueous layer was extracted with dichloromethane (3×). Combined organic solutions were dried over Na$_2$SO$_4$ and concentrated to give a light yellow sticky solid which was used without further purification.

Step F: (1R,2R)—N-(1-Cyanocyclopropyl)-2-(2-(4, 4-difluoropiperidin-1-yl)-4-(4-(1,1-dioxidothiomor- pholino)phenyl)oxazol-5-yl)cyclohexanecarboxam- ide (Compound 4)

This compound was prepared from (1R,2R)-2-(2-(4,4- difluoropiperidin-1-yl)-4-(4-(1,1-dioxidothiomorpholino) phenyl)oxazol-5-yl)cyclohexanecarboxylic acid as described for (1R,2R)-2-(4-(4-bromophenyl)-2-(3,4-difluo- rophenyl)oxazol-5-yl)-N-(1-cyanocyclopropyl)cyclohexan- ecarboxamide in Step H of Example 1. MS [M+H]$^+$ 588.2. $^1$H NMR (400 MHz, CDCl$_3$) δ 7.53 (d, J=8.6 Hz, 2H), 6.94 (d, J=8.8 Hz, 2H), 5.61 (s, 1H), 3.91-3.88 (m, 4H), 3.70-3.66 (m, 4H), 3.12-3.06 (m, 5H), 2.37-2.99 (m, 1H), 2.12-1.59 (m, 9H), 1.40-1.21 (m, 5H), 0.70-0.76 (m, 2H).

Example 5

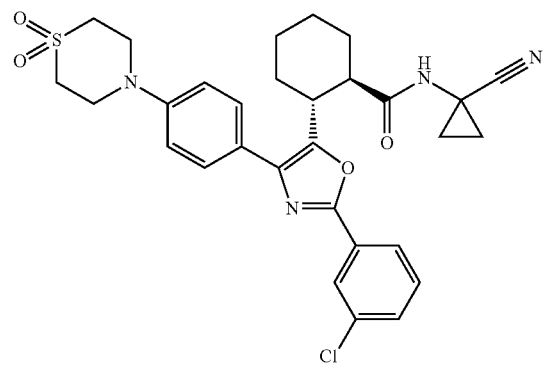 [SMILES: N#CC1(NC(=O)[C@@H]2CCCC[C@H]2c2oc(-c3cccc(Cl)c3)nc2-c2ccc(N3CCS(=O)(=O)CC3)cc2)CC1]

(1R,2R)-2-(2-(3-Chlorophenyl)-4-(4-thiomor- pholino-1,1-dioxide-phenyl)oxazol-5-yl)-N-(1-cya- nocyclopropyl)cyclohexanecarboxamide (Com- pound 5)

Step A: (1R,2R)-Methyl-2-(2-(4-bromophenyl)-2- (3-chlorobenzamido)acetyl)cyclohexanecarboxylate Into a 25-mL 3-necked round-bottom flask purged and maintained with an inert atmosphere of nitrogen, were added (1R,2R)-methyl-2-[2-amino-2-(4-bromophenyl)acetyl]cy- clohexane-1-carboxylate hydrochloride from Step D Example 1 (0.15 g, 0.38 mmol, 1.00 equiv) and dichlo- romethane (5 mL). To this solution were added a solution of 3-chlorobenzoyl chloride (0.27 g, 1.54 mmol, 4.00 equiv) in dichloromethane (5 mL) and N,N-diisopropylethylamine (0.30 g, 2.31 mmol, 6.00 equiv) at 0° C. The reaction solution was stirred for 30 min at 0° C. The reaction solution was quenched by the addition of saturated aqueous sodium bicarbonate (10 mL). The mixture was extracted with dichloromethane (2×10 mL). The combined organic layers was washed with brine (10 mL), dried over anhydrous sodium sulfate and filtered. The filtrate was concentrated under vacuum. This resulted in 0.20 g of (1R,2R)-Methyl- 2-(2-(4-bromophenyl)-2-(3-chlorobenzamido)acetyl)cyclo- hexanecarboxylateas a light yellow oil: MS (ES, m/z): 492.1 (M+1), 494.1 (M+1).

Step B: (1R,2R)-Methyl 2-(4-(4-bromophenyl)-2- (3-chlorophenyl)oxazol-5-yl)cyclohexanecarboxy- late Into a 25-mL round-bottom flask, were placed (1R,2R)- methyl-2-[2-(4-bromophenyl)-2-[(3-chlorophenyl)forma- mido]acetyl]cyclohexane-1-carboxylate (0.200 g, 0.410 mmol, 1.00 equiv), toluene (4 mL) and phosphoroyl trichlo- ride (6 mL). The reaction solution was stirred for 16 h at 80° C. in an oil bath. The solvent was removed under reduced pressure. The residue was diluted with ice/water (10 mL). The aqueous layer was extracted with ethyl acetate (3×8 mL). The combined organic layers was washed with brine (10 mL), dried over anhydrous sodium sulfate and filtered. The filtrate was concentrated under vacuum. The residue was applied onto silica gel column chromatography with ethyl acetate/petroleum ether (5%-40%). This resulted in 0.13 g (67%) of (1R,2R)-methyl-2-[4-(4-bromophenyl)-2-

(3-chlorophenyl)oxazol-5-yl)cyclohexanecarboxylate as a light yellow solid: MS (ES, m/z): 473.9 (M+1), 475.9 (M+1)

Step C: (1R,2R)-2-(4-(4-Bromophenyl)-2-(3-chlorophenyl)oxazol-5-yl)cyclohexanecarboxylic acid Into a 25-mL round-bottom flask, were placed (1R,2R)-methyl-2-[4-(4-bromophenyl)-2-(3-chlorophenyl)-1,3-oxazol-5-yl]cyclohexane-1-carboxylate (0.22 g, 0.46 mmol, 1.00 equiv), aqueous sodium hydroxide (1 M, 1.90 mL, 4.00 equiv), methanol (3 mL) and tetrahydrofuran (5 mL). The reaction mixture was stirred for 3 h at 60° C. in an oil bath. The pH value of the mixture was adjusted to 2 with aqueous hydrochloric acid (1 M). The mixture was extracted with ethyl acetate (3×10 mL). The combined organic layers was washed with brine (10 mL), dried over anhydrous sodium sulfate and filtered. The filtrate was concentrated under vacuum. This resulted in 0.21 g (98%) of (1R,2R)-2-(4-(4-bromophenyl)-2-(3-chlorophenyl)oxazol-5-yl)cyclohexanecarboxylic acid as a yellow solid: MS (ES, m/z): 460.1 (M+1), 462.1 (M+1).

Step D: (1R,2R)-2-(4-(4-Bromophenyl)-2-(3-chlorophenyl)oxazol-5-yl)-N-(1-cyanocyclopropyl)cyclohexanecarboxamide Into a 10-mL round-bottom flask purged and maintained with an inert atmosphere of nitrogen, was placed a solution of (1R,2R)-2-[4-(4-bromophenyl)-2-(3-chlorophenyl)oxazol-5-yl)cyclohexane-carboxylic acid (0.21 g, 0.46 mmol, 1.00 equiv) in N,N-dimethylformamide (5 mL), 2-(7-aza-1H-benzotriazole-1-yl)-1,1,3,3-tetramethyluronium hexafluorophosphate (0.26 g, 0.68 mmol, 1.50 equiv), 1-aminocyclopropane-1-carbonitrile hydrochloride (0.14 g, 1.14 mmol, 2.50 equiv) and N,N-diisopropylethylamine (0.29 g, 2.28 mmol, 5.00 equiv). The reaction solution was stirred for 16 h at 40° C. in an oil bath and quenched by the addition of water/ice (10 mL). The mixture was extracted with ethyl acetate (2×10 mL). The combined organic layers were washed with brine (2×6 mL), dried over anhydrous sodium sulfate and filtered. The filtrate was concentrated under vacuum. The residue was purified by preparative thin layer chromatography with ethyl acetate/petroleum ether (1:1). This resulted in 0.17 g (71%) of (1R,2R)-2-(4-(4-Bromophenyl)-2-(3-chlorophenyl)oxazol-5-yl)-N-(1-cyanocyclopropyl)cyclohexanecarboxamide as a light yellow solid: MS (ES, m/z): 524.2 (M+1), 526.2 (M+1).

Step E: (1R,2R)-2-(2-(3-Chlorophenyl)-4-(4-(1,1-dioxidothiomorpholino)phenyl)oxazol-5-yl)-N-(1-cyanocyclopropyl)cyclohexanecarboxamide (Compound 5)

Into a 10-mL sealed tube purged and maintained with an inert atmosphere of nitrogen, were placed (1R,2R)-2-[4-(4-bromophenyl)-2-(3-chlorophenyl)oxazol-5-yl)-N-(1-cyanocyclopropyl)cyclohexanecarboxamide (60.0 mg, 0.11 mmol, 1.00 equiv), thiomorpholine-1,1-dione hydrochloride (59.0 mg, 0.34 mmol, 3.00 equiv), potassium phosphate (0.12 g, 0.57 mmol, 5.00 equiv), chloro{[2-dicyclohexylphosphino-2',4',6'-triisopropylbiphenyl][2-(2-aminoethylphenyl]palladium(II)]} (8.40 mg, 0.01 mmol, 0.10 equiv) and tetrahydrofuran (3 mL). The mixture was lightly degassed by three repetitive cycles of vacuum (1-2 s), and nitrogen refilling. The reaction mixture was stirred for 6 h at 120° C. in an oil bath. The resulting mixture was filtered and the filtrate was concentrated under vacuum. The crude product was purified by Prep-HPLC with the following conditions: Column, Xbridge C18, 5 μm, 25×150 mm; Mobile phase: Water (0.05% ammonium bicarbonate) and acetonitrile (47% acetonitrile up to 60% in 10 min, hold 100% for 3 min, down to 47% in 1 min); Detector, UV 220 and 254 nm. This resulted in 16.0 mg (24%) of (1R,2R)-2-(2-(3-Chlorophenyl)-4-(4-(1,1-dioxidothiomorpholino)phenyl)oxazol-5-yl)-N-(1-cyanocyclopropyl)cyclohexanecarboxamide (Compound 5) as a colorless solid: $^1$H NMR (300 MHz, CD$_3$OD) δ ppm 8.10 (s, 1H), 8.06-7.95 (m, 1H), 7.67 (d, J=8.4 Hz, 2H), 7.56-7.50 (m, 2H), 7.16 (d, J=8.7 Hz, 2H), 4.10-3.93 (m, 4H), 3.33-3.27 (m, 1H), 3.21-3.17 (m, 4H), 2.74-2.66 (m, 1H), 2.06-1.65 (m, 6H), 1.62-1.49 (m, 2H), 1.35-1.30 (m, 2H), 0.79-0.64 (m, 2H); MS (ES, m/z): 579.3 (M+1), 581.3 (M+1).

Example 6

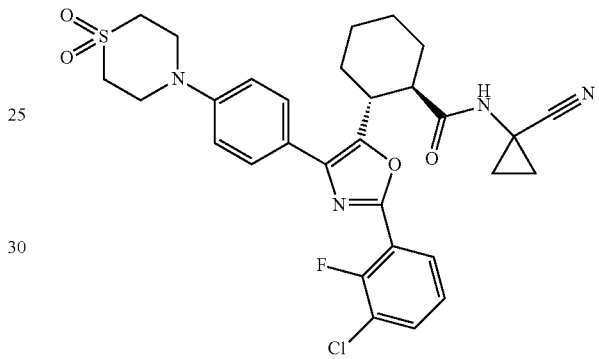

(1R,2R)-2-(2-(3-chloro-2-fluorophenyl)-4-(4-(1,1-dioxidothiomorpholino)phenyl)oxazol-5-yl)-N-(1-cyanocyclopropyl)cyclohexanecarboxamide (Compound 6)

Step A: 3-Chloro-2-fluorobenzoyl chloride

Into a 50-mL round-bottom flask, was placed a solution of 3-chloro-2-fluorobenzoic acid (0.30 g, 1.72 mmol, 1.00 equiv) in dichloromethane (10 mL). To this solution was added oxalyl chloride (0.2 mL) dropwise, and one drop of N,N-dimethylformamide. The reaction solution was stirred for 15 h at ambient temperature. The resulting solution was concentrated under vacuum. This resulted in 0.33 g (98%) of 3-chloro-2-fluorobenzoyl chloride as a yellow oil.

Step B: (1R,2R)-Methyl 2-(2-(4-bromophenyl)-2-(3-chloro-2-fluorobenzamido)acetyl)cyclohexanecarboxylate Into a 50-mL round-bottom flask, was placed a solution of (1R,2R)-methyl-2-[2-amino-2-(4-bromophenyl)acetyl]cyclohexane-1-carboxylate hydrochloride (0.25 g, 0.64 mmol, 1.00 equiv) in dichloromethane (10 mL). This was followed by the addition of triethylamine (0.5 mL). The reaction solution was stirred for 10 min at 0° C. To this was added 3-chloro-2-fluorobenzoyl chloride (0.308 g, 1.60 mmol, 2.50 equiv). The reaction solution was stirred for 12 h while slowly warming to ambient temperature. The resulting mixture was concentrated under vacuum, and diluted with water (10 mL). The resulting mixture was extracted with dichloromethane (3×30 mL). The combined organic layers was dried over anhydrous sodium sulfate and filtered. The filtrate was concentrated under vacuum. This resulted in 0.41 g of crude (1R,2R)-methyl-2-[2-(4-bromophenyl)-2-(3-chloro-2-fluorobenzamido)acetyl)cyclohexanecarboxylate as a yellow oil: MS (ES, m/z): 532.2 (M+23), 534.2 (M+23).

Step C: (1R,2R)-Methyl 2-(4-(4-bromophenyl)-2-(3-chloro-2-fluorophenyl)oxazol-5-yl)cyclohexanecarboxylate Into a 25-mL round-bottom flask, was placed a solution of (1R,2R)-Methyl 2-(2-(4-bromophenyl)-2-(3-chloro-2 fluorobenzamido)acetyl)cyclohexanecarboxylate (0.41 g, 0.80 mmol, 1.00 equiv) in toluene (0.5 mL). To this solution was added phosphoryl trichloride (4 mL). The reaction solution was stirred for 5 h at 80° C. in an oil bath. The resulting solution was concentrated under vacuum, and quenched by the addition of water/ice (10 mL). The pH value of the mixture was adjusted to 10 with saturated aqueous sodium bicarbonate. The resulting mixture was extracted with ethyl acetate (2×30 mL). The combined organic layers was dried over anhydrous sodium sulfate and filtered. The filtrate was concentrated under vacuum. The residue was applied onto silica gel column chromatography with ethyl acetate/petroleum ether (1:9). This resulted in 0.12 g (30%) of (1R,2R)-methyl 2-(4-(4-bromophenyl)-2-(3-chloro-2-fluorophenyl)oxazol-5-yl)cyclohexanecarboxylate as a yellow oil: MS (ES, m/z): 492.0 (M+1), 494.0 (M+1).

Step D: (1R,2R)-Methyl 2-(2-(3-chloro-2-fluorophenyl)-4-(4-(1,1-dioxidothiomorpholino)phenyl)oxazol-5-yl)cyclohexanecarboxylate Into a 10-mL round-bottom flask purged and maintained with an inert atmosphere of nitrogen, was placed a solution of (1R,2R)-methyl 2-(4-(4-bromophenyl)-2-(3-chloro-2-fluorophenyl)oxazol-5-yl)cyclohexanecarboxylate (0.12 g, 0.24 mmol, 1.00 equiv) in tetrahydrofuran (2 mL). To this solution was added thiomorpholine-1,1-dioxide hydrochloride (0.13 g, 0.73 mmol, 3.00 equiv), potassium phosphate (0.26 g, 1.22 mmol, 5.00 equiv), chloro{[2-dicyclohexylphosphino-2',4',6'-triisopropylbiphenyl][2-(2-aminoethylphenyl]palladium(II)]} (18.0 mg, 0.020 mmol, 0.100 equiv). The reaction mixture was lightly degassed by three repetitive cycles of vacuum (1-2 s), and nitrogen refilling. The reaction mixture was stirred for 48 h at 100° C. in an oil bath. The resulting mixture was diluted with water (10 mL) and extracted with ethyl acetate (2×30 mL). The combined organic layers were dried over anhydrous sodium sulfate and filtered. The filtrate was concentrated under vacuum. The residue was applied onto silica gel column chromatography with ethyl acetate/petroleum ether (1:1). This resulted in 60.0 mg (45%) of (1R,2R)-methyl 2-(2-(3-chloro-2-fluorophenyl)-4-(4-(1,1-dioxidothiomorpholino)phenyl)oxazol-5-yl)cyclohexanecarboxylate as a yellow oil: MS (ES, m/z): 569.1 (M+23), 571.1 (M+23).

Step E: (1R,2R)-2-(2-(3-Chloro-2-fluorophenyl)-4-(4-(1,1-dioxidothiomorpholino)phenyl)oxazol-5-yl)cyclohexanecarboxylic acid Into a 25-mL round-bottom flask, was placed of (1R,2R)-methyl 2-(2-(3-chloro-2-fluorophenyl)-4-(4-(1,1-dioxidothiomorpholino)phenyl)oxazol-5-yl)cyclohexanecarboxylate (60.0 mg, 0.11 mmol, 1.00 equiv). To this were added 1 M aqueous sodium hydroxide (2 mL, 18.8 equiv), methanol (2 mL) and tetrahydrofuran (2 mL). The reaction mixture was stirred for 1 h at 60° C. in an oil bath. The resulting mixture was concentrated under vacuum and diluted with water (5 mL). The pH value of the solution was adjusted to 4 with aqueous hydrochloric acid (10%). The resulting mixture was extracted with ethyl acetate (2×15 mL). The combined organic layers were dried over anhydrous sodium sulfate and filtered. The filtrate was concentrated under vacuum. This resulted in 60.0 mg (92%) of (1R,2R)-2-(2-(3-chloro-2-fluorophenyl)-4-(4-(1,1-dioxidothiomorpholino)phenyl)oxazol-5-yl)cyclohexanecarboxylic acid as a yellow oil: MS (ES, m/z): 533.1 (M+1), 535.1 (M+1).

Step F: (1R,2R)-2-(2-(3-Chloro-2-fluorophenyl)-4-(4-(1,1-dioxidothiomorpholino)phenyl)oxazol-5-yl)-N-(1-cyanocyclopropyl)cyclohexanecarboxamide (Compound 6)

Into a 10-mL round-bottom flask purged and maintained with an inert atmosphere of nitrogen, was placed a solution of (1R,2R)-2-(2-(3-chloro-2-fluorophenyl)-4-(4-(1,1-dioxidothiomorpholino)phenyl)oxazol-5-yl)cyclohexanecarboxylic acid (60.0 mg, 0.11 mmol, 1.00 equiv) in N,N-dimethylformamide (5.0 mL). To this solution were added 1-aminocyclopropane-1-carbonitrile hydrochloride (66.7 mg, 0.56 mmol, 5.00 equiv), 2-(1H-7-azabenzotriazol-1-yl)-1,1,3,3-tetramethyl uronium hexafluorophosphate methanaminium (68.5 mg, 0.18 mmol, 1.60 equiv) and N,N-diisopropylethylamine (0.12 g, 0.90 mmol, 8.00 equiv). The reaction solution was stirred for 24 h at ambient temperature. The resulting solution was diluted with ethyl acetate (30 mL) and washed with water (3×10 mL). The organic layer was dried over anhydrous sodium sulfate and filtered. The filtrate was concentrated under vacuum. The residue was purified by preparative thin layer chromatography with ethyl acetate/petroleum ether (1:1). This resulted in 18.5 mg (28%) of (1R,2R)-2-(2-(3-Chloro-2-fluorophenyl)-4-(4-(1,1-dioxidothiomorpholino)phenyl)oxazol-5-yl)-N-(1-cyanocyclopropyl)cyclohexanecarboxamide (Compound 6) as a colorless solid: $^1$H-NMR (300 MHz, DMSO-$d_6$) δ ppm 8.80 (s, 1H), 8.07-7.97 (m, 1H), 7.85-7.73 (m, 1H), 7.63 (d, J=8.4 Hz, 2H), 7.47-7.35 (m, 1H), 7.14 (d, J=8.1 Hz, 2H), 4.00-3.80 (m, 4H), 3.33-3.22 (m, 1H), 3.21-3.10 (m, 4H), 2.67-2.55 (m, 1H), 2.00-1.72 (m, 4H), 1.70-1.23 (m, 6H), 0.72-0.60 (m, 1H), 0.50-0.40 (m, 1H); MS (ES, m/z): 597.3 (M+1), 599.3 (M+1).

Example 7

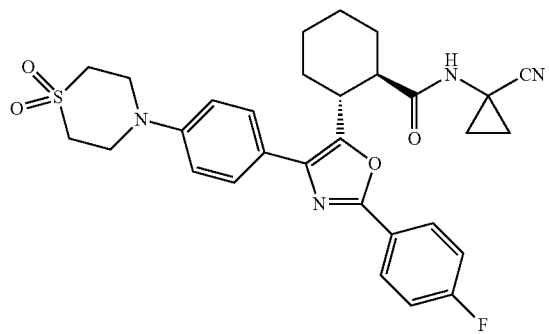 [SMILES: N#CC1(NC(=O)[C@@H]2CCCC[C@H]2c2oc(-c3ccc(F)cc3)nc2-c2ccc(N3CCS(=O)(=O)CC3)cc2)CC1]

(1R,2R)—N-(1-Cyanocyclopropyl)-2-{4-[4-(1,1-dioxo-1λ⁶-thiomorpholin-4-yl)phenyl]-2-(4-fluorophenyl)-1,3-oxazol-5-yl}cyclohexanecarboxamide (Compound 7)

Step-A: (1R,2R)-methyl 2-(2-(4-bromophenyl)-2-(4-fluorobenzamido)acetyl)cyclohexanecarboxylate To a solution of (1R,2R)-methyl 2-(2-amino-2-(4-bromophenyl)acetyl)cyclohexanecarboxylate hydrochloride (250 mg, 0.64 mmol) in dichloromethane at 0° C. was added 4-fluorobenzoyl chloride (406 mg, 2.56 mmol) followed by Hunig's base (496 mg, 3.84 mmol); stirred at 0° C. for 15 min and then concentrated. The residue was dissolved in DMSO and purified by reverse phase HPLC (Sunfire C18 30×150 mm column; 20 to 95% MeCN in water. 0.1% TFA modifier for MeCN and water) to give desired product as a white solid (108 mg, 35%).

Step-B: (1R,2R)-methyl 2-(4-(4-bromophenyl)-2-(4-fluorophenyl)oxazol-5-yl)cyclohexanecarboxylate A solution of (1R,2R)-methyl 2-(2-(4-bromophenyl)-2-(4-fluorobenzamido)acetyl)cyclohexanecarboxylate (122 mg, 0.256 mmol) in POCl₃ (2 mL) was heated at 80° C. for 5.5 h and at 40° C. for 14 h. The solution was concentrated and the resulting residue was dissolved in dichloromethane and cooled to 0° C. Saturated aqueous NaHCO₃ solution was added to the dichloromethane solution until the aqueous layer became basic. Layers were separated. Aqueous layer was extracted with dichloromethane (3×). Combined organic solutions were dried over Na₂SO₄, filtered and concentrated to give a white solid which was used without further purification.

Step-C: (1R,2R)-2-(4-(4-bromophenyl)-2-(4-fluorophenyl)oxazol-5-yl)cyclohexanecarboxylic acid A solution (1R,2R)-methyl 2-(4-(4-bromophenyl)-2-(4-fluorophenyl)oxazol-5-yl)cyclohexanecarboxylate (117 mg, 0.255 mmol) in MeOH-THF (1:1, 2 mL) was treated with 1 N aqueous NaOH solution (1.021 mL) and stirred at 40° C. for 14 h. After cooling down to rt, 1.021 mL of 1 N aqueous HCl was added. The resulting solution was concentrated to a white solid which was used without further purification.

Step-D: (1R,2R)-2-(4-(4-bromophenyl)-2-(4-fluorophenyl)oxazol-5-yl)-N-(1-cyanocyclopropyl)cyclohexanecarboxamide To a solution of (1R,2R)-2-(4-(4-bromophenyl)-2-(4-fluorophenyl)oxazol-5-yl)cyclohexanecarboxylic acid (113 mg, 0.254 mmol) and HATU (75 mg, 0.636 mmol) in DMF (2 mL) was added Hunig's base (164 mg, 1.272 mmol) and stirred at 40° C. for 47 h. The resulting solution was purified directly by reverse phase HPLC (Sunfire C18 30×150 mm column; 30 to 95% MeCN in water. 0.1% TFA modifier for MeCN and water) to give desired product as a white solid (85 mg, 66%).

Step-E: (1R,2R)—N-(1-Cyanocyclopropyl)-2-{4-[4-(1,1-dioxo-1λ⁶-thiomorpholin-4-yl)phenyl]-2-(4-fluorophenyl)-1,3-oxazol-5-yl}cyclohexanecarboxamide (Compound 7)

To a mixture of (1R,2R)-2-(4-(4-bromophenyl)-2-(4-fluorophenyl)oxazol-5-yl)-N-(1- cyanocyclopropyl)cyclohexanecarboxamide (116 mg, 0.228 mmol), thiomorpholine 1,1-dioxide (93 mg, 0.685 mmol), Chloro(2-dicyclohexylphosphino-2',4',6'-triisopropyl-1,1'-biphenyl)[2-(2-aminoethyl)phenyl)]palladium(II) (8.43 mg, 0.011 mmol) and K₃PO₄.H₂O (63.1 mg, 0.274 mmol) in a vial under an inert atmosphere was added THF (1.5 mL). The vial was sealed and heated at 100° C. for 2 h., cooled to rt and concentrated. The residue was taken in DMSO, filtered and the filtrate was subjected to reverse phase HPLC purification (Sunfire C18 30×150 mm column; 10 to 95% MeCN in water. 0.1% TFA modifier for MeCN and water). Desired fractions were partitioned between saturated aqueous sodium bicarbonate and dichloromethane. Layers were separated. Aqueous layer was extrated with dichloromethane (3×). Combined organic solutions were dried over Na₂SO₄ and concentrated to give desired product as a white solid (120 mg, 93%). MS [M+H]⁺ 563.1. ¹H NMR (400 MHz, CDCl₃) δ 8.05-8.02 (m, 2H), 7.68-7.63 (m, 2H), 7.21-7.14 (m, 2H), 7.20-6.97 (m, 2H), 5.66 (s, 1H), 3.94-3.91 (m, 1H), 3.30-3.22 (m, 1H), 3.14-3.12 (m, 4H), 2.51-2.44 (m, 1H), 2.1-1.3 (m, 10H), 0.78-0.58 (m, 2H).

Examples 8 and 9

Compound 8 and Compound 9

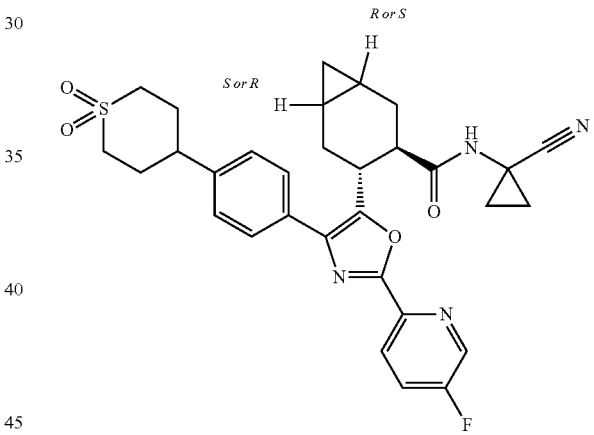

(1S or 1R,3R,4R,6R or 6S)—N-(1-cyanocyclopropyl)-4-(4-(4-(1,1-dioxidothiomorpholino)phenyl)-2-(5-fluoropyridin-2-yl)oxazol-5-yl)bicyclo[4.1.0]heptane-3-carboxamide (Compound 8 and Compound 9)

Step A: (3R,4R)-Methyl 4-(chlorocarbonyl)bicyclo[4.1.0]heptane-3-carboxylate (3R,4R)-Methyl 4-(chlorocarbonyl)bicyclo[4.1.0]heptane-3-carboxylate was synthesized following the same procedure as for synthesis of (1R,2R)-methyl 2-(chlorocarbonyl)cyclohexanecarboxylate using (3R,4R)-4-(methoxycarbonyl)bicyclo[4.1.0]heptane-3-carboxylic acid (1.40 g, 7.06 mmol, 1.00 equiv) and oxalyl chloride (1.80 g, 14.2 mmol, 2.00 equiv) in toluene (30 mL). This resulted in 1.5 g (98%) of the crude (3R,4R)-methyl 4-(chlorocarbonyl) bicyclo[4.1.0]heptane-3-carboxylate as a yellow oil, which was used directly in next step without further purification.

Step B: (3R,4R)-Methyl 4-(2-(4-bromophenyl) acetyl)bicyclo[4.1.0]heptane-3-carboxylate (3R,4R)-Methyl 4-(2-(4-bromophenyl)acetyl)bicyclo[4.1.0]heptane-3-carboxylate was synthesized following the same procedure as in Step A of Example 1 using (3R,4R)-methyl 4-(chlorocarbonyl)bicyclo[4.1.0]heptane-3-carboxylate (0.62 g, 2.86 mmol, 1.00 equiv), copper(I) cyanide-bis(lithium chloride) complex (1 M in tetrahydrofuran, 4.29 mL, 4.29 mmol, 1.50 equiv), and bromo[(4-bromophenyl)methyl]zinc (1 M in tetrahydrofuran, 4.29 mL, 4.29 mmol, 1.50 equiv) in tetrahydrofuran (10 mL). This resulted in 0.51 g (50%) of (3R,4R)-methyl 4-(2-(4-bromophenyl)acetyl)bicyclo[4.1.0]heptane-3-carboxylate as a colorless solid: $^1$H NMR (300 MHz, CDCl$_3$) δ ppm 7.44 (d, J=8.4 Hz, 2H), 7.05 (d, J=8.4 Hz, 2H), 3.76 (s, 2H), 3.65 (s, 3H), 2.73-2.08 (m, 4H), 1.80-1.65 (m, 1H), 1.46-1.24 (m, 1H), 1.04-0.94 (m, 2H), 0.71-0.64 (m, 1H), 0.04-0.00 (m, 1H); MS (ES, m/z): 351.2 (M+1), 353.2 (M+1).

Step C: (3R,4R)-Methyl 4-(2-(4-bromophenyl)-2-chloroacetyl)bicyclo[4.1.0]heptane-3-carboxylate (3R,4R)-Methyl 4-(2-(4-bromophenyl)-2-chloroacetyl)bicyclo[4.1.0]heptane-3-carboxylate was synthesized following the same procedure as in Step B of Example 1 using (3R,4R)-methyl 4-(2-(4-bromophenyl)acetyl)bicyclo[4.1.0]heptane-3-carboxylate (0.51 g, 1.45 mmol, 1.00 equiv) and N-chlorosuccinimide (0.23 g, 1.74 mmol, 1.20 equiv) in N,N-dimethylformamide (10 mL). This resulted in 0.47 g (84%) of (3R,4R)-methyl 4-(2-(4-bromophenyl)-2-chloroacetyl)bicyclo[4.1.0]heptane-3-carboxylate as a yellow oil: MS (ES, m/z): 384.8 (M+1), 386.8 (M+1).

Step D: (3R,4R)-Methyl 4-(2-azido-2-(4-bromophenyl)acetyl)bicyclo[4.1.0]heptane-3-carboxylate (3R,4R)-Methyl 4-(2-azido-2-(4-bromophenyl)acetyl)bicyclo[4.1.0]heptane-3-carboxylate was synthesized following the same procedure as in Step C of Example 1 using (3R,4R)-methyl 4-(2-(4-bromophenyl)-2-chloroacetyl)bicyclo[4.1.0]heptane-3-carboxylate (0.47 g, 1.22 mmol, 1.00 equiv) and sodium azide (94.9 mg, 1.46 mmol, 1.20 equiv) in dimethyl sulfoxide (10 mL). This resulted in 0.47 g of (3R,4R)-methyl 4-(2-azido-2-(4-bromophenyl)acetyl)bicyclo[4.1.0]heptane-3-carboxylate as a light yellow oil, which was used directly in next step without further purification.

Step E: (3R,4R)-Methyl 4-(2-amino-2-(4-bromophenyl)acetyl)bicyclo[4.1.0]heptane-3-carboxylate hydrochloride (3R,4R)-Methyl 4-(2-amino-2-(4-bromophenyl)acetyl)bicyclo[4.1.0]heptane-3-carboxylate hydrochloride was synthesized following the same procedure as in Step D of Example 1 using (3R,4R)-methyl 4-(2-azido-2-(4-bromophenyl)acetyl)bicyclo[4.1.0]heptane-3-carboxylate (0.47 g, 1.20 mmol, 1.00 equiv), zinc powder (0.11 g, 1.68 mmol, 1.40 equiv) and ammonium chloride (0.16 g, 3.00 mmol, 2.50 equiv) in ethanol and water (3:1 (v/v), 12 mL). This resulted in 0.43 g (89%) of (3R,4R)-methyl 4-(2-amino-2-(4-bromophenyl)acetyl)bicyclo[4.1.0]heptane-3-carboxylate hydrochloride as a yellow solid: MS (ES, m/z): 366.2 (M+1), 368.2 (M+1).

Step F: (3R,4R)-Methyl 4-(2-(4-bromophenyl)-2-(5-fluoropicolinamido)acetyl)bicyclo[4.1.0]heptane-3-carboxylate (3R,4R)-Methyl 4-(2-(4-bromophenyl)-2-(5-fluoropicolinamido)acetyl)bicyclo[4.1.0]heptane-3-carboxylate was synthesized following the same procedure as in Step H of Example 1 using (3R,4R)-methyl 4-(2-amino-2-(4-bromophenyl)acetyl)bicyclo[4.1.0]heptane-3-carboxylate hydrochloride (0.43 g, 1.07 mmol, 1.00 equiv), 5-fluoropyridine-2-carboxylic acid (0.38 g, 2.68 mmol, 2.50 equiv), HATU (1.02 g, 2.68 mmol, 2.50 equiv) and N,N-diisopropylethylamine (0.69 g, 5.35 mmol, 5.00 equiv) in N,N-dimethylformamide (15 mL). This resulted in 0.33 g of the crude (3R,4R)-methyl 4-(2-(4-bromophenyl)-2-(5-fluoropicolinamido)acetyl)bicyclo[4.1.0]heptane-3-carboxylate as a yellow oil: MS (ES, m/z): 489.3 (M+1), 491.3 (M+1).

Step G: (3R,4R)-Methyl 4-(4-(4-bromophenyl)-2-(5-fluoropyridin-2-yl)oxazol-5-yl)bicyclo[4.1.0]heptane-3-carboxylate (3R,4R)-Methyl 4-(4-(4-bromophenyl)-2-(5-fluoropyridin-2-yl)oxazol-5-yl)bicyclo[4.1.0]heptane-3-carboxylate was synthesized following the same procedure as in Step F of Example 1 using (3R,4R)-methyl 4-(2-(4-bromophenyl)-2-(5-fluoropicolinamido)acetyl)bicyclo[4.1.0]heptane-3-carboxylate (0.33 g, 0.67 mmol, 1.00 equiv) and phosphoroyl trichloride (10 mL) in toluene (4 mL). This resulted in 0.17 g of (3R,4R)-methyl 4-(4-(4-bromophenyl)-2-(5-fluoropyridin-2-yl)oxazol-5-yl)bicyclo[4.1.0]heptane-3-carboxylate as a light yellow solid: MS (ES, m/z): 471.1 (M+1), 473.1 (M+1).

Step H: (3R,4R)-Methyl 4-(4-(4-(1,1-dioxidothiomorpholino)phenyl)-2-(5-fluoropyridin-2-yl)oxazol-5-yl)bicyclo[4.1.0]heptane-3-carboxylate (3R,4R)-Methyl 4-(2-(5-fluoropyridin-2-yl)-4-(4-thiomorpholino-1,1-dioxide-phenyl)oxazol-5-yl)bicyclo[4.1.0]heptane-3-carboxylate was synthesized following the same procedure as in Step I of Example 1 using (3R,4R)-methyl 4-(4-(4-bromophenyl)-2-(5-fluoropyridin-2-yl)oxazol-5-yl)bicyclo[4.1.0]heptane-3-carboxylate (0.10 g, 0.21 mmol, 1.00 equiv), thiomorpholine-1,1-dioxide hydrochloride (0.11 g, 0.64 mmol, 3.00 equiv), tris(dibenzylideneacetone)dipalladium (0)-chloroform (40 mg, 0.0386 mmol, 0.182 equiv), dicyclohexylphosphino-2',4',6'-triisopropylbiphenyl (30 mg, 0.0629 mmol, 0.297 equiv) and cesium carbonate (0.33 g, 1.01 mmol, 5.00 equiv) in toluene (5 mL). This resulted in 65.0 mg (3R,4R)-methyl 4-(4-(4-(1,1-dioxidothiomorpholino)phenyl)-2-(5-fluoropyridin-2-yl)oxazol-5-yl)bicyclo[4.1.0]heptane-3-carboxylate as a yellow solid: MS (ES, m/z): 526.3 (M+1).

Step I: (3R,4R)-4-(4-(4-(1,1-Dioxidothiomorpholino)phenyl)-2-(5-fluoropyridin-2-yl)oxazol-5-yl)bicyclo[4.1.0]heptane-3-carboxylic acid (3R,4R)-4-(4-(4-(1,1-dioxidothiomorpholino)phenyl)-2-(5-fluoropyridin-2-yl)oxazol-5-yl)bicyclo[4.1.0]heptane-3-carboxylic acid was synthesized following the same procedure as in Step G of Example 1 using (3R,4R)-methyl 4-(4-(4-(1,1-dioxidothiomorpholino)phenyl)-2-(5-fluoropyridin-2-yl)oxazol-5-yl)bicyclo[4.1.0]heptane-3-carboxylate (55.0 mg, 0.11 mmol, 1.00 equiv) in aqueous sodium hydroxide solution (1 M, 2 mL) and tetrahydrofuran (2 mL). This resulted in 50.0 mg (93%) of the desired carboxylic acid as a yellow oil product: MS (ES, m/z): 512.1 (M+1).

Step J: (1S or 1R,3R,4R,6R or 6S)—N-(1-Cyanocyclopropyl)-4-(4-(4-(1,1-dioxidothiomorpholino)phenyl)-2-(5-fluoropyridin-2-yl)oxazol-5-yl)bicyclo[4.1.0]heptane-3-carboxamide (Compound 8 and Compound 9)

Compound 8 and compound 9 were synthesized following the same procedure as in Step H of Example 1 using (3R,4R)-4-(4-(4-(1,1-dioxidothiomorpholino)phenyl)-2-(5-fluoropyridin-2-yl)oxazol-5-yl)bicyclo[4.1.0]heptane-3-carboxylic acid (50.0 mg, 0.0977 mmol, 1.00 equiv), 1-aminocyclopropane-1-carbonitrile hydrochloride (28.9 mg, 0.24 mmol, 2.50 equiv), HATU (55.9 mg, 0.15 mmol, 1.50 equiv) and N,N-diisopropylethylamine (63.2 mg, 0.49 mmol, 5.00 equiv) in N,N-dimethylformamide (5 mL). This resulted in 10.0 mg (14%) (3R,4R)—N-(1-Cyanocyclopropyl)-4-(4-(4-(1,1-dioxidothiomorpholino)phenyl)-2-(5-fluoropyridin-2-yl)oxazol-5-yl)bicyclo[4.1.0]heptane-3-carboxamide as a colorless solid: MS (ES, m/z): 576.2 (M+1). The racemic product (10 mg) was separated by Chiral-Prep-HPLC with the following conditions: Column, Chiralpak IB, 0.46×25 cm, 5 μm Chiral-A(IB) 001 IBOOCE-LA026; mobile phase, Hex:EtOH=60:40; Detector, UV 254 nm and 220 nm. This resulted in 3.6 mg of Compound 8 at 16.1 min as a gray solid: $^1$H NMR (300 MHz, CDCl$_3$) δ ppm 8.68 (s, 1H), 8.44-8.39 (m, 1H), 7.87-7.84 (m, 1H), 7.75 (d, J=8.7 Hz, 2H), 7.68-7.65 (m, 1H), 7.01 (d, J=8.7 Hz, 2H), 3.96-3.92 (m, 4H), 3.16-3.13 (m, 4H), 3.09-3.03 (m, 1H), 2.81-2.70 (m, 1H), 2.37-2.31 (m, 1H), 2.26-2.16 (m, 2H), 1.94-1.86 (m, 1H), 1.35-1.20 (m, 2H), 1.09-1.04 (m, 2H), 0.90-0.85 (m, 2H), 0.78-0.72 (m, 1H), 0.20-0.16 (m, 1H); MS (ES, m/z): 576.0 (M+1). This also resulted in 2.1 mg Compound 9 at 13.4 min as an off-white solid: $^1$H NMR (300 MHz, CDCl$_3$) δ ppm 8.59 (s, 1H), 8.32-8.28 (m, 1H), 7.70-7.69 (m, 1H), 7.69 (d, J=8.7 Hz, 2H), 7.02 (d, J=8.7 Hz, 2H), 6.98 (brs, 1H), 3.95-3.92 (m, 4H), 3.15-3.12 (m, 4H), 3.09-3.04 (m, 1H), 2.64-2.62 (m, 1H), 2.38-2.30 (m, 1H), 2.25-2.15 (m, 2H), 1.98-1.94 (m, 1H), 1.35-1.25 (m, 2H), 1.10-1.03 (m, 2H), 0.95-0.88 (m, 1H), 0.78-0.68 (m, 2H), 0.17-0.16 (m, 1H); MS (ES, m/z): 576.0 (M+1).

Example 10

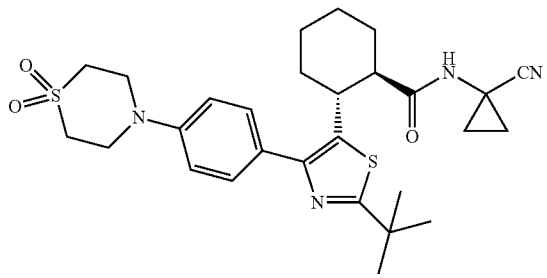 [SMILES: CC(C)(C)c1nc(-c2ccc(N3CCS(=O)(=O)CC3)cc2)c([C@@H]2CCCC[C@H]2C(=O)NC2(C#N)CC2)s1]

(1R,2R)-2-(2-(tert-butyl)-4-(4-(1,1-dioxidothiomorpholino)phenyl)thiazol-5-yl)-N-(1-cyanocyclopropyl)cyclohexanecarboxamide (Compound 10)

Step A: (1R,2R)-Methyl 2-(2-(4-bromophenyl)-2-pivalamidoacetyl)cyclohexanecarboxylate To a solution of crude 1-(4-bromophenyl)-2-((1R,2R)-2-(methoxycarbonyl)cyclohexyl)-2-oxoethanaminium chloride (287 mg, 0.735 mmol) in dichloromethane (5 mL) at 0° C. was added pivaloyl chloride (0.362 mL, 2.94 mmol, 4 eq) followed by dropwise addition of Hunig's base (0.77 mL, 4.41 mmol). The resulting solution was stirred at 0° C. for 15 min and then concentrated under reduced pressure. The residue was dissolved in DMSO and purified by reverse phase HPLC (Sunfire C18 30×150 mm column; 15 to 95% MeCN in water. 0.1% TFA modifier for MeCN and water) to give the desired product as a white solid (149 mg, 46%).

Step B: (1R,2R)-Methyl 2-(4-(4-bromophenyl)-2-(tert-butyl)thiazol-5-yl)cyclohexanecarboxlate To a solution of (1R,2R)-methyl 2-(2-(4-bromophenyl)-2-pivalamidoacetyl)cyclohexanecarboxylate (74 mg, 0.169 mmol) in toluene (2 mL) was added Lawesson's reagent (54.6 mg, 0.135 mmol, 0.8 eq). The resulting mixture was stirred at 80° C. for 1 hour. The reaction mixture was cooled to room temperature and quenched with saturated NaHCO$_3$. The resulting mixture was extracted with EtOAc (3×5 mL). Combined organic phases were dried over Na$_2$SO$_4$, filtered, and concentrate under reduced pressure. The residue was purified by flash chromatography (4 g, SiO$_2$): 3 to 15% EtOAc in hexanes giving 52 mg (71%) of the desired product as white solid.

Step C: (1R,2R)-2-(4-(4-Bromophenyl)-2-(tert-butyl)thiazol-5-yl)cyclohexanecarboxylic acid To a solution of (1R,2R)-methyl 2-(4-(4-bromophenyl)-2-(tert-butyl)thiazol-5-yl)cyclohexanecarboxylate (52 mg, 0.119 mmol) in MeOH/THF=1/1 (2 mL) was added 1 N NaOH solution. The resulting solution was stirred at 60° C. for 4.5 hours and at 40° C. for 18 hours. The reaction mixture was cooled to room temperature followed by the addition of 1 N HCl. The resulting mixture was concentrated giving the desired product as a white solid. The crude product was used without further purification.

Step D: (1R,2R)-2-(4-(4-Bromophenyl)-2-(tert-butyl)thiazol-5-yl)-N-(1-cyanocyclopropyl)cyclohexanecarboxamide To a solution of (1R,2R)-2-(4-(4-bromophenyl)-2-(tert-butyl)thiazol-5-yl)cyclohexanecarboxylic acid (50 mg, 0.188 mmol) and HATU (67.5 mg, 0.178 mmol) in DMF (2 mL) was added 1-cyanocyclopropanaminium chloride (35 mg, 0.296 mmol) followed by the addition of DIEA (0.103 mL, 0.592 mmol). The resulting mixture was stirred at 40° C. for 18 hours. The resulting solution was filtered and directly purified by reverse phase HPLC (Sunfire C18 30×150 mm column; 30 to 90% MeCN in water, 0.1% TFA modifier for MeCN and water) to give the desired product as a white solid (49 mg, 85%).

Step E: (1R,2R)-2-(2-(tert-Butyl)-4-(4-(1,1-dioxidothiomorpholino)phenyl)thiazol-5-yl)-N-(1-cyanocyclopropyl)cyclohexanecarboxamide (Compound 10)

To a mixture of (1R,2R)-2-(4-(4-bromophenyl)-2-(tert-butyl)thiazol-5-yl)-N-(1-cyanocyclopropyl)cyclohexanecarboxamide (25 mg, 0.051 mmol), thiomorpholine 1,1-dioxide (20.84 mg, 0.154 mmol, 3 eq), chloro(2-dicyclohexylphosphino-2',4',6'-triisopropyl-1,1'-biphenyl)[2-(2-aminoethyl)phenyl)]palladium(II) (3.8 mg, 5.14 μmol, 0.1 eq), and K$_3$PO$_4$.H$_2$O (14.2 mg, 0.062 mmol) in a vial under N$_2$ was added THF (0.7 mL). The vial was sealed and the resulting mixture was heated at 100° C. for 4 h and then left at room temperature for 18 hours. The reaction mixture was concentrated under reduced pressure, the residue was dissolved in DMSO, and the solution was purified by reverse phase HPLC (Sunfire C18 30×150 mm column; 5 to 95% MeCN in water. 0.1% TFA modifier for MeCN and water) giving 24.5 mg (73%) of the desired product (Compound 9) as a white solid. MS (ES, m/z): 541.1 (M+1); $^1$H NMR (400 MHz, CDCl$_3$) 7.48 (d, J=8.6 Hz, 2H), 6.97 (d, J=8.6, 2H), 6.16 (s, 1H), 3.95-3.92 (m, 4H), 3.30-3.25 (m, 1H), 3.12-

3.09 (m, 4H), 2.24-2.17 (m, 1H), 2.01-1.79 (m, 4H), 1.51-1.56 (m, 1H).

The following compounds were prepared using methods analogous to those described in the preceding examples:

| | Structure | Name | LC-MS m/z (M + H) | hrbC at K IP (nM) | hCat F IP (nM) |
|---|---|---|---|---|---|
| 1 | 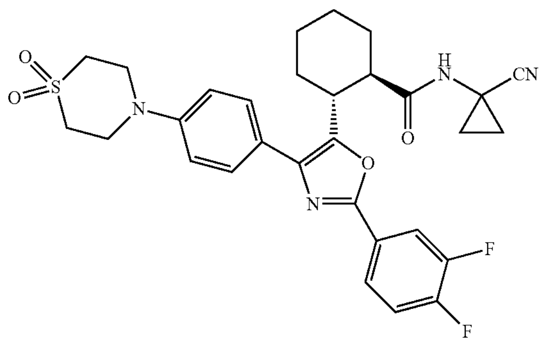 [SMILES: N#CC1(NC(=O)[C@@H]2CCCC[C@H]2c2oc(-c3ccc(F)c(F)c3)nc2-c2ccc(N3CCS(=O)(=O)CC3)cc2)CC1] | (1R,2R)-N-(1-cyanocyclopropyl)-2-(2-(3,4-difluorophenyl)-4-(4-(1,1-dioxidothiomorpholino)phenyl)oxazol-5-yl)cyclohexanecarboxamide | 581.1 | 0.39 | 573 |
| 2 | 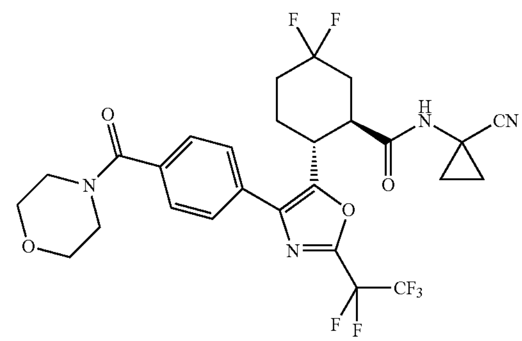 [SMILES: N#CC1(NC(=O)[C@@H]2CC(F)(F)CC[C@H]2c2oc(C(F)(F)C(F)(F)F)nc2-c2ccc(C(=O)N3CCOCC3)cc2)CC1] | (1R,2R)-N-(1-cyanocyclopropyl)-5,5-difluoro-2-(4-(4-(morpholine-4-carbonyl)phenyl)-2-(perfluoroethyl)oxazol-5-yl)cyclohexanecarboxamide | 603.0 | 1.04 | 306 |
| 3 | 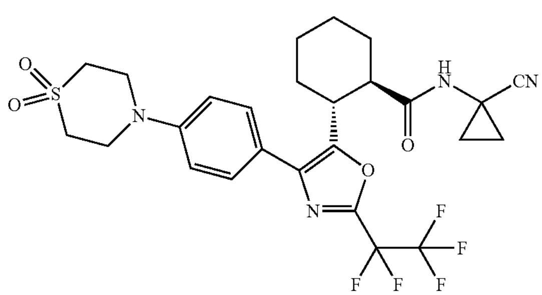 [SMILES: N#CC1(NC(=O)[C@@H]2CCCC[C@H]2c2oc(C(F)(F)C(F)(F)F)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(perfluoroethyl)oxazol-5-yl)cyclohexanecarboxamide | 587.5 | 1.02 | 666 |
| 4 | 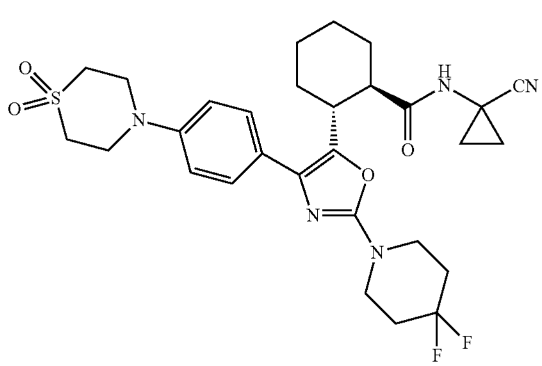 [SMILES: N#CC1(NC(=O)[C@@H]2CCCC[C@H]2c2oc(N3CCC(F)(F)CC3)nc2-c2ccc(N3CCS(=O)(=O)CC3)cc2)CC1] | (1R,2R)-N-(1-cyanocyclopropyl)-2-(2-(4,4-difluoropiperidin-1-yl)-4-(4-(1,1-dioxidothiomorpholino)phenyl)oxazol-5-yl)cyclohexanecarboxamide | 588.2 | 6.37 | 10,000 |

-continued

| | Structure | Name | LC-MS m/z (M + H) | hrbC at K IP (nM) | hCat F IP (nM) |
|---|---|---|---|---|---|
| 5 | 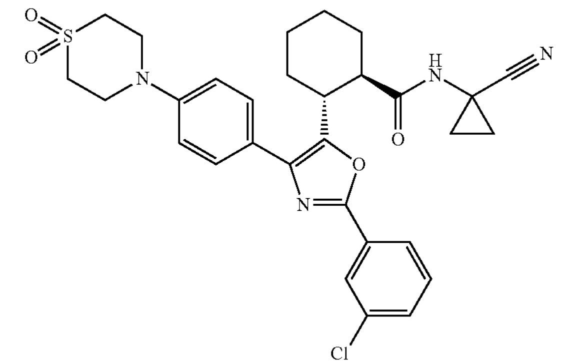 [SMILES: N#CC1(NC(=O)[C@@H]2CCCC[C@H]2c2oc(-c3cccc(Cl)c3)nc2-c2ccc(N3CCS(=O)(=O)CC3)cc2)CC1] | (1R,2R)-2-(2-(3-chlorophenyl)-4-(4-(1,1-dioxidothiomorpholino)phenyl)oxazol-5-yl)-N-(1-cyanocyclopropyl)cyclohexanecarboxamide | 581.3 | 0.56 | 507 |
| 6 | 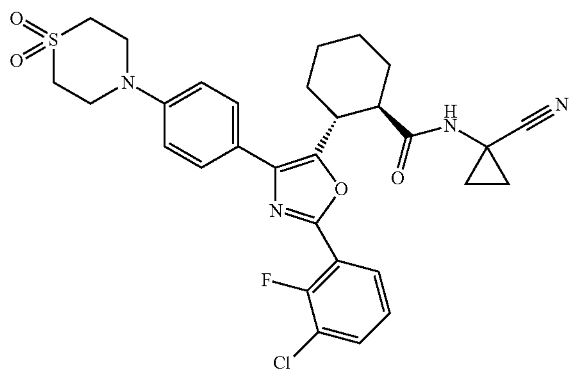 [SMILES: N#CC1(NC(=O)[C@@H]2CCCC[C@H]2c2oc(-c3cccc(Cl)c3F)nc2-c2ccc(N3CCS(=O)(=O)CC3)cc2)CC1] | (1R,2R)-2-(2-(3-chloro-2-fluorophenyl)-4-(4-(1,1-dioxidothiomorpholino)phenyl)oxazol-5-yl)-N-(1-cyanocyclopropyl)cyclohexanecarboxamide | 599.3 | 0.48 | 631 |
| 7 | 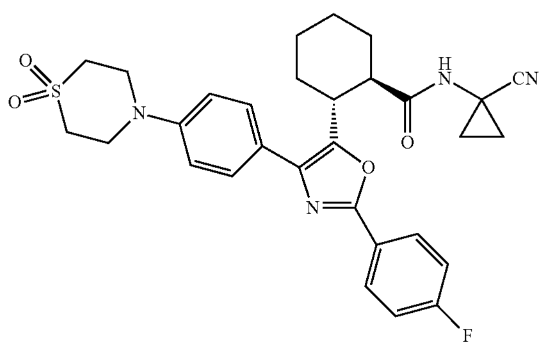 [SMILES: N#CC1(NC(=O)[C@@H]2CCCC[C@H]2c2oc(-c3ccc(F)cc3)nc2-c2ccc(N3CCS(=O)(=O)CC3)cc2)CC1] | (1R,2R)-N-(1-Cyanocyclopropyl)-2-{4-[4-(1,1-dioxo-1λ⁶-thiomorpholin-4-yl)phenyl]-2-(4-fluorophenyl)-1,3-oxazol-5-yl}cyclohexanecarboxamide | 563.1 | 1.49 | 840 |
| 8 | 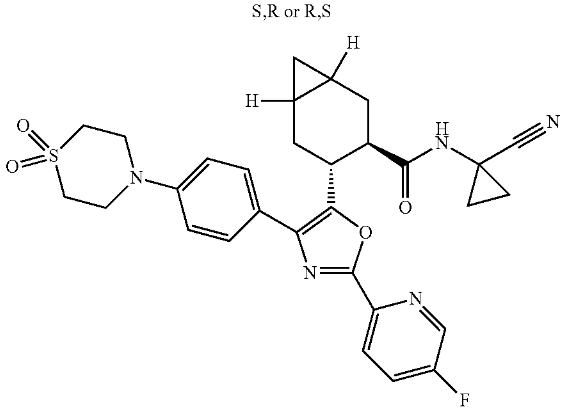 [SMILES: N#CC1(NC(=O)[C@@H]2CC3CC3C[C@H]2c2oc(-c3ccc(F)cn3)nc2-c2ccc(N3CCS(=O)(=O)CC3)cc2)CC1] | (1S,3R,4R,6R or 1R,3R,4R,6S)-N-(1-Cyanocyclopropyl)-4-(4-(4-(1,1-dioxidothiomorpholino)phenyl)-2-(5-fluoropyridin-2-yl)oxazol-5-yl)bicyclo[4.1.0]heptane-3-carboxamide | 576.0 | 9.56 | 1,616 |

-continued

| | Structure | Name | LC-MS m/z (M + H) | hrbC at K IP (nM) | hCat F IP (nM) |
|---|---|---|---|---|---|
| 9 | R,S or S,R 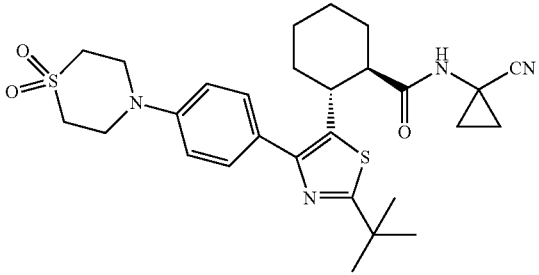 [SMILES: CC(C)(C)c1nc(-c2ccc(N3CCS(=O)(=O)CC3)cc2)c([C@@H]2CCCC[C@H]2C(=O)NC2(C#N)CC2)s1] | (1R,3R,4R,6S or 1S,3R,4R,6R)-N-(1-cyanocyclopropyl)-4-(4-(4-(1,1-dioxidothiomorpholino)phenyl)-2-(5-fluoropyridin-2-yl)oxazol-5-yl)bicyclo[4.1.0]heptane-3-carboxamide | 576.0 | 3.54 | 1,176 |
| 10 | 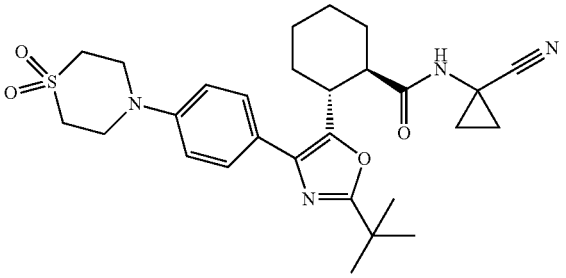 [SMILES: CC(C)(C)c1nc(-c2ccc(N3CCS(=O)(=O)CC3)cc2)c([C@@H]2CCCC[C@H]2C(=O)NC2(C#N)CC2)o1] | (1R,2R)-2-(2-(tert-butyl)-4-(4-(1,1-dioxidothiomorpholino)phenyl)thiazol-5-yl)-N-(1-cyanocyclopropyl)cyclohexanecarboxamide | 541.1 | 1.65 | 1,438 |
| 11 | 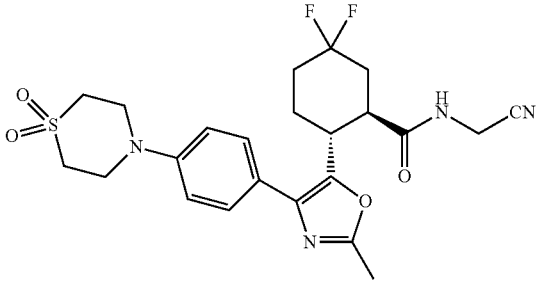 [SMILES: Cc1nc(-c2ccc(N3CCS(=O)(=O)CC3)cc2)c([C@@H]2CCC(F)(F)C[C@H]2C(=O)NCC#N)o1] | (1R,2R)-2-(2-(tert-butyl)-4-(4-(1,1-dioxidothiomorpholino)phenyl)oxazol-5-yl)-N-(1-cyanocyclopropyl)cyclohexanecarboxamide | 525.3 | 0.69 | 681 |
| 12 | 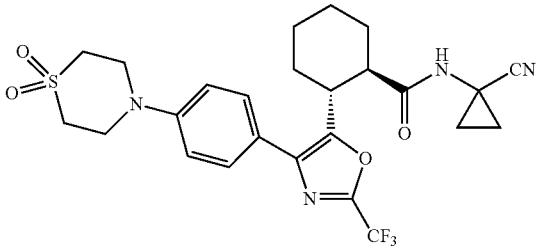 | (1R,2R)-N-(cyanomethyl)-2-(4-(4-(1,1-dioxidothiomorpholino)phenyl)-2-methyloxazol-5-yl)-5,5-difluorocyclohexanecarboxamide | 493.1 | 0.29 | 327 |
| 13 | 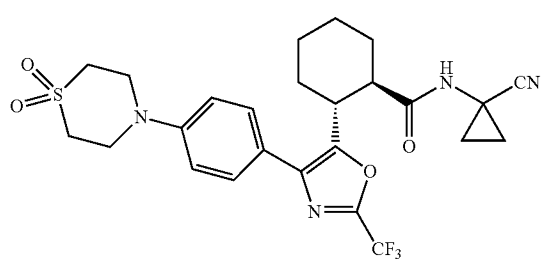 [SMILES: N#CC1(NC(=O)[C@@H]2CCCC[C@H]2c2oc(C(F)(F)F)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(trifluoromethyl)oxazol-5-yl)cyclohexanecarboxamide | 537.0 | 0.46 | 628 |

-continued

| | Structure | Name | LC-MS m/z (M + H) | hrbC at K IP (nM) | hCat F IP (nM) |
|---|---|---|---|---|---|
| 14 | 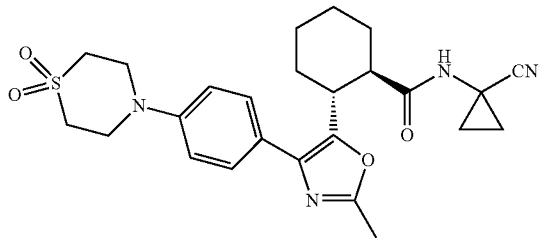 | (1R,2R)-N-(1-cyanocyclopropyl)-2-(4-(4-(1,1-dioxidothiomorpholino)phenyl)-2-methyloxazol-5-yl)cyclohexanecarboxamide | 483.1 | 1.08 | 1,326 |
| 15 | 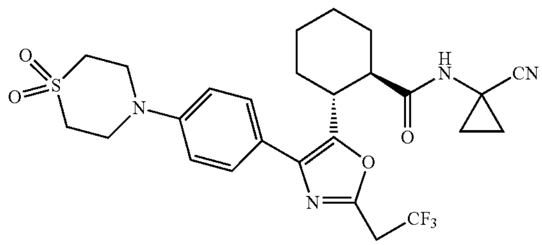 [SMILES: N#CC1(NC(=O)[C@@H]2CCCC[C@H]2c2oc(CC(F)(F)F)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(2,2,2-trifluoroethyl)oxazol-5-yl)cyclohexanecarboxamide | 551.0 | 1.80 | 640 |
| 16 | 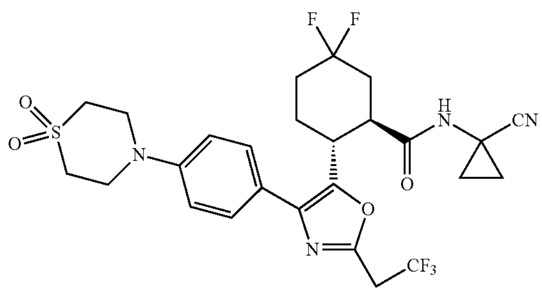 [SMILES: N#CC1(NC(=O)[C@@H]2CC(F)(F)CC[C@H]2c2oc(CC(F)(F)F)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(2,2,2-trifluoroethyl)oxazol-5-yl)-5,5-difluorocyclohexane-carboxamide | 587.0 | 0.61 | 209 |
| 17 | 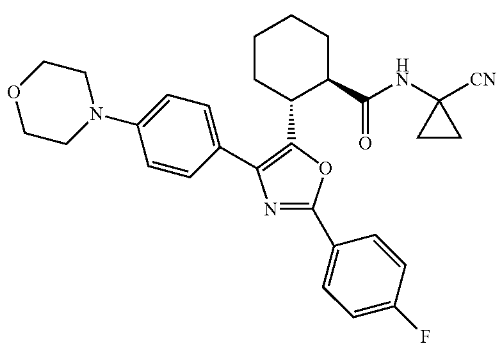 [SMILES: N#CC1(NC(=O)[C@@H]2CCCC[C@H]2c2oc(-c3ccc(F)cc3)nc2-c2ccc(N3CCOCC3)cc2)CC1] | (1R,2R)-N-(1-cyanocyclopropyl)-2-(2-(4-fluorophenyl)-4-(4-morpholinophenyl)oxazol-5-yl)cyclohexanecarboxamide | 515.0 | 9.36 | 499 |
| 18 | 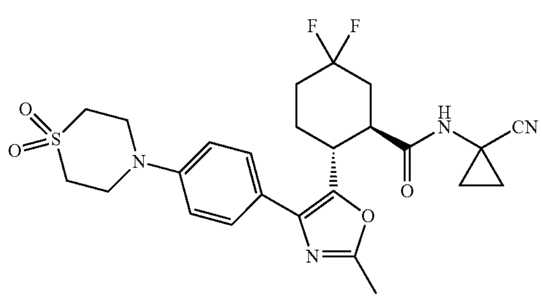 [SMILES: Cc1nc(-c2ccc(N3CCS(=O)(=O)CC3)cc2)c([C@@H]2CCC(F)(F)C[C@H]2C(=O)NC2(C#N)CC2)o1] | (1R,2R)-N-(1-cyanocyclopropyl)-2-(4-(4-(1,1-dioxidothiomorpholino)phenyl)-2-methyloxazol-5-yl)-5,5-difluorocyclohexane-carboxamide | 519.0 | 0.48 | 178 |

-continued

| | Structure | Name | LC-MS m/z (M + H) | hrbC at K IP (nM) | hCat F IP (nM) |
|---|---|---|---|---|---|
| 19 | 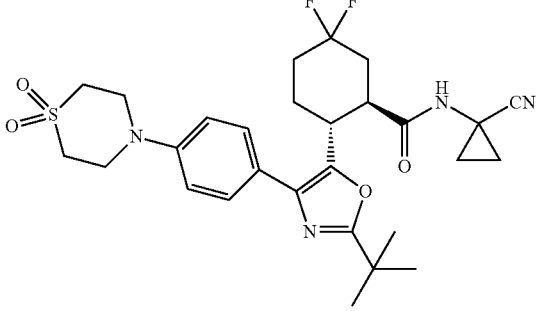 | (1R,2R)-2-(2-(tert-butyl)-4-(4-(1,1-dioxidothiomorpholino)phenyl)oxazol-5-yl)-N-(1-cyanocyclopropyl)-5,5-difluorocyclohexane-carboxamide | 561.1 | 0.54 | 81 |
| 20 | 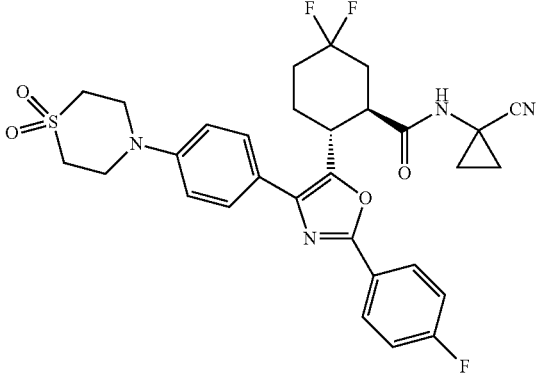 [SMILES: N#CC1(NC(=O)[C@@H]2CC(F)(F)CC[C@H]2c2oc(-c3ccc(F)cc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(4-fluorophenyl)oxazol-5-yl)-5,5-difluorocyclohexane-carboxamide | 599.0 | 0.28 | 71 |
| 21 | 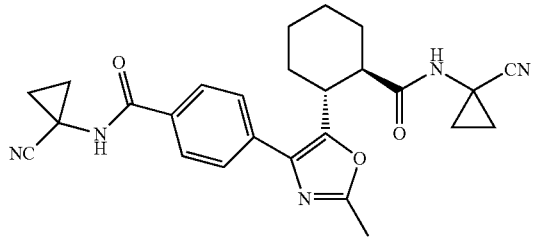 [SMILES: Cc1nc(-c2ccc(C(=O)NC3(C#N)CC3)cc2)c([C@@H]2CCCC[C@H]2C(=O)NC2(C#N)CC2)o1] | N-(1-cyanocyclopropyl)-4-(5-((1R,2R)-2-((1-cyanocyclopropyl)carbamoyl)cyclohexyl)-2-methyloxazol-4-yl)benzamide | 458.0 | 61.87 | 10,000 |
| 22 | 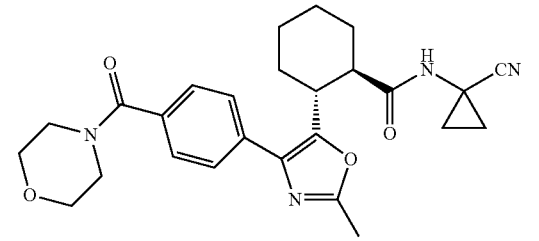 [SMILES: Cc1nc(-c2ccc(C(=O)N3CCOCC3)cc2)c([C@@H]2CCCC[C@H]2C(=O)NC2(C#N)CC2)o1] | (1R,2R)-N-(1-cyanocyclopropyl)-2-(2-methyl-4-(4-(morpholine-4-carbonyl)phenyl)oxazol-5-yl)cyclohexanecarboxamide | 463.1 | 5.09 | 6,158 |
| 23 | 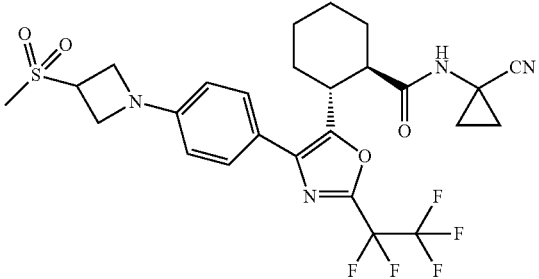 [SMILES: CS(=O)(=O)C1CN(c2ccc(-c3nc(C(F)(F)C(F)(F)F)oc3[C@@H]3CCCC[C@H]3C(=O)NC3(C#N)CC3)cc2)C1] | (1R,2R)-N-(1-cyanocyclopropyl)-2-(4-(4-(3-(methylsulfonyl)azetidin-1-yl)phenyl)-2-(perfluoroethyl)oxazol-5-yl)cyclohexanecarboxamide | 587.0 | 0.62 | 383 |

| | Structure | Name | LC-MS m/z (M + H) | hrbC at K IP (nM) | hCat F IP (nM) |
|---|---|---|---|---|---|
| 24 | 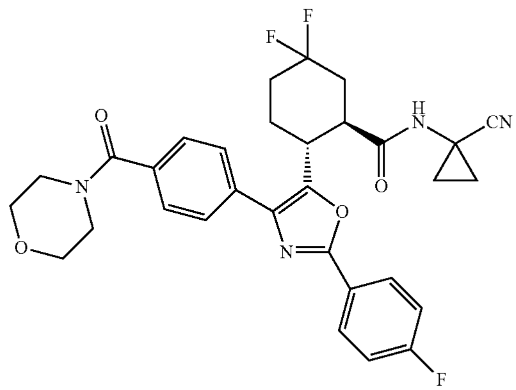 [SMILES: N#CC1(NC(=O)[C@@H]2CC(F)(F)CC[C@H]2c2oc(-c3ccc(F)cc3)nc2-c2ccc(C(=O)N3CCOCC3)cc2)CC1] | (1R,2R)-N-(1-cyanocyclopropyl)-5,5-difluoro-2-(2-(4-fluorophenyl)-4-(4-(morpholine-4-carbonyl)phenyl)oxazol-5-yl)cyclohexanecarboxamide | 579.1 | 0.68 | 181 |
| 25 | 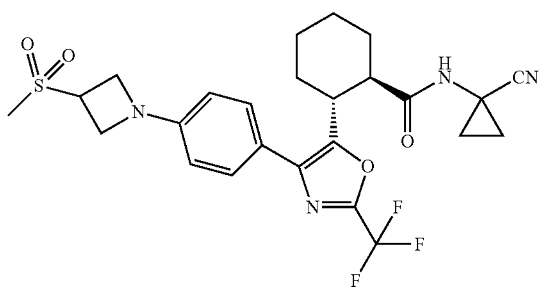 [SMILES: CS(=O)(=O)C1CN(c2ccc(-c3nc(C(F)(F)F)oc3[C@@H]3CCCC[C@H]3C(=O)NC3(C#N)CC3)cc2)C1] | (1R,2R)-N-(1-cyanocyclopropyl)-2-(4-(4-(3-(methylsulfonyl)azetidin-1-yl)phenyl)-2-(trifluoromethyl)oxazol-5-yl)cyclohexanecarboxamide yl)cyclohexanecarboxamide | 537.0 | 0.66 | 447 |
| 26 | 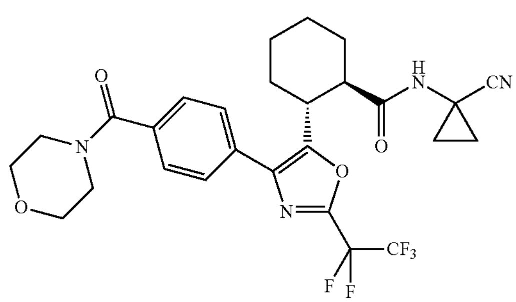 [SMILES: N#CC1(NC(=O)[C@@H]2CCCC[C@H]2c2oc(C(F)(F)C(F)(F)F)nc2-c2ccc(C(=O)N3CCOCC3)cc2)CC1] | (1R,2R)-N-(1-cyanocyclopropyl)-2-(4-(4-(morpholine-4-carbonyl)phenyl)-2-(perfluoroethyl)oxazol-5-yl)cyclohexanecarboxamide | 567.1 | 3.64 | 2,957 |
| 27 | 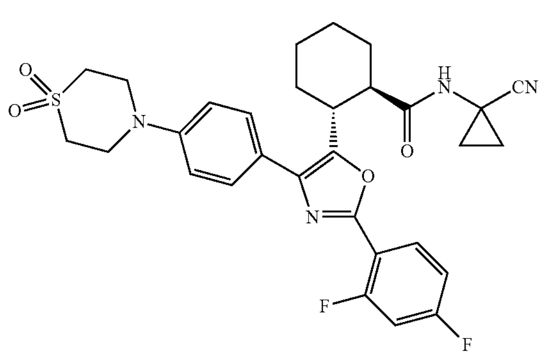 [SMILES: N#CC1(NC(=O)[C@@H]2CCCC[C@H]2c2oc(-c3ccc(F)cc3F)nc2-c2ccc(N3CCS(=O)(=O)CC3)cc2)CC1] | (1R,2R)-N-(1-cyanocyclopropyl)-2-(2-(2,4-difluorophenyl)-4-(4-(1,1-dioxidothiomorpholino)phenyl)oxazol-5-yl)cyclohexanecarboxamide | 581.1 | 0.37 | 681 |

|  | Structure | Name | LC-MS m/z (M + H) | hrbC at K IP (nM) | hCat F IP (nM) |
|---|---|---|---|---|---|
| 28 | 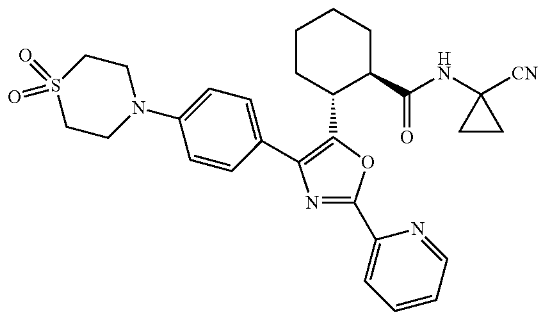 | (1R,2R)-N-(1-cyanocyclopropyl)-2-(4-(4-(1,1-dioxidothiomorpholino)phenyl)-2-(pyridin-2-yl)oxazol-5-yl)cyclohexanecarboxamide | 546.1 | 1.26 | 1,365 |
| 29 | 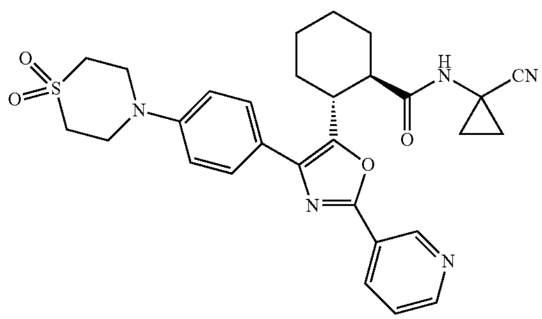 [SMILES: N#CC1(NC(=O)[C@@H]2CCCC[C@H]2c2oc(-c3cccnc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(pyridin-3-yl)oxazol-5-yl)cyclohexanecarboxamide | 546.1 | 0.48 | 565 |
| 30 | 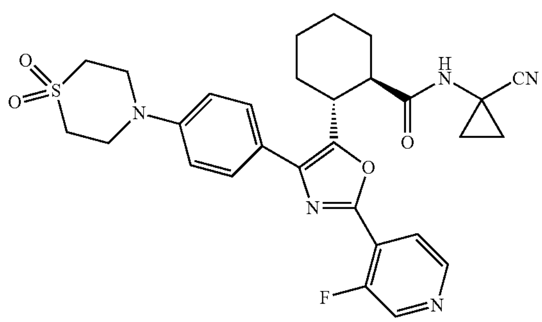 [SMILES: N#CC1(NC(=O)[C@@H]2CCCC[C@H]2c2oc(-c3ccncc3F)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(3-fluoropyridin-4-yl)oxazol-5-yl)cyclohcxanecarboxamide | 564.1 | 0.43 | 757 |
| 31 | 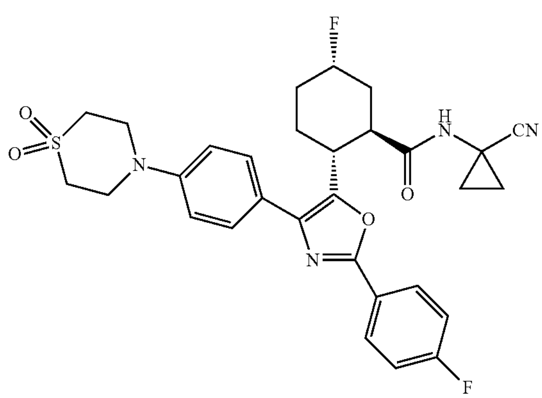 [SMILES: N#CC1(NC(=O)[C@@H]2C[C@@H](F)CC[C@H]2c2oc(-c3ccc(F)cc3)nc2-c2ccc(N3CCS(=O)(=O)CC3)cc2)CC1] | (1R,2R,5S)-N-(1-cyanocyclopropyl)-2-(4-(4-(1,1-dioxidothiomorpholino)phenyl)-2-(4-fluorophenyl)oxazol-5-yl)-5-fluorocyclohexane-carboxamide | 581.1 | 0.61 | 1,389 |

-continued

| | Structure | Name | LC-MS m/z (M + H) | hrbC at K IP (nM) | hCat F IP (nM) |
|---|---|---|---|---|---|
| 32 | 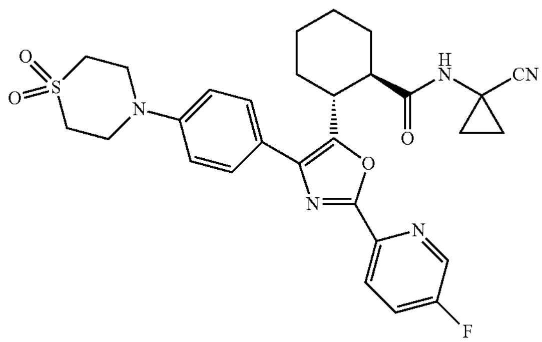 | (1R,2R)-N-(1-cyanocyclopropyl)-2-(4 (4-(1,1-dioxidothiomorpholino) phenyl)-2-(5-fluoropyridin-2-yl)oxazol-5-yl)cyclohexanecarboxamide | 564.1 | 3.12 | 2,493 |
| 33 | 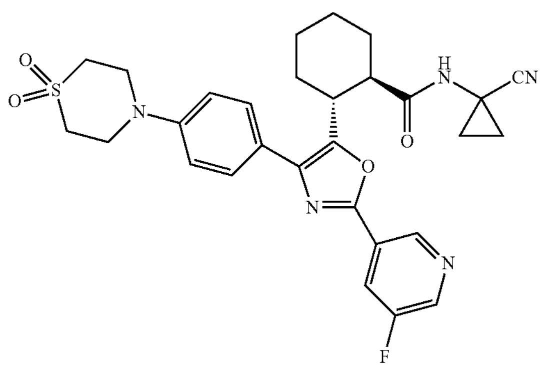 [SMILES: N#CC1(NC(=O)[C@@H]2CCCC[C@H]2c2oc(-c3cncc(F)c3)nc2-c2ccc(N3CCS(=O)(=O)CC3)cc2)CC1] | (1R,2R)-N-(1-cyanocyclopropyl)-2-(4-(4-(1,1-dioxidothiomorpholino) phenyl)-2-(5-fluoropyridin-3-yl)oxazol-5-yl)cyclohexanecarboxamide | 564.2 | 1.99 | 1,324 |
| 34 | 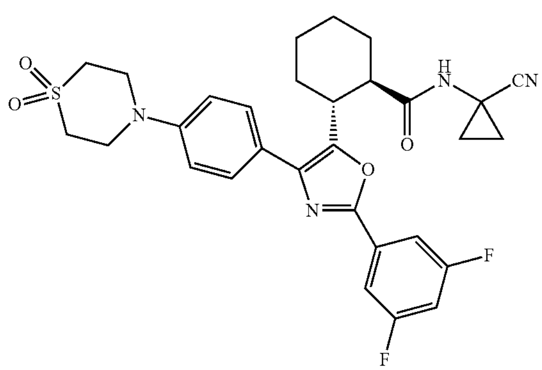 [SMILES: N#CC1(NC(=O)[C@@H]2CCCC[C@H]2c2oc(-c3cc(F)cc(F)c3)nc2-c2ccc(N3CCS(=O)(=O)CC3)cc2)CC1] | (1R,2R)-N-(1-cyanocyclopropyl)-2-(2-(3,5-difluorophenyl)-4-(4-(1,1-dioxidothiomorpholino) phenyl)oxazol-5-yl) cyclohexanecarboxamide | 581.1 | 0.85 | 442 |
| 35 | 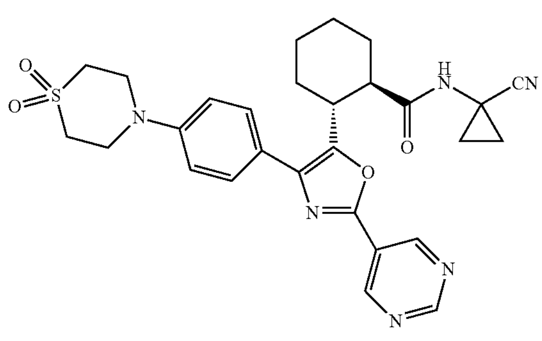 [SMILES: N#CC1(NC(=O)[C@@H]2CCCC[C@H]2c2oc(-c3cncnc3)nc2-c2ccc(N3CCS(=O)(=O)CC3)cc2)CC1] | (1R,2R)-N-(1-cyanocyclopropyl)-2-(4-(4-(1,1-dioxidothiomorpholino) phenyl)-2-(pyrimidin-5-yl)oxazol-5-yl) cyclohexanecarboxamide | 547.1 | 1.11 | 993 |

-continued

| | Structure | Name | LC-MS m/z (M + H) | hrbC at K IP (nM) | hCat F IP (nM) |
|---|---|---|---|---|---|
| 36 | 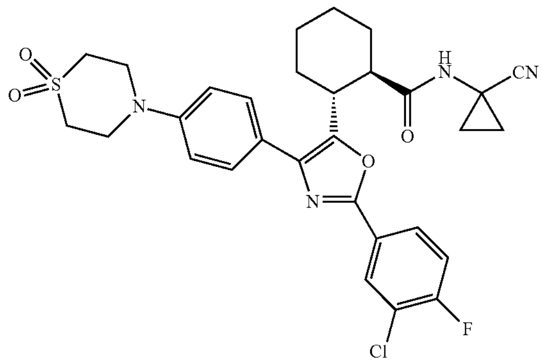 [SMILES: N#CC1(NC(=O)[C@@H]2CCCC[C@H]2c2oc(-c3ccc(F)c(Cl)c3)nc2-c2ccc(N3CCS(=O)(=O)CC3)cc2)CC1] | (1R,2R)-2-(2-(3-chloro-4-fluorophenyl)-4-(4-(1,1-dioxidothiomorpholino)phenyl)oxazol-5-yl)-N-(1-cyanocyclopropyl)cyclohexanecarboxamide | 597.2 | 0.94 | 382 |
| 37 | 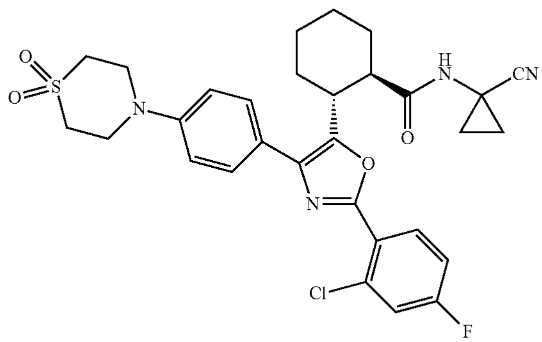 | (1R,2R)-2-(2-(2-chloro-4-fluorophenyl)-4-(4-(1,1-dioxidothiomorpholino)phenyl)oxazol-5-yl)-N-(1-cyanocyclopropyl)cyclohexanecarboxamide | 597.1 | 0.72 | 353 |
| 38 | 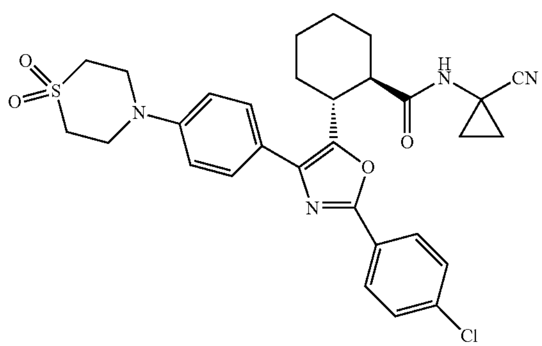 | (1R,2R)-2-(2-(4-chlorophenyl)-4-(4-(1,1-dioxidothiomorpholino)phenyl)oxazol-5-yl)-N-(1-cyanocyclopropyl)cyclohexanecarboxamide | 579.2 | 1.28 | 308 |
| 39 | 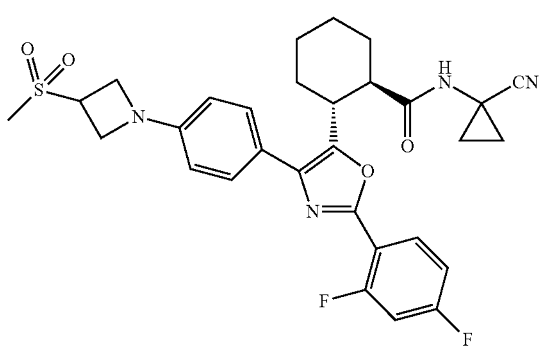 [SMILES: CS(=O)(=O)C1CN(c2ccc(-c3nc(-c4ccc(F)cc4F)oc3[C@@H]3CCCC[C@H]3C(=O)NC3(C#N)CC3)cc2)C1] | (1R,2R)-N-(1-cyanocyclopropyl)-2-(2-(2,4-difluorophenyl)-4-(4-(3-(methylsulfonyl)azetidin-1-yl)phenyl)oxazol-5-yl)cyclohexanecarboxamide | 581.1 | 2.11 | 702 |

-continued

| | Structure | Name | LC-MS m/z (M + H) | hrbC at K IP (nM) | hCat F IP (nM) |
|---|---|---|---|---|---|
| 40 | 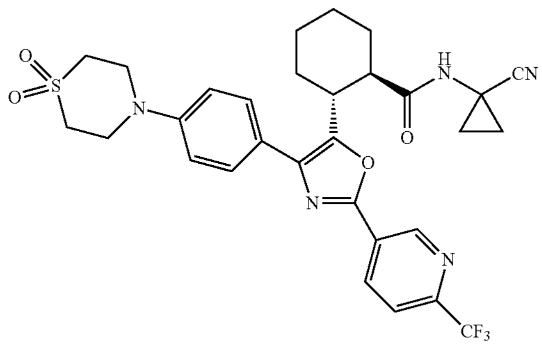 [SMILES: N#CC1(NC(=O)[C@@H]2CCCC[C@H]2c2oc(-c3ccc(C(F)(F)F)nc3)nc2-c2ccc(N3CCS(=O)(=O)CC3)cc2)CC1] | (1R,2R)-N-(1-cyanocyclopropyl)-2-(4-(4-(1,1 dioxidothiomorpholino)phenyl)-2-(6-(trifluoromethyl)pyridin-3-yl)oxazol-5-yl)cyclohexane carboxamide | 614.2 | 1.42 | 2,218 |
| 41 | 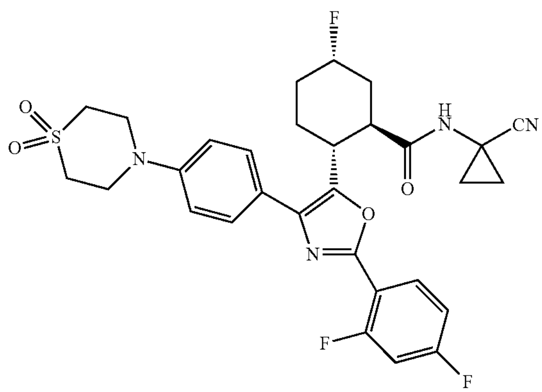 [SMILES: N#CC1(NC(=O)[C@@H]2C[C@@H](F)CC[C@H]2c2oc(-c3ccc(F)cc3F)nc2-c2ccc(N3CCS(=O)(=O)CC3)cc2)CC1] | (1R,2R,5S)-N-(1-cyanocyclopropyl)-2-(2-(2,4-difluorophenyl)-4-(4-(1,1-dioxidothiomorpholino)phenyl)oxazol-5-yl)-5-fluorocyclohexane-carboxamide | 599.2 | 1.41 | 2,190 |
| 42 | 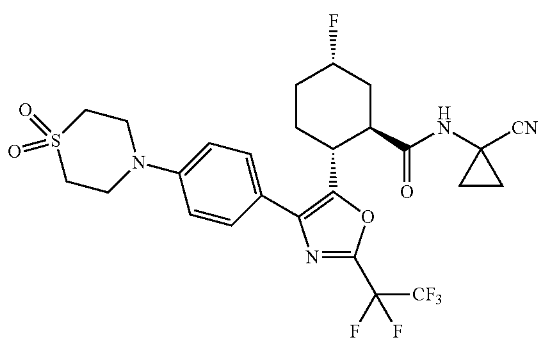 [SMILES: N#CC1(NC(=O)[C@@H]2C[C@@H](F)CC[C@H]2c2oc(C(F)(F)C(F)(F)F)nc2-c2ccc(N3CCS(=O)(=O)CC3)cc2)CC1] | (1R,2R,5S)-N-(1-cyanocyclopropyl)-2-(4-(4-(1,1-dioxidothiomorpholino)phenyl)-2-(perfluoroethyl)oxazol-5-yl)-5-fluorocyclohexane-carboxamide | 605.1 | 2.41 | 1,855 |
| 43 | 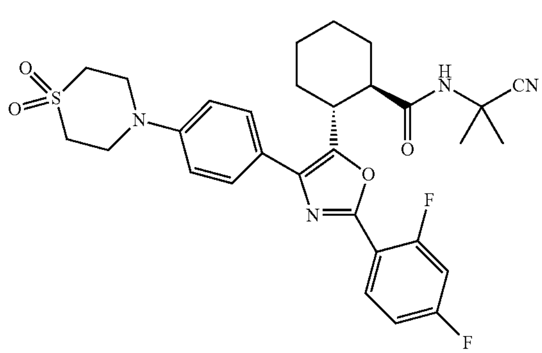 [SMILES: CC(C)(C#N)NC(=O)[C@@H]1CCCC[C@H]1c1oc(-c2ccc(F)cc2F)nc1-c1ccc(N2CCS(=O)(=O)CC2)cc1] | (1R,2R)-N-(2-cyanopropan-2-yl)-2-(2-(2,4-difluorophenyl)-4-(4-(1,1-dioxidothiomorpholino)phenyl)oxazol-5-yl)cyclohexanecarboxamide | 583.2 | 15.69 | 1,651 |

-continued

| | Structure | Name | LC-MS m/z (M + H) | hrbC at K IP (nM) | hCat F IP (nM) |
|---|---|---|---|---|---|
| 44 | 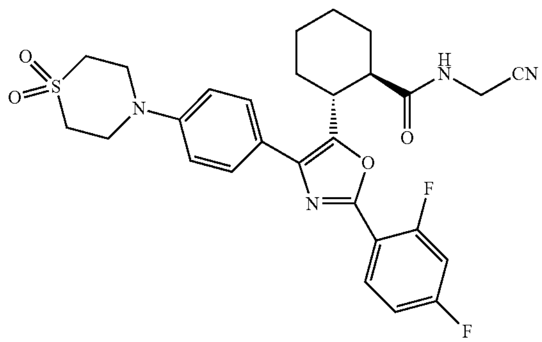 [SMILES: N#CCNC(=O)[C@@H]1CCCC[C@H]1c1oc(-c2ccc(F)cc2F)nc1-c1ccc(N2CCS(=O)(=O)CC2)cc1] | (1R,2R)-N-(cyanomethyl)-2-(2-(2,4-difluorophenyl)-4-(4-(1,1-dioxidothiomorpholino)phenyl)oxazol-5-yl)cyclohexanecarboxamide | 555.2 | 0.67 | 229 |
| 45 | 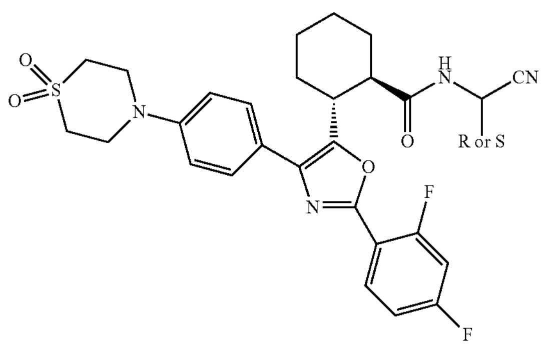 | (1R,2R)-N-((R or S)-1-cyanoethyl)-2-(2-(2,4-difluorophenyl)-4-(4-(1,1-dioxidothiomorpholino)phenyl)oxazol-5-yl)cyclohexanecarboxamide | 569.2 | 32.66 | 1,000 |
| 46 | 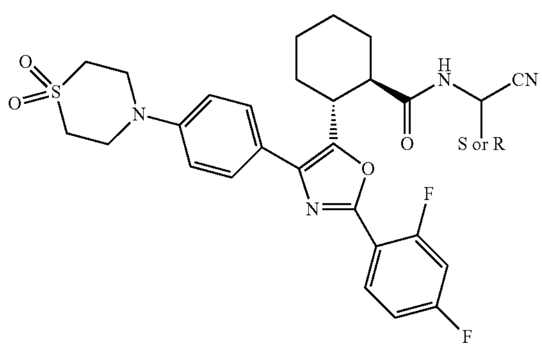 | (1R,2R)-N-((S or R)-1-cyanoethyl)-2-(2-(2,4-difluorophenyl)-4-(4-(1,1-dioxidothiomorpholino)phenyl)oxazol-5-yl)cyclohexanecarboxamide | 569.1 | 0.66 | 230 |
| 47 | 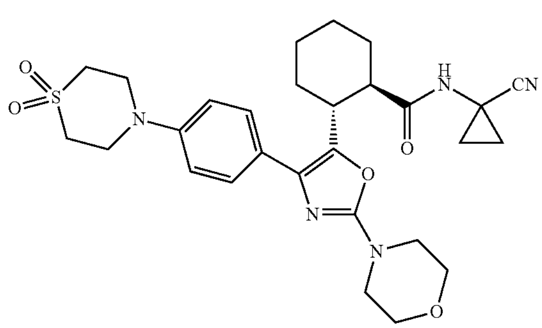 [SMILES: N#CC1(NC(=O)[C@@H]2CCCC[C@H]2c2oc(N3CCOCC3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-morpholinooxazol-5-yl)cyclohexanecarboxamide | 554.2 | 3.11 | 1,000 |

-continued

| | Structure | Name | LC-MS m/z (M + H) | hrbC at K IP (nM) | hCat F IP (nM) |
|---|---|---|---|---|---|
| 48 | 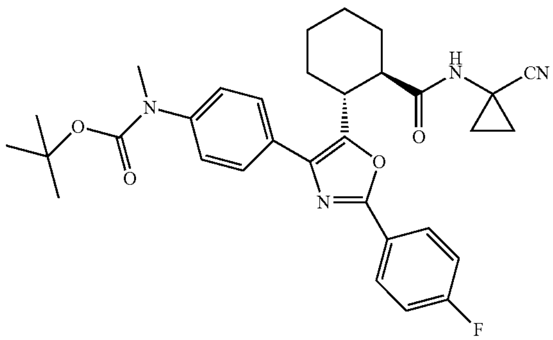 [SMILES: CN(C(=O)OC(C)(C)C)c1ccc(-c2nc(-c3ccc(F)cc3)oc2[C@@H]2CCCC[C@H]2C(=O)NC2(C#N)CC2)cc1] | tert-butyl (4-(5-(((1R,2R)-2-((1-cyanocyclopropyl)carbamoyl)cyclohexyl)-2-(4-fluorophenyl)oxazol-4-yl)phenyl)(methyl)carbamate | 559.2 | 7.40 | 176 |
| 49 | 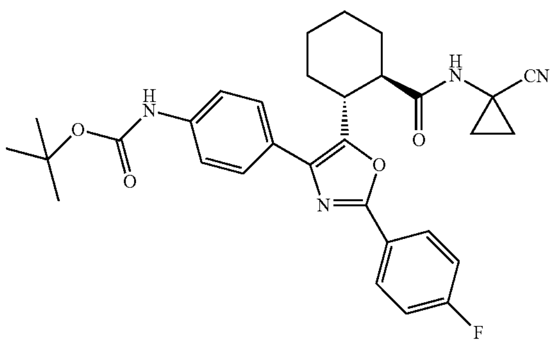 [SMILES: CC(C)(C)OC(=O)Nc1ccc(-c2nc(-c3ccc(F)cc3)oc2[C@@H]2CCCC[C@H]2C(=O)NC2(C#N)CC2)cc1] | tert-butyl (4-(5-(((1R,2R)-2-((1-cyanocyclopropyl)carbamoyl)cyclohexyl)-2-(4-fluorophenyl)oxazol-4-yl)phenyl)carbamate | 545.5 | 4.01 | 1,337 |
| 50 | 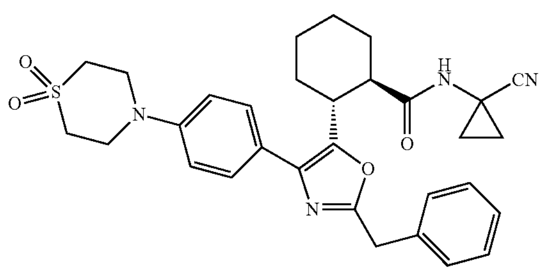 [SMILES: N#CC1(NC(=O)[C@@H]2CCCC[C@H]2c2oc(Cc3ccccc3)nc2-c2ccc(N3CCS(=O)(=O)CC3)cc2)CC1] | (1R,2R)-2-(2-benzyl-4-(4-(1,1-dioxidothiomorpholino)phenyl)oxazol-5-yl)-N-(1-cyanocyclopropyl)cyclohexanecarboxamide | 559.4 | 1.60 | 698 |
| 51 | 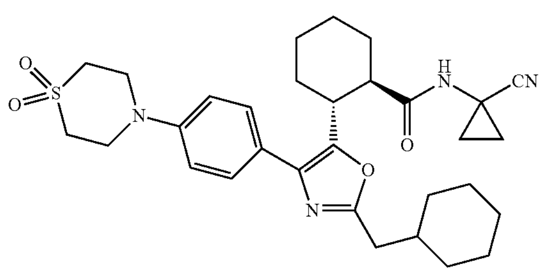 [SMILES: N#CC1(NC(=O)[C@@H]2CCCC[C@H]2c2oc(CC3CCCCC3)nc2-c2ccc(N3CCS(=O)(=O)CC3)cc2)CC1] | (1R,2R)-N-(1-cyanocyclopropyl)-2-(2-(cyclohexylmethyl)-4-(4-(1,1-dioxidothiomorpholino)phenyl)oxazol-5-yl)cyclohexanecarboxamide | 565.2 | 1.69 | 400 |

| | Structure | Name | LC-MS m/z (M + H) | hrbC at K IP (nM) | hCat F IP (nM) |
|---|---|---|---|---|---|
| 52 | 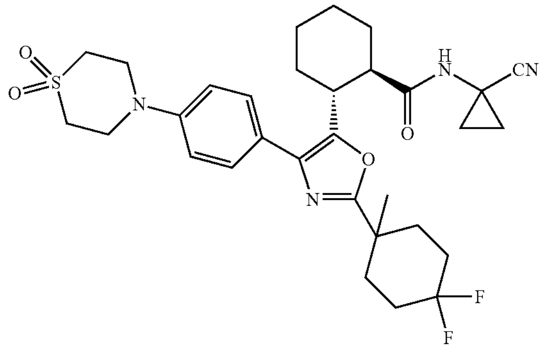 [SMILES: CC1(c2nc(-c3ccc(N4CCS(=O)(=O)CC4)cc3)c([C@@H]3CCCC[C@H]3C(=O)NC3(C#N)CC3)o2)CCC(F)(F)CC1] | (1R,2R)-N-(1-cyanocyclopropyl)-2-(2-(4,4-difluoro-1-methylcyclohexyl)-4-(4-(1,1-dioxidothiomorpholino)phenyl)oxazol-5-yl)cyclohexanecarboxamide | 601.2 | 2.51 | 820 |
| 53 | 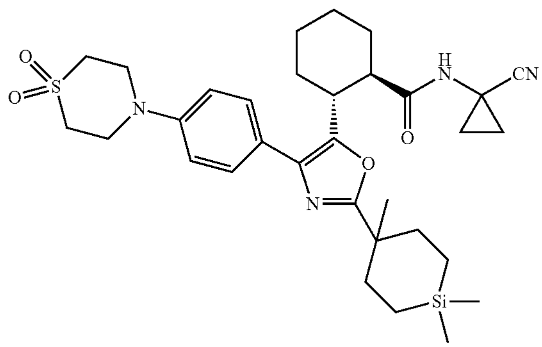 [SMILES: CC1(c2nc(-c3ccc(N4CCS(=O)(=O)CC4)cc3)c([C@@H]3CCCC[C@H]3C(=O)NC3(C#N)CC3)o2)CC[Si](C)(C)CC1] | (1R,2R)-N-(1-cyanocyclopropyl)-2-(4-(4-(1,1-dioxidothiomorpholino)phenyl)-2-(1,1,4-trimethylsilinan-4-yl)oxazol-5-yl)cyclohexanecarboxamide | 609.2 | 1.93 | 582 |
| 54 | 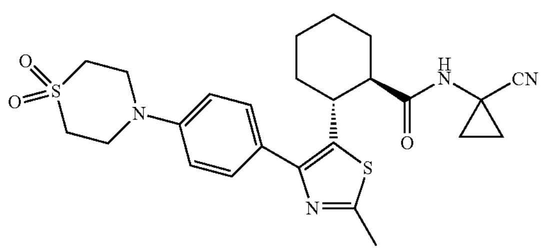 [SMILES: Cc1nc(-c2ccc(N3CCS(=O)(=O)CC3)cc2)c([C@@H]2CCCC[C@H]2C(=O)NC2(C#N)CC2)s1] | (1R,2R)-N-(1-cyanocyclopropyl)-2-(4-(4-(1,1-dioxidothiomorpholino)phenyl)-2-methylthiazol-5-yl)cyclohexanecarboxamide | 499.0 | 2.31 | 5,313 |
| 55 | 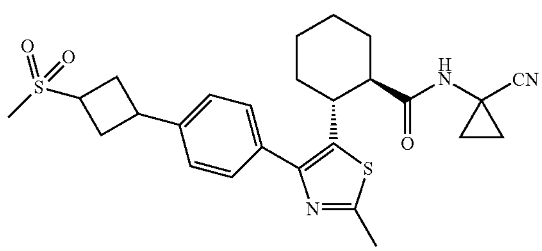 [SMILES: Cc1nc(-c2ccc(C3CC(S(C)(=O)=O)C3)cc2)c([C@@H]2CCCC[C@H]2C(=O)NC2(C#N)CC2)s1] | (1R,2R)-N-(1-cyanocyclopropyl)-2-(2-methyl-4-(4-(3-(methylsulfonyl)azetidin-1-yl)phenyl)thiazol-5-yl)cyclohexanecarboxamide | 499.0 | 4.15 | 5,480 |
| 56 | 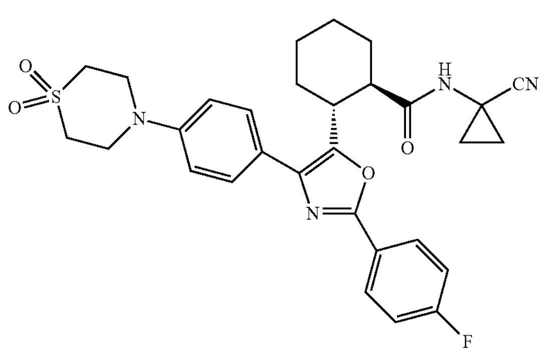 [SMILES: N#CC1(NC(=O)[C@@H]2CCCC[C@H]2c2oc(-c3ccc(F)cc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(4-fluorophenyl)thiazol-5-yl)cyclohexanecarboxamide | 579.1 | 3.19 | 722 |

-continued

| | Structure | Name | LC-MS m/z (M + H) | hrbC at K IP (nM) | hCat F IP (nM) |
|---|---|---|---|---|---|
| 57 | 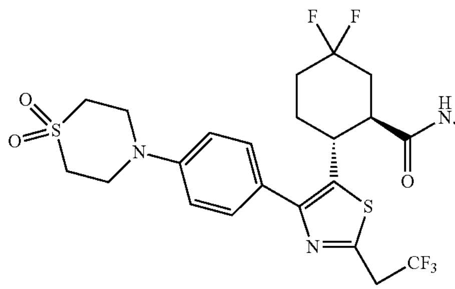 | (1R,2R)-N-(1-cyanocyclopropyl)-2-(4-(4-(1,1-dioxidothiomorpholino)phenyl)-2-(2,2,2-trifluoroethyl)thiazol-5-yl)-5,5-difluorocyclohexanecarboxamide | 603.0 | 0.58 | 93 |
| 58 | 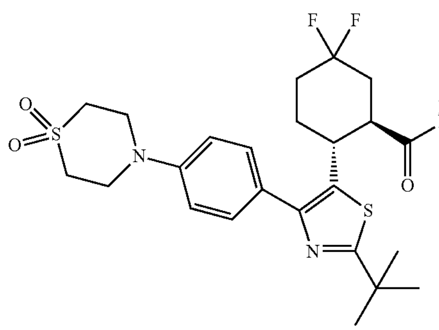 | (1R,2R)-2-(2-(tert-butyl)-4-(4-(1,1-dioxidothiomorpholino)phenyl)thiazol-5-yl)-N-(1-cyanocyclopropyl)-5,5-difluorocyclohexanecarboxamide | 577.1 | 0.67 | 72 |
| 59 | 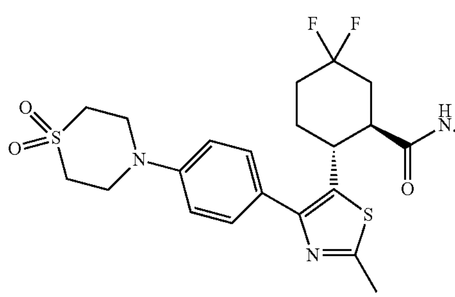 | (1R,2R)-N-(1-cyanocyclopropyl)-2-(4-(4-(1,1-dioxidothiomorpholino)phenyl)-2-methylthiazol-5-yl)-5,5-difluorocyclohexanecarboxamide | 535.0 | 0.51 | 389 |
| 60 | 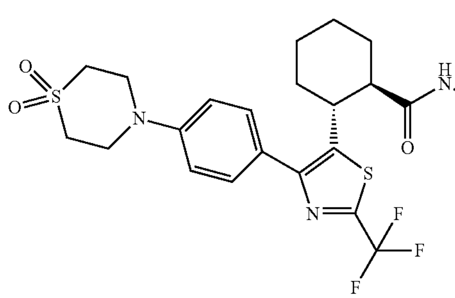 | (1R,2R)-N-(1-cyanocyclopropyl)-2-(4-(4-(1,1-dioxidothiomorpholino)phenyl)-2-(trifluoromethyl)thiazol-5-yl)cyclohexanecarboxamide | 553.0 | 4.37 | 3,290 |

-continued

| | Structure | Name | LC-MS m/z (M + H) | hrbC at K IP (nM) | hCat F IP (nM) |
|---|---|---|---|---|---|
| 61 | 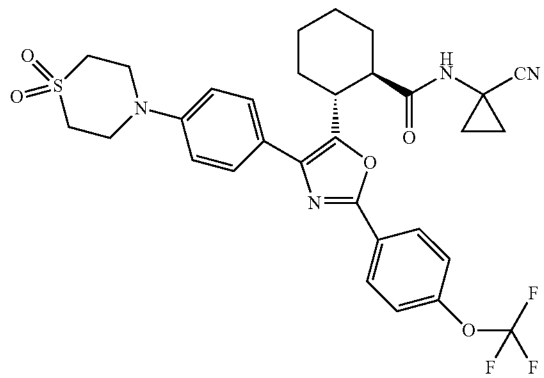 [SMILES: N#CC1(NC(=O)[C@@H]2CCCC[C@H]2c2oc(-c3ccc(OC(F)(F)F)cc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(4-(trifluoromethoxy)phenyl)oxazol-5-yl)cyclohexanecarboxamide | 629.4 | 1.36 | 511 |
| 62 | 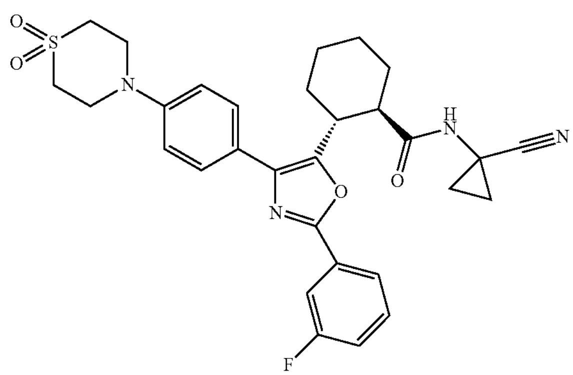 [SMILES: N#CC1(NC(=O)[C@@H]2CCCC[C@H]2c2oc(-c3cccc(F)c3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(3-fluorophenyl)oxazol-5-yl)cyclohexanecarboxamide | 563.3 | 0.92 | 492 |
| 63 | 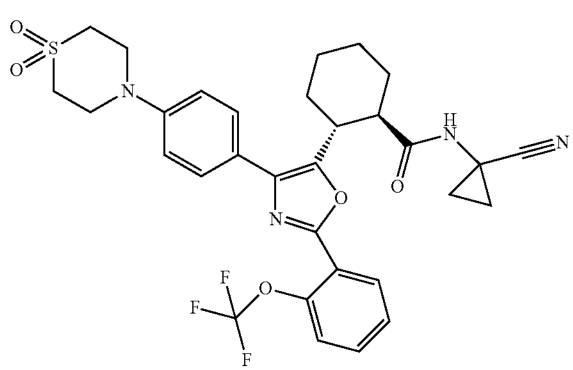 [SMILES: N#CC1(NC(=O)[C@@H]2CCCC[C@H]2c2oc(-c3ccccc3OC(F)(F)F)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(2-(trifluoromethoxy)phenyl)oxazol-5-yl)cyclohcxanecarboxamide | 629.3 | 1.23 | 639 |

| | Structure | Name | LC-MS m/z (M + H) | hrbC at K IP (nM) | hCat F IP (nM) |
|---|---|---|---|---|---|
| 64 | 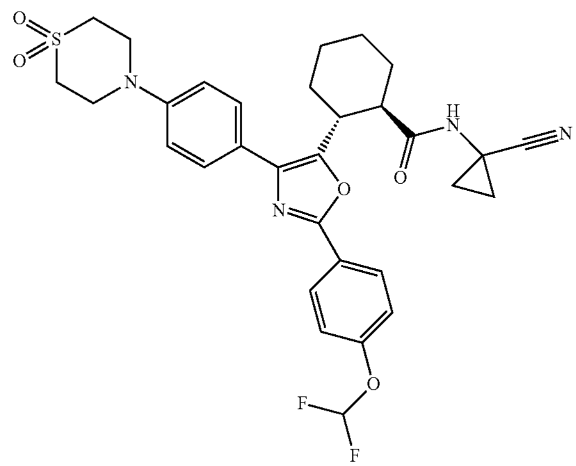 [SMILES: N#CC1(NC(=O)[C@@H]2CCCC[C@H]2c2oc(-c3ccc(OC(F)F)cc3)nc2-c2ccc(N3CCS(=O)(=O)CC3)cc2)CC1] | (1R,2R)-N-(1-cyanocyclopropyl)-2-(2-(4-(difluoromethoxy)phenyl)-4-(4-(1,1-dioxidothiomorpholino)phenyl)oxazol-5-yl)cyclohexanecarboxamide | 611.3 | 1.04 | 573 |
| 65 | 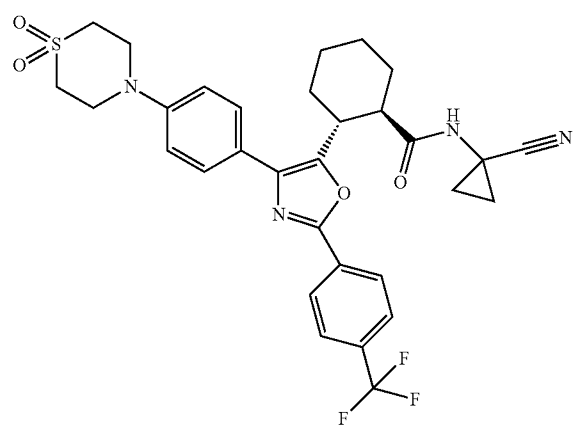 [SMILES: N#CC1(NC(=O)[C@@H]2CCCC[C@H]2c2oc(-c3ccc(C(F)(F)F)cc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(4-(trifluoromethyl)phenyl)oxazol-5-yl)cyclohexanecarboxamide | 613.3 | 1.30 | 825 |
| 66 | 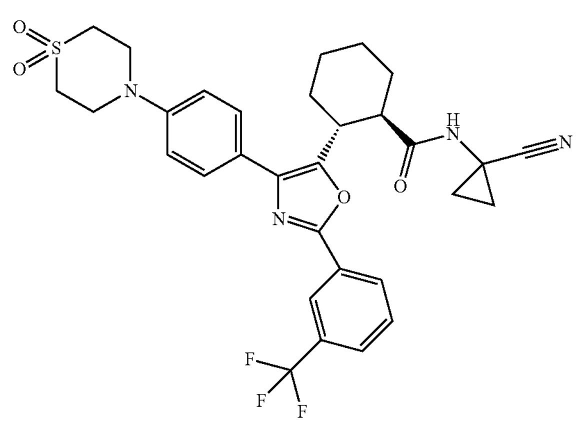 [SMILES: N#CC1(NC(=O)[C@@H]2CCCC[C@H]2c2oc(-c3cccc(C(F)(F)F)c3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(3-(trifluoromethyl)phenyl)oxazol-5-yl)cyclohexanecarboxamide | 613.3 | 1.21 | 454 |

-continued

| | Structure | Name | LC-MS m/z (M + H) | hrbC at K IP (nM) | hCat F IP (nM) |
|---|---|---|---|---|---|
| 67 | 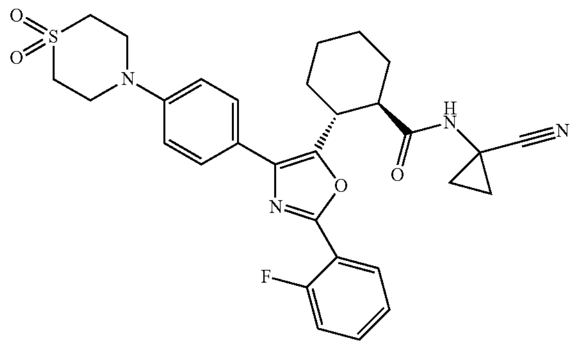 | (1R,2R)-N-(1-cyanocyclopropyl)-2-(4-(4-(1,1-dioxidothiomorpholino)phenyl)-2-(2-fluorophenyl)oxazol-5-yl)cyclohexanecarboxamide | 563.4 | 0.57 | 619 |
| 68 | 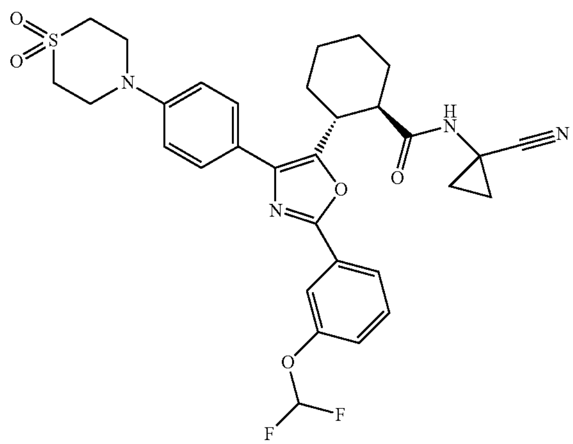 [SMILES: N#CC1(NC(=O)[C@@H]2CCCC[C@H]2c2oc(-c3cccc(OC(F)F)c3)nc2-c2ccc(N3CCS(=O)(=O)CC3)cc2)CC1] | (1R,2R)-N-(1-cyanocyclopropyl)-2-(2-(3-(difluoromethoxy)phenyl)-4-(4-(1,1-dioxidothiomorpholino)phenyl)oxazol-5-yl)cyclohexanecarboxamide | 611.3 | 1.04 | 502 |
| 69 | 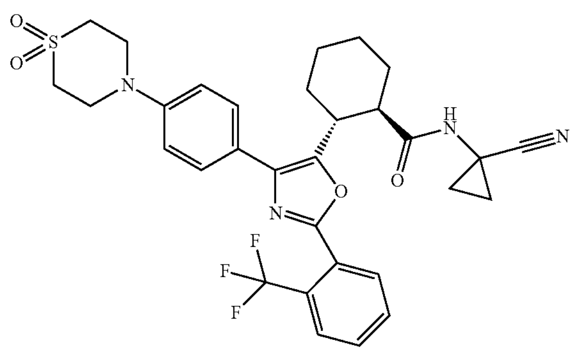 | (1R,2R)-N-(1-cyanocyclopropyl)-2-(4-(4-(1,1-dioxidothiomorpholino)phenyl)-2-(2-(trifluoromethyl)phenyl)oxazol-5-yl)cyclohexanecarboxamide | 613.4 | 2.94 | 827 |
| 70 | 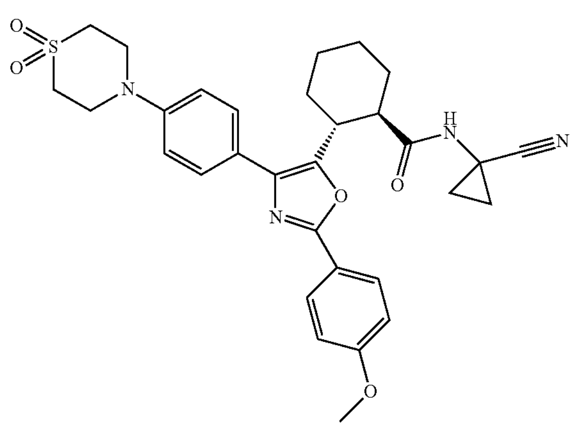 [SMILES: COc1ccc(-c2nc(-c3ccc(N4CCS(=O)(=O)CC4)cc3)c([C@@H]3CCCC[C@H]3C(=O)NC3(C#N)CC3)o2)cc1] | (1R,2R)-N-(1-cyanocyclopropyl)-2-(4-(4-dioxidothiomorpholino)phenyl)-2-(4-methoxyphenyl)oxazol-5-yl)cyclohexanecarboxamide | 575.5 | 1.84 | 734 |

| | Structure | Name | LC-MS m/z (M + H) | hrbC at K IP (nM) | hCat F IP (nM) |
|---|---|---|---|---|---|
| 71 | 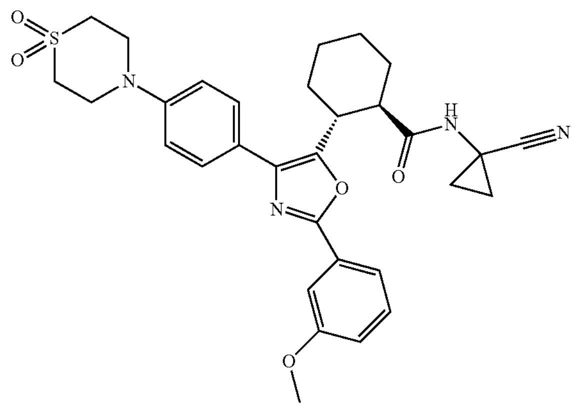 [SMILES: COc1cccc(-c2nc(-c3ccc(N4CCS(=O)(=O)CC4)cc3)c([C@@H]3CCCC[C@H]3C(=O)NC3(C#N)CC3)o2)c1] | (1R,2R)-N-(1-cyanocyclopropyl)-2-(4-(4-(1,1-dioxidothiomorpholino)phenyl)-2-(3-methoxyphenyl)oxazol-5-yl)cyclohexanecarboxamide | 575.0 | 1.59 | 511 |
| 72 | 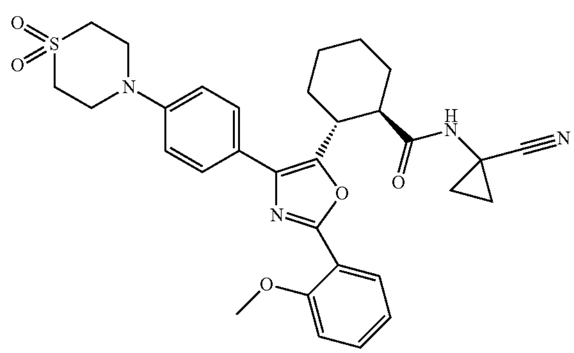 [SMILES: COc1ccccc1-c1nc(-c2ccc(N3CCS(=O)(=O)CC3)cc2)c([C@@H]2CCCC[C@H]2C(=O)NC2(C#N)CC2)o1] | (1R,2R)-N-(1-cyanocyclopropyl)-2-(4-(4-(1,1-dioxidothiomorpholino)phenyl)-2-(2-methoxyphenyl)oxazol-5-yl)cyclohexanecarboxamide | 575.3 | 1.49 | 750 |
| 73 | 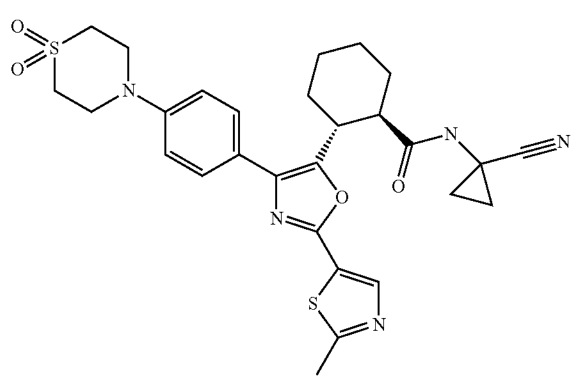 [SMILES: Cc1ncc(-c2nc(-c3ccc(N4CCS(=O)(=O)CC4)cc3)c([C@@H]3CCCC[C@H]3C(=O)NC3(C#N)CC3)o2)s1] | (1R,2R)-N-(1-cyanocyclopropyl)-2-(4-(4-(1,1-dioxidothiomorpholino)phenyl)-2-(2-methylthiazol-5-yl)oxazol-5-yl)cyclohexanecarboxamide | 566.0 | 1.42 | 1,494 |

| | Structure | Name | LC-MS m/z (M + H) | hrbC at K IP (nM) | hCat F IP (nM) |
|---|---|---|---|---|---|
| 74 | 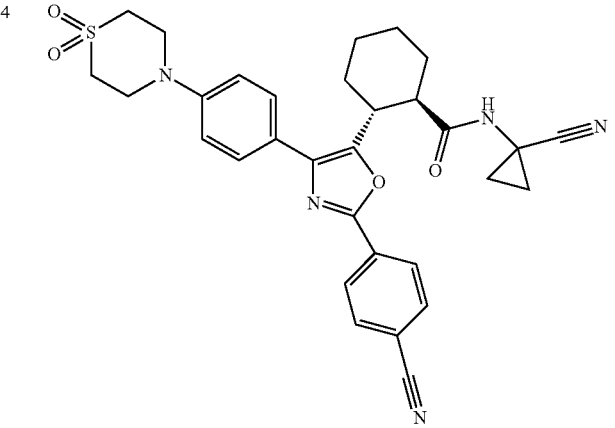 | (1R,2R)-N-(1-cyanocyclopropyl)-2-(2-(4-cyanophenyl)-4-(4-(1,1-dioxidothiomorpholino)phenyl)oxazol-5-yl)cyclohexanecarboxamide | 570.2 | 1.46 | 645 |
| 75 | 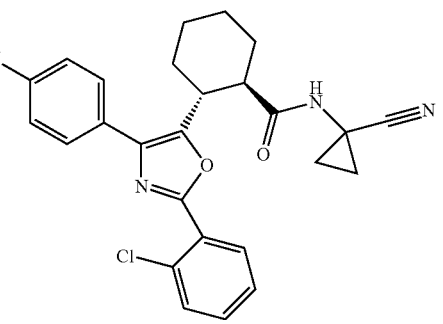 | (1R,2R)-2-(2-(2-chlorophenyl)-4-(4-(1,1-dioxidothiomorpholino)phenyl)oxazol-5-yl)-N-(1-cyanocyclopropyl)cyclohexanecarboxamide | 581.0 | 2.06 | 865 |
| 76 | 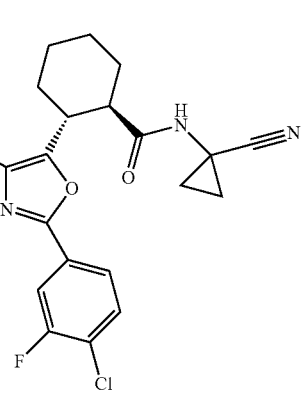 | (1R,2R)-2-(2-(4-chloro-3-fluorophenyl)-4-(4-(1,1-dioxidothiomorpholino)phenyl)oxazol-5-yl)-N-(1-cyanocyclopropyl)cyclohexanecarboxamide | 597.3 | 1.10 | 499 |

-continued

| | Structure | Name | LC-MS m/z (M + H) | hrbC at K IP (nM) | hCat F IP (nM) |
|---|---|---|---|---|---|
| 77 | 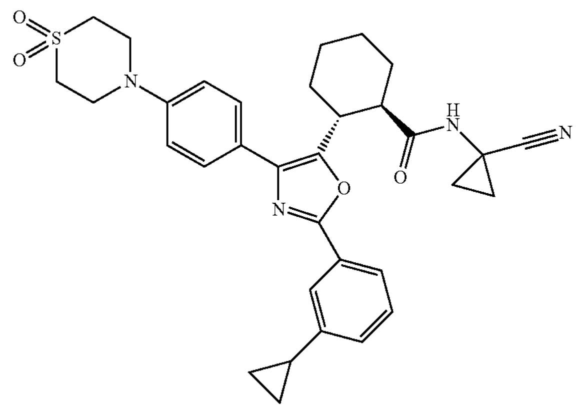 [SMILES: N#CC1(NC(=O)[C@@H]2CCCC[C@H]2c2oc(-c3cccc(C4CC4)c3)nc2-c2ccc(N3CCS(=O)(=O)CC3)cc2)CC1] | (1R,2R)-N-(1-cyanocyclopropyl)-2-(2-(3-cyclopropylphenyl)-4-(4-(1,1-dioxidothiomorpholino)phenyl)oxazol-5-yl)cyclohexanecarboxamide | 585.3 | 0.65 | 533 |
| 78 | 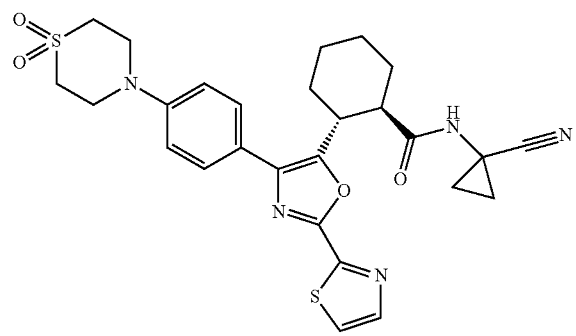 [SMILES: N#CC1(NC(=O)[C@@H]2CCCC[C@H]2c2oc(-c3nccs3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(thiazol-2-yl)oxazol-5-yl)cyclohexanecarboxamide | 552.1 | 2.49 | 2,654 |
| 79 | 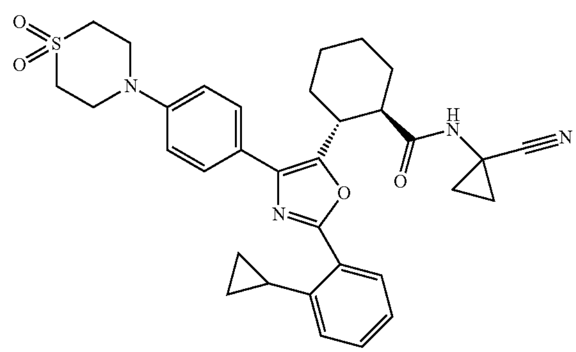 [SMILES: N#CC1(NC(=O)[C@@H]2CCCC[C@H]2c2oc(-c3ccccc3C3CC3)nc2-c2ccc(N3CCS(=O)(=O)CC3)cc2)CC1] | (1R,2R)-N-(1-cyanocyclopropyl)-2-(2-(2-cyclopropylphenyl)-4-(4-(1,1-dioxidothiomorpholino)phenyl)oxazol-5-yl)cyclohexanecarboxamide | 585.0 | 0.51 | 124 |
| 80 | 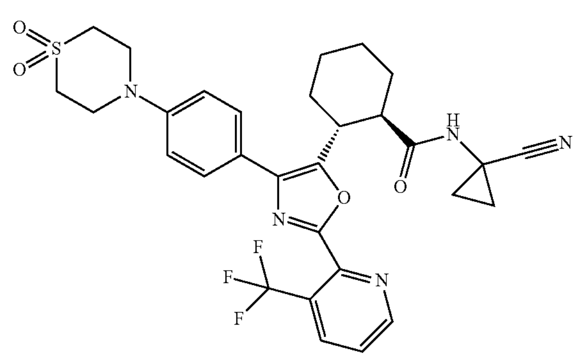 [SMILES: N#CC1(NC(=O)[C@@H]2CCCC[C@H]2c2oc(-c3ncccc3C(F)(F)F)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(3-(trifluoromethyl)pyridin-2-yl)oxazol-5-yl)cyclohexanecarboxamide | 614.2 | 2.43 | 1,492 |

-continued

| | Structure | Name | LC-MS m/z (M + H) | hrbC at K IP (nM) | hCat F IP (nM) |
|---|---|---|---|---|---|
| 81 | 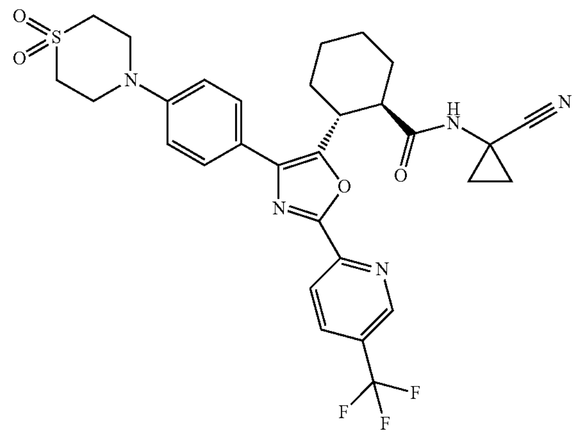 [SMILES: N#CC1(NC(=O)[C@@H]2CCCC[C@H]2c2oc(-c3ccc(C(F)(F)F)cn3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(5-(trifluoromethyl)pyridin-2-yl)oxazol-5-yl)cyclohexanecarboxamide | 614.2 | 2.99 | 3,062 |
| 82 | 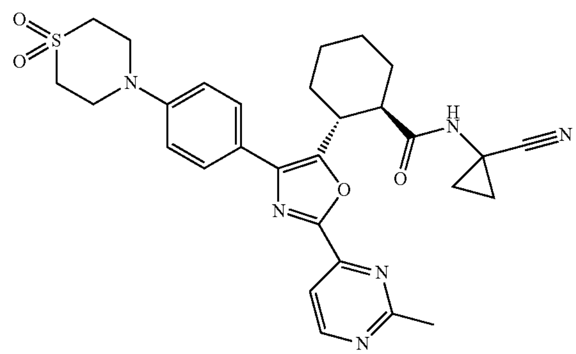 [SMILES: Cc1nccc(-c2nc(-c3ccc(N4CCS(=O)(=O)CC4)cc3)c([C@@H]3CCCC[C@H]3C(=O)NC3(C#N)CC3)o2)n1] | (1R,2R)-N-(1-cyanocyclopropyl)-2-(4-(4-(1,1-dioxidothiomorpholino)phenyl)-2-(2-methylpyrimidin-4-yl)oxazol-5-yl)cyclohexanecarboxamide | 561.2 | 2.66 | 5,137 |
| 83 | 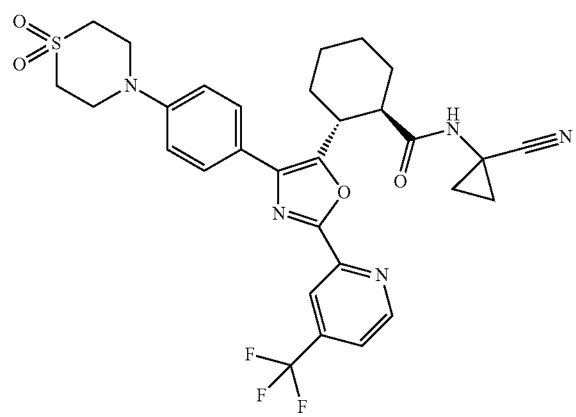 [SMILES: N#CC1(NC(=O)[C@@H]2CCCC[C@H]2c2oc(-c3cc(C(F)(F)F)ccn3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(4-(trifluoromethyl)pyridin-2-yl)oxazol-5-yl)cyclohexanecarboxamide | 614.2 | 1.30 | 4,150 |
| 84 | 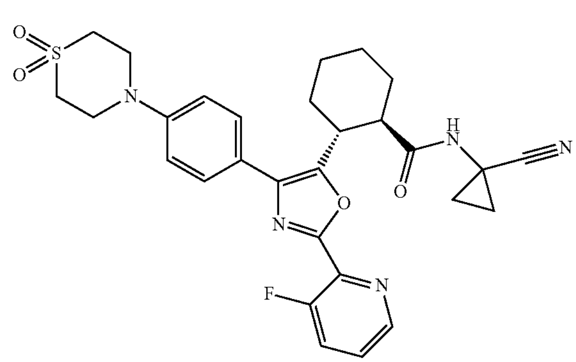 | (1R,2R)-N-(1-cyanocyclopropyl)-2-(4-(4-(1,1-dioxidothiomorpholino)phenyl)-2-(3-fluoropyridin-2-yl)oxazol-5-yl)cyclohexanecarboxamide | 564.3 | 2.92 | 4,230 |

| | Structure | Name | LC-MS m/z (M + H) | hrbC at K IP (nM) | hCat F IP (nM) |
|---|---|---|---|---|---|
| 85 | 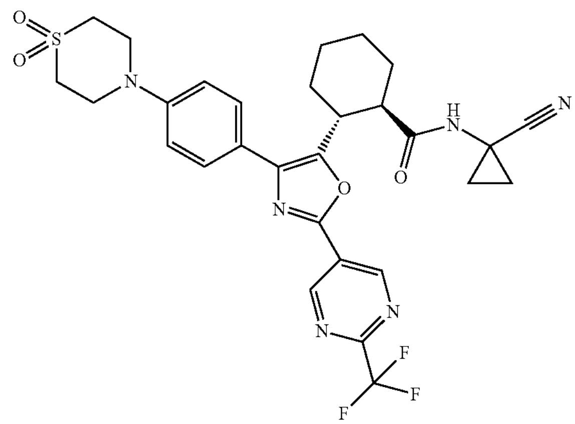 [SMILES: N#CC1(NC(=O)[C@@H]2CCCC[C@H]2c2oc(-c3cnc(C(F)(F)F)nc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(2-(trifluoromethyl)pyrimidin-5-yl)oxazol-5-yl)cyclohexanecarboxamide | 615.2 | 1.57 | 2,523 |
| 86 | 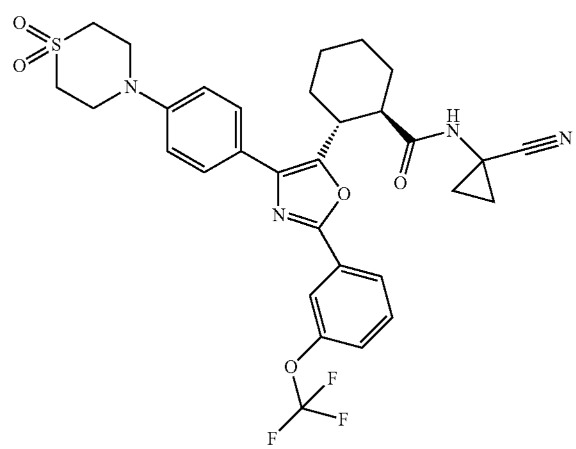 [SMILES: N#CC1(NC(=O)[C@@H]2CCCC[C@H]2c2oc(-c3cccc(OC(F)(F)F)c3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(3-(trifluoromethoxy)phenyl)oxazol-5-yl)cyclohexanecarboxamide | 629.2 | 2.62 | 1,829 |
| 87 | S,S and R,R | (1R,2R)-N-(1-cyanocyclopropyl)-2-(4-(4-((1R,4R and 1S,4S)-2,2-dioxido-2-thia-5-azabicyclo[2.2.1]heptan-5-yl)phenyl)-2-(4-fluorophenyl)oxazol-5-yl)cyclohexanecarboxamide | 575.2 | 4.09 | 1,221 |

-continued

| | Structure | Name | LC-MS m/z (M + H) | hrbC at K IP (nM) | hCat F IP (nM) |
|---|---|---|---|---|---|
| 88 | 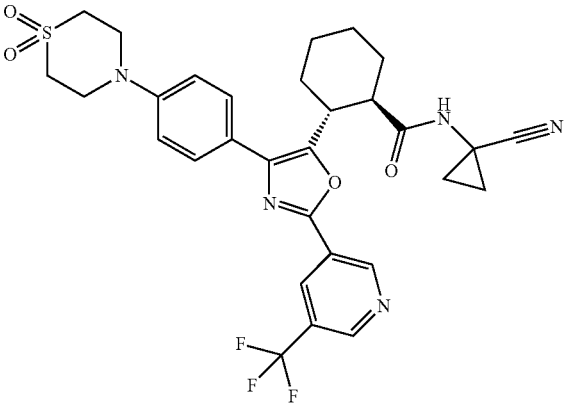 [SMILES: N#CC1(NC(=O)[C@@H]2CCCC[C@H]2c2oc(-c3cncc(C(F)(F)F)c3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(5-(trifluoromethyl)pyridin-3-yl)oxazol-5-yl)cyclohexanecarboxamide | 614.1 | 2.21 | 2,380 |
| 89 | 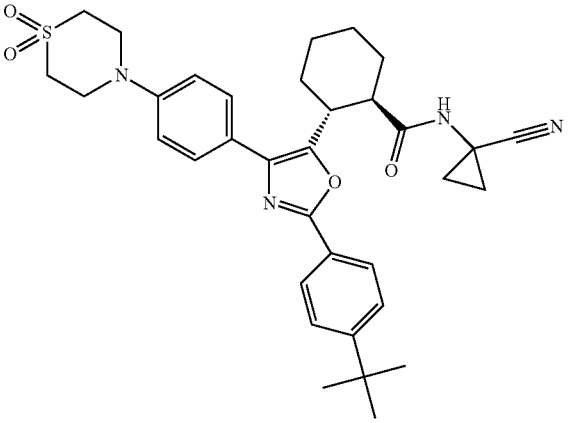 [SMILES: CC(C)(C)c1ccc(-c2nc(-c3ccc(N4CCS(=O)(=O)CC4)cc3)c([C@@H]3CCCC[C@H]3C(=O)NC3(C#N)CC3)o2)cc1] | (1R,2R)-2-(2-(4-(tert-butyl)phenyl)-4-(1,1-dioxidothiomorpholino)phenyl)oxazol-5-yl)-N-(1-cyanocyclopropyl)cyclohexanecarboxamide | 601.3 | 1.35 | 819 |
| 90 | 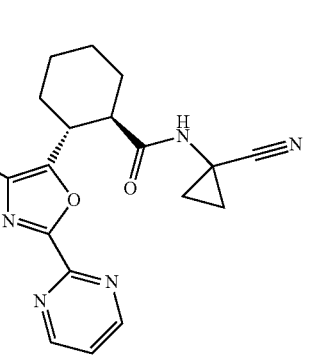 | (1R,2R)-N-(1-cyanocyclopropyl)-2-(4-(4-(1,1-dioxidothiomorpholino)phenyl)-2-(pyrimidin-2-yl)oxazol-5-yl)cyclohexanecarboxamide | 547.3 | 7.28 | 10,000 |

-continued

| | Structure | Name | LC-MS m/z (M + H) | hrbC at K IP (nM) | hCat F IP (nM) |
|---|---|---|---|---|---|
| 91 | 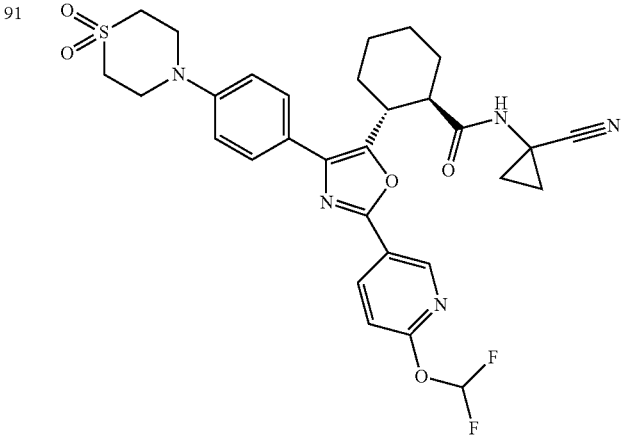 | (1R,2R)-N-(1-cyanocyclopropyl)-2-(2-(6-(difluoromethoxy)pyridin-3-yl)-4-(4-(1,1-dioxidothiomorpholino)phenyl)oxazol-5-yl)cyclohexanecarboxamide | 612.1 | 1.30 | 1,668 |
| 92 | 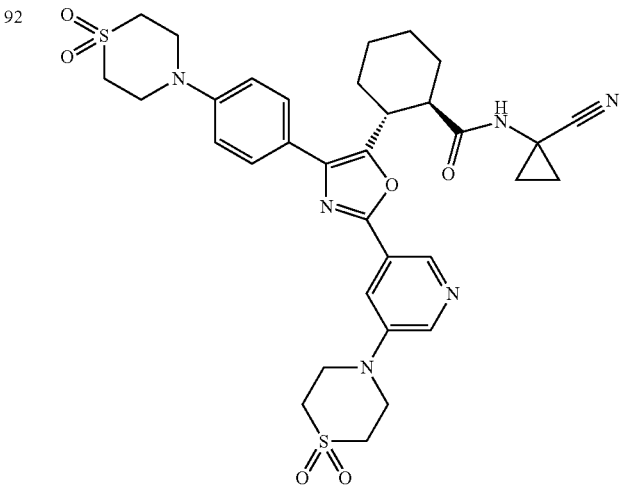 | (1R,2R)-N-(1-cyanocyclopropyl)-2-(4-(4-(1,1-dioxidothiomorpholino)phenyl)-2-(5-(1,1-dioxidothiomorpholino)pyridin-3-yl)oxazol-5-yl)cyclohexanecarboxamide | 679.0 | 0.92 | 803 |
| 93 | 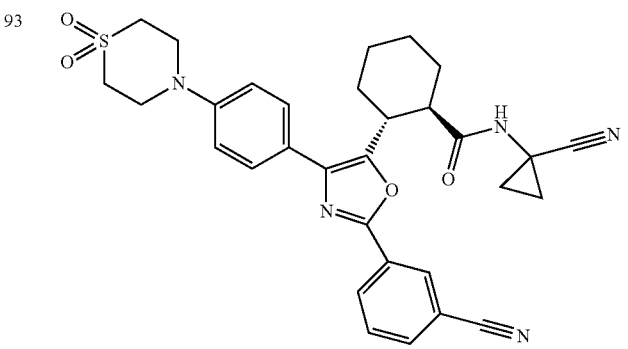 | (1R,2R)-N-(1-cyanocyclopropyl)-2-(2-(3-cyanophenyl)-4-(4-(1,1-dioxidothiomorpholino)phenyl)oxazol-5-yl)cyclohexanecarboxamide | 570.3 | 1.89 | 1,098 |

-continued

| | Structure | Name | LC-MS m/z (M + H) | hrbC at K IP (nM) | hCat F IP (nM) |
|---|---|---|---|---|---|
| 94 | 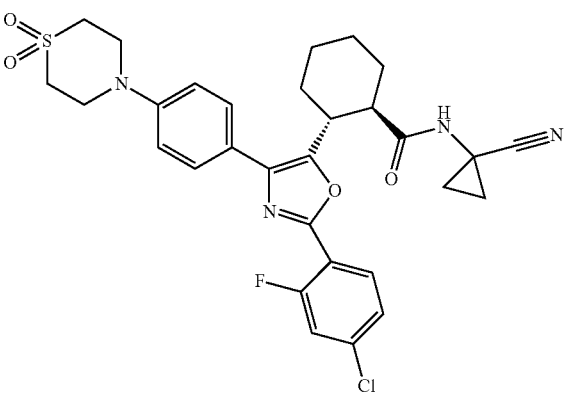 [SMILES: N#CC1(NC(=O)[C@@H]2CCCC[C@H]2c2oc(-c3ccc(Cl)cc3F)nc2-c2ccc(N3CCS(=O)(=O)CC3)cc2)CC1] | (1R,2R)-2-(2-(4-chloro-2-fluorophenyl)-4-(4-(1,1-dioxidothiomorpholino)phenyl)oxazol-5-yl)-N-(1-cyanocyclopropyl)cyclohexanecarboxamide | 597.0 | 1.20 | 380 |
| 95 | 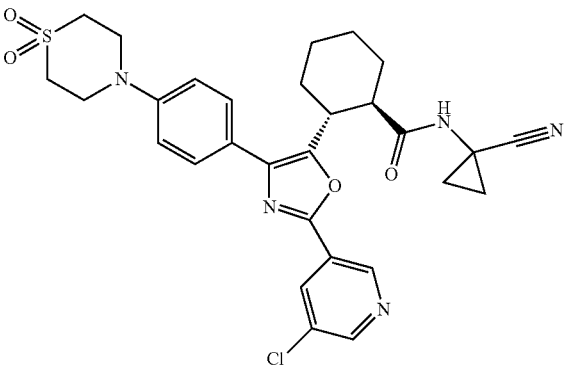 | (1R,2R)-2-(2-(5-chloropyridin-3-yl)-4-(4-(1,1-dioxidothiomorpholino)phenyl)oxazol-5-yl)-N-(1-cyanocyclopropyl)cyclohexanecarboxamide | 580.0 | 1.17 | 775 |
| 96 | 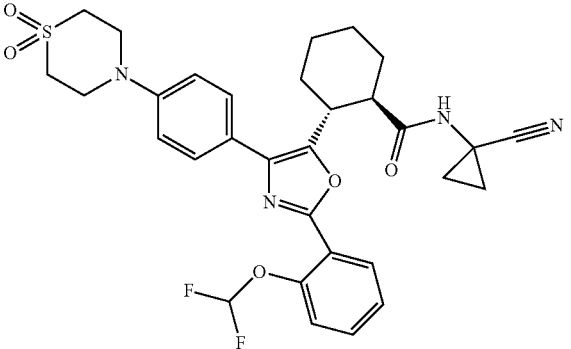 [SMILES: N#CC1(NC(=O)[C@@H]2CCCC[C@H]2c2oc(-c3ccccc3OC(F)F)nc2-c2ccc(N3CCS(=O)(=O)CC3)cc2)CC1] | (1R,2R)-N-(1-cyanocyclopropyl)-2-(2-(2-(difluoromethoxy)phenyl)-4-(4-(1,1-dioxidothiomorpholino)phenyl)oxazol-5-yl)cyclohexanecarboxamide | 611.2 | 0.87 | 363 |
| 97 | 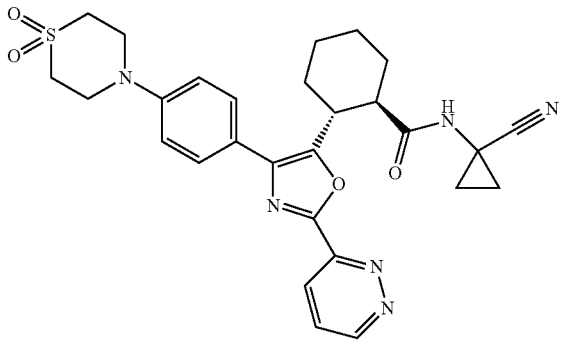 [SMILES: N#CC1(NC(=O)[C@@H]2CCCC[C@H]2c2oc(-c3cccnn3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(pyridazin-3-yl)oxazol-5-yl)cyclohexanecarboxamide | 547.0 | 2.83 | 2,553 |

-continued

| | Structure | Name | LC-MS m/z (M + H) | hrbC at K IP (nM) | hCat F IP (nM) |
|---|---|---|---|---|---|
| 98 | 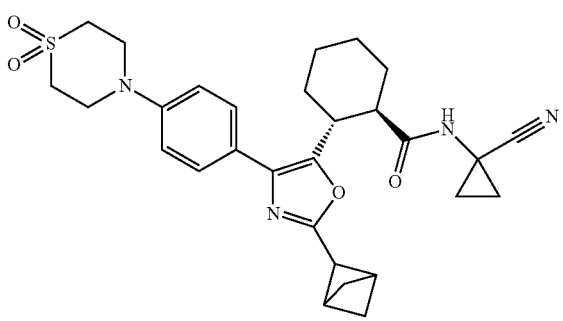 [SMILES: N#CC1(NC(=O)[C@@H]2CCCC[C@H]2c2oc(C3C4CC3C4)nc2-c2ccc(N3CCS(=O)(=O)CC3)cc2)CC1] | (1R,2R)-2-(2-(bicyclo[1.1.1]pentan-2-yl)-4-(4-(1,1-dioxidothiomorpholino)phenyl)oxazol-5-yl)-N-(1-cyanocyclopropyl)cyclohexanecarboxamide | 535.3 | 1.43 | 2,305 |
| 99 | 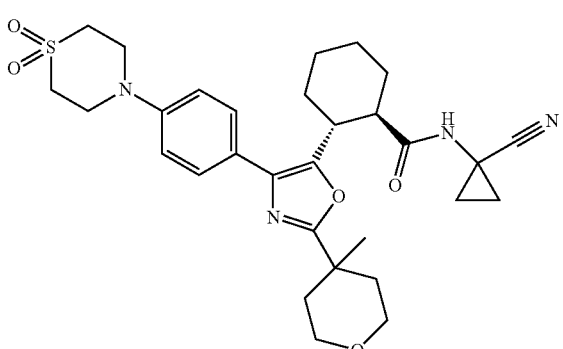 | (1R,2R)-N-(1-cyanocyclopropyl)-2-(4-(4-(1,1-dioxidothiomorpholino)phenyl)-2-(4-methyltetrahydro-2H-pyran-4-yl)oxazol-5-yl)cyclohexanecarboxamide | 567.4 | 1.89 | 2,230 |
| 100 | 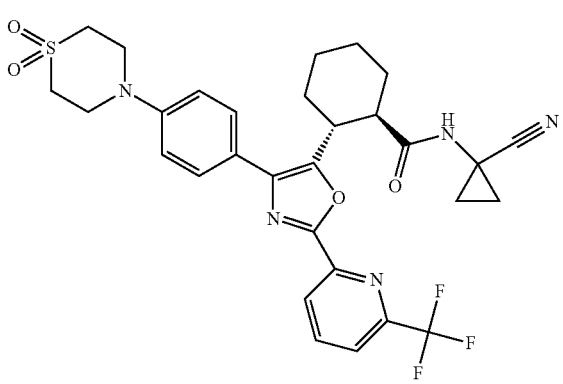 [SMILES: N#CC1(NC(=O)[C@@H]2CCCC[C@H]2c2oc(-c3cccc(C(F)(F)F)n3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(6-(trifluoromethyl)pyridin-2-yl)oxazol-5-yl)cyclohexanecarboxamide | 614.3 | 4.11 | 2,857 |
| 101 | 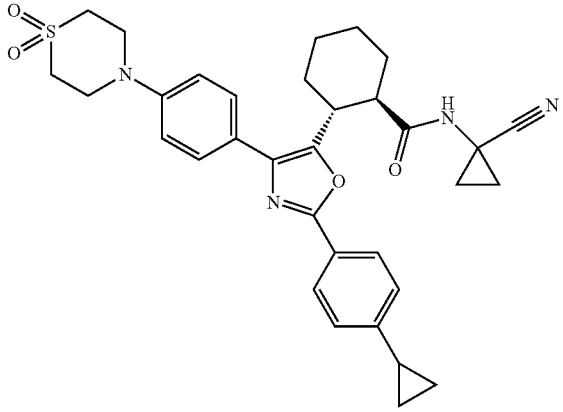 [SMILES: N#CC1(NC(=O)[C@@H]2CCCC[C@H]2c2oc(-c3ccc(C4CC4)cc3)nc2-c2ccc(N3CCS(=O)(=O)CC3)cc2)CC1] | (1R,2R)-N-(1-cyanocyclopropyl)-2-(2-(4-cyclopropylphenyl)-4-(4-(1,1-dioxidothiomorpholino)phenyl)oxazol-5-yl)cyclohexanecarboxamide | 585.3 | 0.88 | 377 |

-continued

| | Structure | Name | LC-MS m/z (M + H) | hrbC at K IP (nM) | hCat F IP (nM) |
|---|---|---|---|---|---|
| 102 | 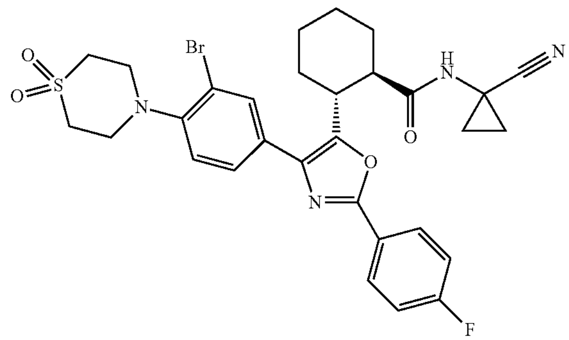 [SMILES: N#CC1(NC(=O)[C@@H]2CCCC[C@H]2c2oc(-c3ccc(F)cc3)nc2-c2ccc(N3CCS(=O)(=O)CC3)c(Br)c2)CC1] | (1R,2R)-2-(4-(3-bromo-4-(1,1-dioxidothiomorpholino)phenyl)-2-(4-fluorophenyl)oxazol-5-yl)-N-(1-cyanocyclopropyl)cyclohexanecarboxamide | 641.2 643.2 | 54.48 | 416 |
| 103 | 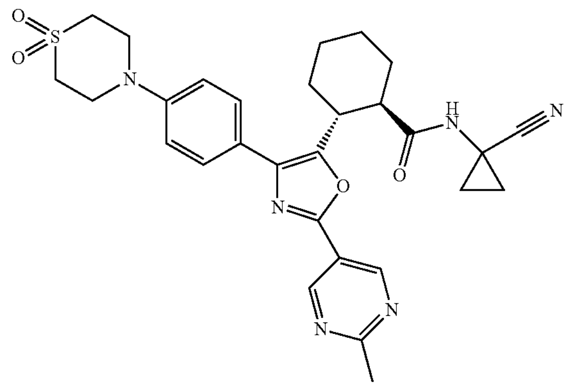 [SMILES: Cc1ncc(-c2nc(-c3ccc(N4CCS(=O)(=O)CC4)cc3)c([C@@H]3CCCC[C@H]3C(=O)NC3(C#N)CC3)o2)cn1] | (1R,2R)-N-(1-cyanocyclopropyl)-2-(4-(4-(1,1-dioxidothiomorpholino)phenyl)-2-(2-methylpyrimidin-5-yl)oxazol-5-yl)cyclohexanecarboxamide | 561.5 | 1.35 | 1,836 |
| 104 | 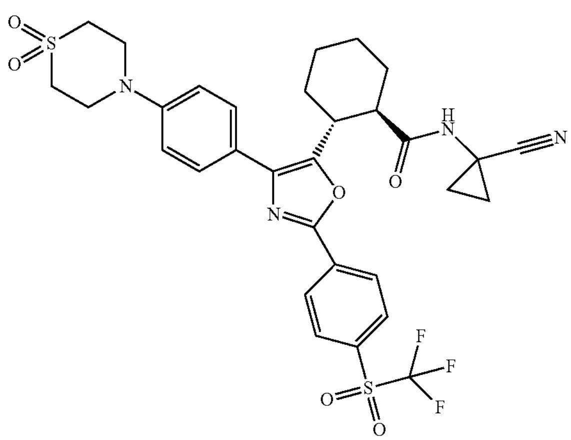 [SMILES: N#CC1(NC(=O)[C@@H]2CCCC[C@H]2c2oc(-c3ccc(S(=O)(=O)C(F)(F)F)cc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(4-((trifluoromethyl)sulfonyl)phenyl)oxazol-5-yl)cyclohexanecarboxamide | 677.6 | 2.40 | 1,000 |
| 105 | 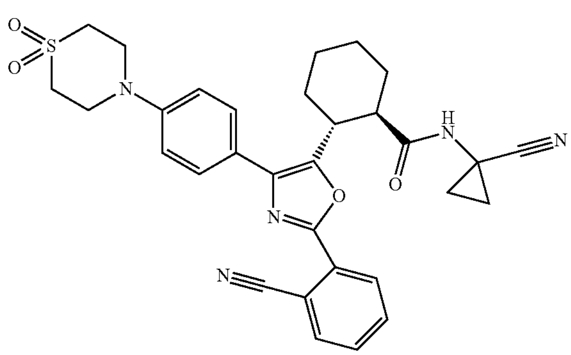 [SMILES: N#Cc1ccccc1-c1nc(-c2ccc(N3CCS(=O)(=O)CC3)cc2)c([C@@H]2CCCC[C@H]2C(=O)NC2(C#N)CC2)o1] | (1R,2R)-N-(1-cyanocyclopropyl)-2-(2-(2-cyanophenyl)-4-(4-(1,1-dioxidothiomorpholino)phenyl)oxazol-5-yl)cyclohexanecarboxamide | 570.2 | 2.40 | 1,925 |

-continued

| | Structure | Name | LC-MS m/z (M + H) | hrbC at K IP (nM) | hCat F IP (nM) |
|---|---|---|---|---|---|
| 106 | 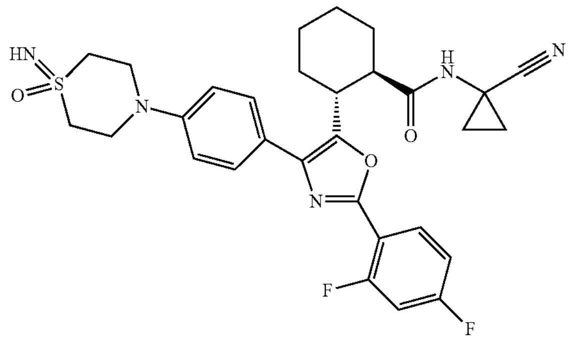 [SMILES: N#CC1(NC(=O)[C@@H]2CCCC[C@H]2c2oc(-c3ccc(F)cc3F)nc2-c2ccc(N3CCS(=N)(=O)CC3)cc2)CC1] | (1R,2R)-N-(1-cyanocyclopropyl)-2-(2-(2,4-difluorophenyl)-4-(4-(1-imino-1-oxidothiomorpholino)phenyl)oxazol-5-yl)cyclohexanecarboxamide | 580.4 | 1.59 | 192 |
| 107 | 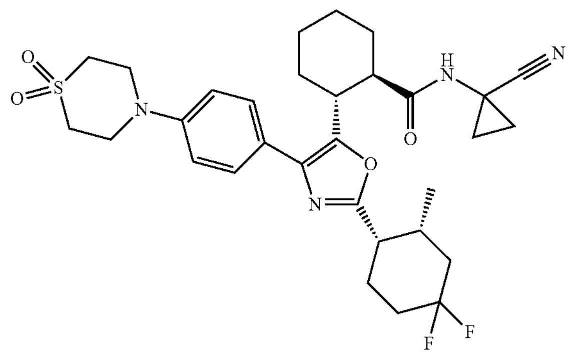 [SMILES: C[C@@H]1CC(F)(F)CC[C@@H]1c1nc(-c2ccc(N3CCS(=O)(=O)CC3)cc2)c([C@@H]2CCCC[C@H]2C(=O)NC2(C#N)CC2)o1] | (1R,2R)-N-(1-cyanocyclopropyl)-2-(2-((1S,2R)-4,4-difluoro-2-methylcyclohexyl)-4-(4-(1,1-dioxidothiomorpholino)phenyl)oxazol-5-yl)cyclohexanecarboxamide | 601.3 | 2.31 | 1,294 |
| 108 | 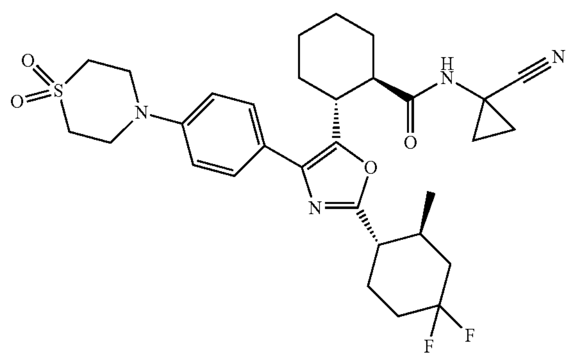 [SMILES: C[C@H]1CC(F)(F)CC[C@@H]1c1nc(-c2ccc(N3CCS(=O)(=O)CC3)cc2)c([C@@H]2CCCC[C@H]2C(=O)NC2(C#N)CC2)o1] | (1R,2R)-N-(1-cyanocyclopropyl)-2-(2-((1S,2S)-4,4-difluoro-2-methylcyclohexyl)-4-(4-(1,1-dioxidothiomorpholino)phenyl)oxazol-5-yl)cyclohexanecarboxamide | 601.3 | 2.08 | 1,387 |
| 109 | 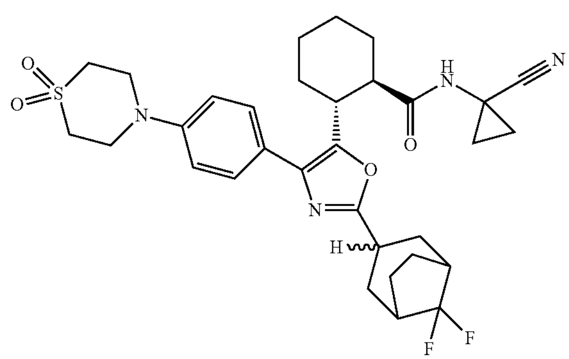 [SMILES: N#CC1(NC(=O)[C@@H]2CCCC[C@H]2c2oc(C3CC4CCC(C3)C4(F)F)nc2-c2ccc(N3CCS(=O)(=O)CC3)cc2)CC1] | (1R,2R)-N-(1-cyanocyclopropyl)-2-(2-((1R,3R,5S and 1R,3S,5S)-8,8-difluorobicyclo[3.2.1]octan-3-yl)-4-(4-(1,1-dioxidothiomorpholino)phenyl)oxazol-5-yl)cyclohexanecarboxamide | 613.3 | 1.70 | 1,501 |

| | Structure | Name | LC-MS m/z (M + H) | hrbC at K IP (nM) | hCat F IP (nM) |
|---|---|---|---|---|---|
| 110 | 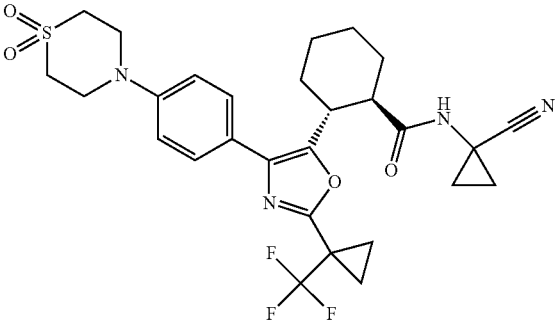 [SMILES: N#CC1(NC(=O)[C@@H]2CCCC[C@H]2c2oc(C3(C(F)(F)F)CC3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(1-(trifluoromethyl)cyclopropyl)oxazol-5-yl)cyclohexanecarboxamide | 577.0 | 1.10 | 931 |
| 111 | 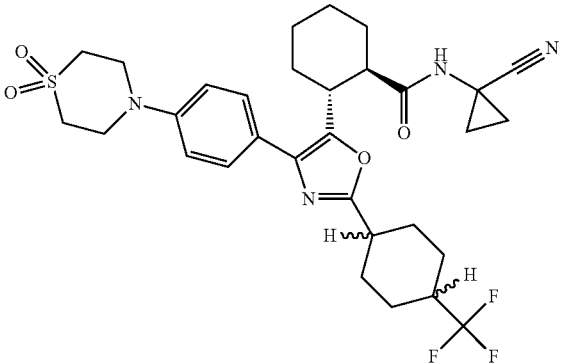 [SMILES: N#CC1(NC(=O)[C@@H]2CCCC[C@H]2c2oc(C3CCC(C(F)(F)F)CC3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-((1R,4R and 1S,4S)-4-(trifluoromethyl)cyclohexyl)oxazol-5-yl)cyclohexanecarboxamide | 619.0 | 1.83 | 1,065 |
| 112 | 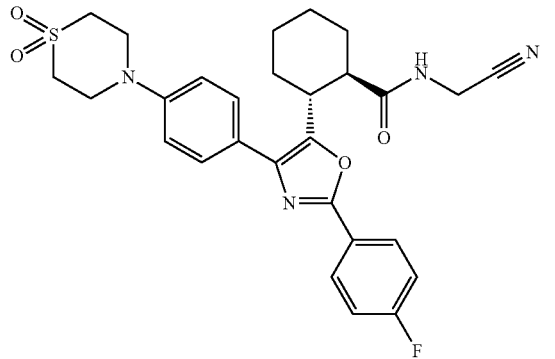 [SMILES: N#CCNC(=O)[C@@H]1CCCC[C@H]1c1oc(-c2ccc(F)cc2)nc1-c1ccc(N2CCS(=O)(=O)CC2)cc1] | (1R,2R)-N-(cyanomethyl)-2-(4-(4-(1,1-dioxidothiomorpholino)phenyl)-2-(4-fluorophenyl)oxazol-5-yl)cyclohexanecarboxamide | 537.2 | 0.73 | 126 |
| 113 | 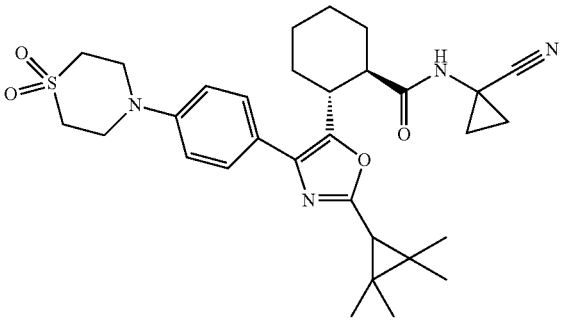 [SMILES: CC1(C)C(c2nc(-c3ccc(N4CCS(=O)(=O)CC4)cc3)c([C@@H]3CCCC[C@H]3C(=O)NC3(C#N)CC3)o2)C1(C)C] | (1R,2R)-N-(1-cyanocyclopropyl)-2-(4-(4-(1,1-dioxidothiomorpholino)phenyl)-2-(2,2,3,3-tetramethylcyclopropyl)oxazol-5-yl)cyclohexanecarboxamide | 565.4 | 4.21 | 2,449 |

-continued

| | Structure | Name | LC-MS m/z (M + H) | hrbC at K IP (nM) | hCat F IP (nM) |
|---|---|---|---|---|---|
| 114 | 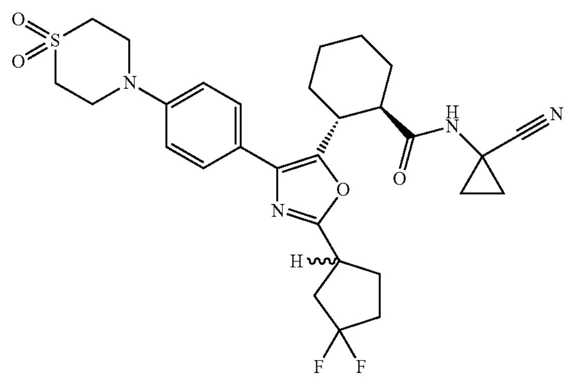 [SMILES: N#CC1(NC(=O)[C@@H]2CCCC[C@H]2c2oc(C3CCC(F)(F)C3)nc2-c2ccc(N3CCS(=O)(=O)CC3)cc2)CC1] | (1R,2R)-N-(1-cyanocyclopropyl)-2-(2-((R and S)-3,3-difluorocyclopentyl)-4-(4-(1,1-dioxidothiomorpholino)phenyl)oxazol-5-yl)cyclohexanecarboxamide | 573.3 | 1.70 | 1,524 |
| 115 | 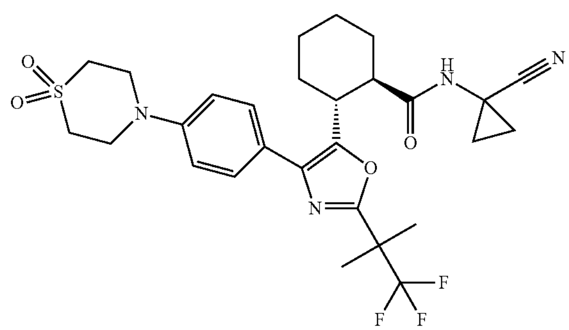 [SMILES: CC(C)(c1nc(-c2ccc(N3CCS(=O)(=O)CC3)cc2)c([C@@H]2CCCC[C@H]2C(=O)NC2(C#N)CC2)o1)C(F)(F)F] | (1R,2R)-N-(1-cyanocyclopropyl)-2-(4-(4-(1,1-dioxidothiomorpholino)phenyl)-2-(1,1,1-trifluoro-2-methylpropan-2-yl)oxazol-5-yl)cyclohexanecarboxamide | 579.2 | 1.34 | 1,765 |
| 116 | 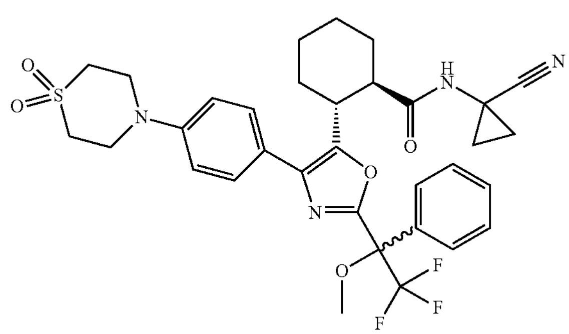 [SMILES: COC(c1ccccc1)(c1nc(-c2ccc(N3CCS(=O)(=O)CC3)cc2)c([C@@H]2CCCC[C@H]2C(=O)NC2(C#N)CC2)o1)C(F)(F)F] | (1R,2R)-N-(1-cyanocyclopropyl)-2-(4-(4-(1,1-dioxidothiomorpholino)phenyl)-2-((R and S)-2,2,2-trifluoro-1-methoxy-1-phenylethyl)oxazol-5-yl)cyclohexanecarboxamide | 657.2 | 1.38 | 1,212 |
| 117 | 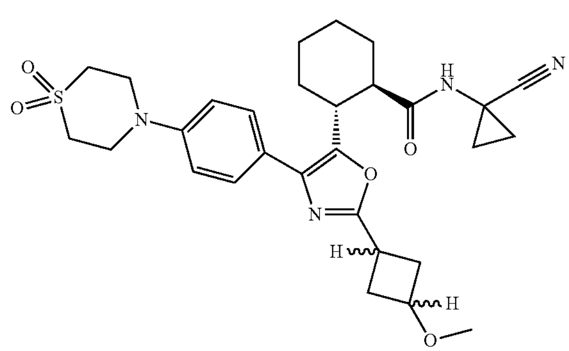 [SMILES: COC1CC(c2nc(-c3ccc(N4CCS(=O)(=O)CC4)cc3)c([C@@H]3CCCC[C@H]3C(=O)NC3(C#N)CC3)o2)C1] | (1R,2R)-N-(1-cyanocyclopropyl)-2-(4-(4-(1,1-dioxidothiomorpholino)phenyl)-2-((1R,3R and 1S,3S)-3-methoxycyclobutyl)oxazol-5-yl)cyclohexanecarboxamide | 553.3 | 1.46 | 2,243 |

-continued

| | Structure | Name | LC-MS m/z (M + H) | hrbC at K IP (nM) | hCat F IP (nM) |
|---|---|---|---|---|---|
| 118 | 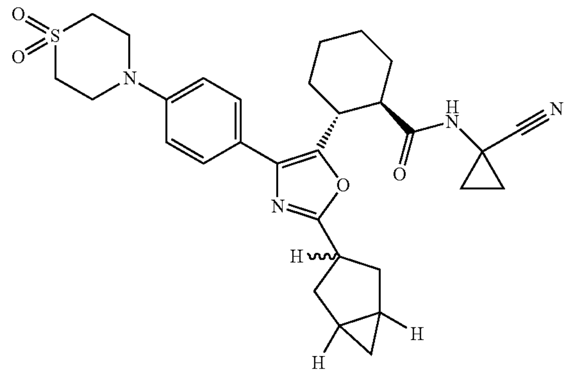 [SMILES: N#CC1(NC(=O)[C@@H]2CCCC[C@H]2c2oc(C3CC4CC4C3)nc2-c2ccc(N3CCS(=O)(=O)CC3)cc2)CC1] | (1R,2R)-2-(2-((1R,3R,5S and 1R,3S,5S)-bicyclo[3.1.0]hexan-3-yl)-4-(4-(1,1-dioxidothiomorpholino)phenyl)oxazol-5-yl)-N-(1-cyanocyclopropyl)cyclohexanecarboxamide | 549.3 | 0.85 | 767 |
| 119 | 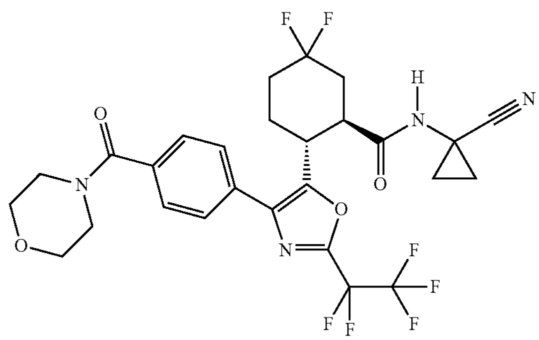 [SMILES: N#CC1(NC(=O)[C@@H]2CC(F)(F)CC[C@H]2c2oc(C(F)(F)C(F)(F)F)nc2-c2ccc(C(=O)N3CCOCC3)cc2)CC1] | (1R,2R)-N-(1-cyanocyclopropyl)-5,5-difluoro-2-(4-(4-(morpholine-4-carbonyl)phenyl)-2-(perfluoroethyl)oxazol-5-yl)cyclohexanecarboxamide | 603.0 | 1.04 | 306 |
| 120 | 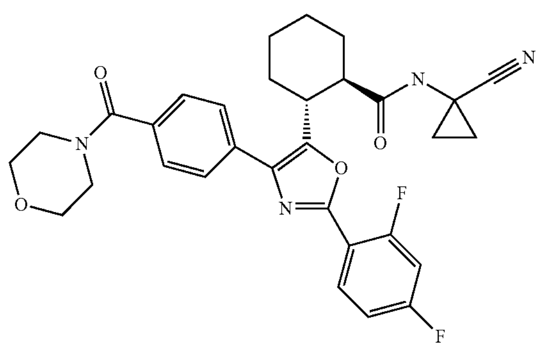 [SMILES: N#CC1(NC(=O)[C@@H]2CCCC[C@H]2c2oc(-c3ccc(F)cc3F)nc2-c2ccc(C(=O)N3CCOCC3)cc2)CC1] | (1R,2R)-N-(1-cyanocyclopropyl)-2-(2-(2,4-difluorophenyl)-4-(4-(morpholine-4-carbonyl)phenyl)oxazol-5-yl)cyclohexanecarboxamide | 561.3 | 14.54 | 1,000 |
| 121 | 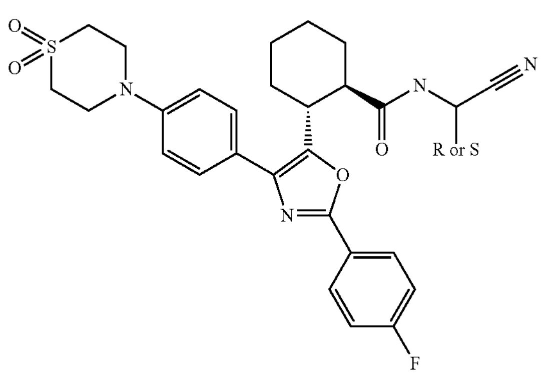 | (1R,2R)-N-((R or S)-1-cyanoethyl)-2-(4-(4-(1,1-dioxidothiomorpholino)phenyl)-2-(4-fluorophenyl)oxazol-5-yl)cyclohexanecarboxamide | 551.2 | 24.09 | 10,000 |

-continued

| | Structure | Name | LC-MS m/z (M + H) | hrbC at K IP (nM) | hCat F IP (nM) |
|---|---|---|---|---|---|
| 122 | 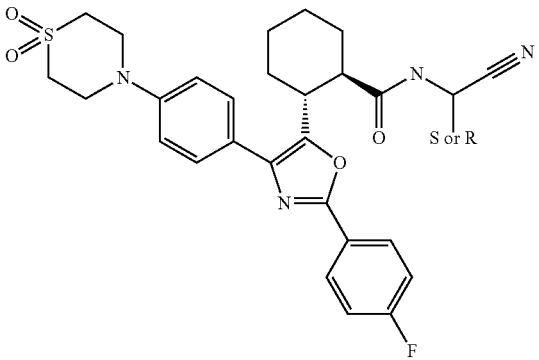 | (1R,2R)-N-((S or R)-1-cyanoethyl)-2-(4-(4-(1,1-dioxidothiomorpholino)phenyl)-2-(4-fluorophenyl)oxazol-5-yl)cyclohexanecarboxamide | 551.4 | 0.80 | 198 |
| 123 | 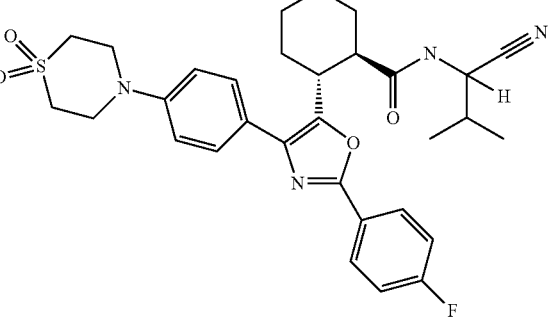 | (1R,2R)-N-((S or R)-1-cyano-2-methylpropyl)-2-(4-(4-(1,1-dioxidothiomorpholino)phenyl)-2-(4-fluorophenyl)oxazol-5-yl)cyclohexanecarboxamide | 579.4 | 2.13 | 472 |
| 124 | 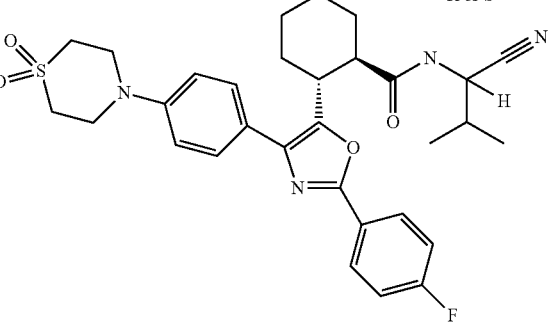 | (1R,2R)-N-((R or S)-1-cyano-2-methylpropyl)-2-(4-(4-(1,1-dioxidothiomorpholino)phenyl)-2-(4-fluorophenyl)oxazol-5-yl)cyclohexanecarboxamide | 579.4 | 1,085.00 | 10,000 |
| 125 | 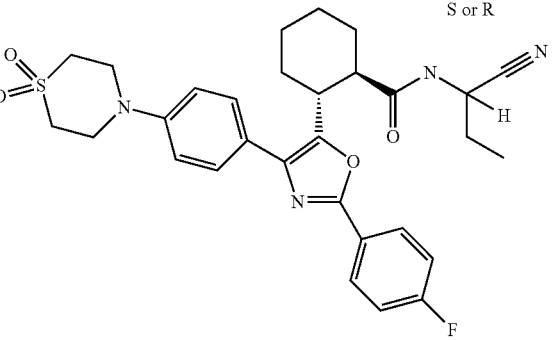 | (1R,2R)-N-((S or R)-1-cyanopropyl)-2-(4-(4-(1,1-dioxidothiomorpholino)phenyl)-2-(4-fluorophenyl)oxazol-5-yl)cyclohexanecarboxamide | 565.4 | 0.69 | 104 |

-continued

| | Structure | Name | LC-MS m/z (M + H) | hrbC at K IP (nM) | hCat F IP (nM) |
|---|---|---|---|---|---|
| 126 | 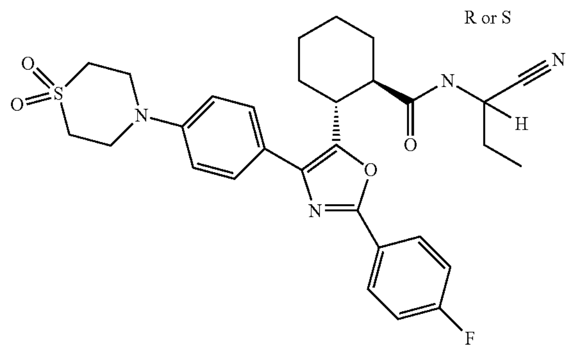 [SMILES: CCC(C#N)NC(=O)[C@@H]1CCCC[C@H]1c1oc(-c2ccc(F)cc2)nc1-c1ccc(N2CCS(=O)(=O)CC2)cc1] | (1R,2R)-N-((R or S)-1-cyanopropyl)-2-(4-(4-(1,1-dioxidothiomorpholino)phenyl)-2-(4-fluorophenyl)oxazol-5-yl)cyclohexanecarboxamide | 565.4 | 14.60 | 9,015 |
| 127 | 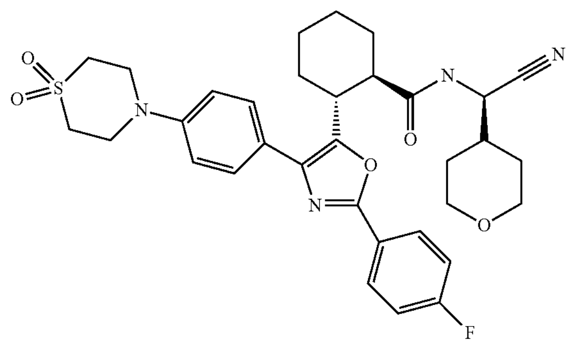 [SMILES: N#C[C@H](NC(=O)[C@@H]1CCCC[C@H]1c1oc(-c2ccc(F)cc2)nc1-c1ccc(N2CCS(=O)(=O)CC2)cc1)C1CCOCC1] | (1R,2R)-N-((R)-cyano(tetrahydro-2H-pyran-4-yl)methyl)-2-(4-(4-(1,1-dioxidothiomorpholino)phenyl)-2-(4-fluorophenyl)oxazol-5-yl)cyclohexanecarboxamide | 621.3 | 48.46 | 10,000 |
| 128 | 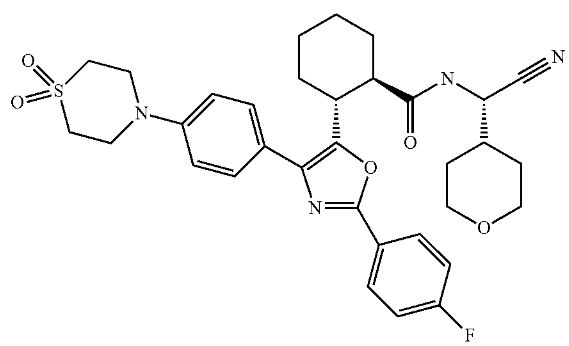 [SMILES: N#C[C@@H](NC(=O)[C@@H]1CCCC[C@H]1c1oc(-c2ccc(F)cc2)nc1-c1ccc(N2CCS(=O)(=O)CC2)cc1)C1CCOCC1] | (1R,2R)-N-((S)-cyano(tetrahydro-2H-pyran-4-yl)methyl)-2-(4-(4-(1,1-dioxidothiomorpholino)phenyl)-2-(4-fluorophenyl)oxazol-5-yl)cyclohexanecarboxamide | 621.3 | 1.94 | 692 |
| 129 | 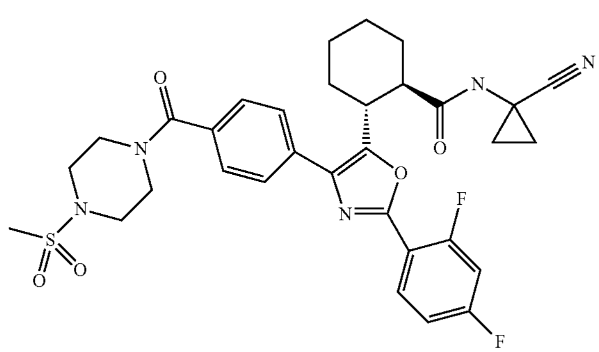 [SMILES: CS(=O)(=O)N1CCN(C(=O)c2ccc(-c3nc(-c4ccc(F)cc4F)oc3[C@@H]3CCCC[C@H]3C(=O)NC3(C#N)CC3)cc2)CC1] | (1R,2R)-N-(1-cyanocyclopropyl)-2-(2-(2,4-difluorophenyl)-4-(4-(4-(methylsulfonyl)piperazine-1-carbonyl)phenyl)oxazol-5-yl)cyclohexanecarboxamide | 638.0 | 9.12 | 3,925 |

| | Structure | Name | LC-MS m/z (M + H) | hrbC at K IP (nM) | hCat F IP (nM) |
|---|---|---|---|---|---|
| 130 | 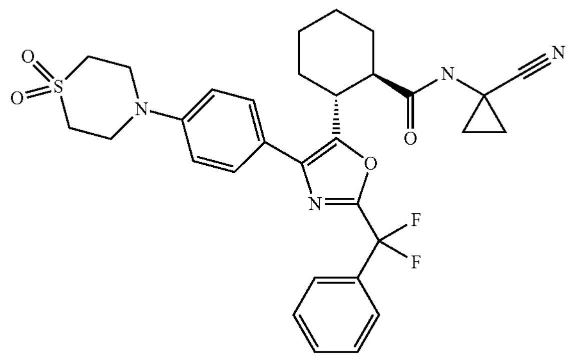 [SMILES: N#CC1(NC(=O)[C@@H]2CCCC[C@H]2c2oc(C(F)(F)c3ccccc3)nc2-c2ccc(N3CCS(=O)(=O)CC3)cc2)CC1] | (1R,2R)-N-(1-cyanocyclopropyl)-2-(2-(difluoro(phenyl)methyl)-4-(4-(1,1-dioxidothiomorpholino)phenyl)oxazol-5-yl)cyclohexanecarboxamide | 595.2 | 1.25 | 70 |
| 131 | 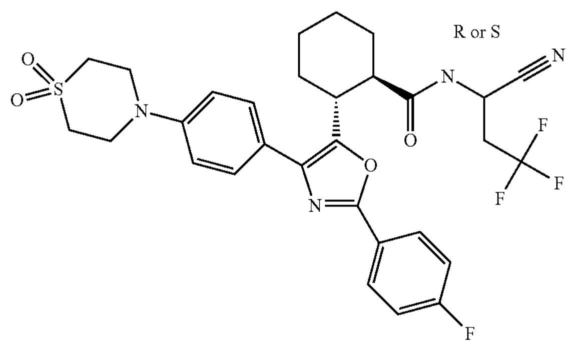 [SMILES: N#CC(CC(F)(F)F)NC(=O)[C@@H]1CCCC[C@H]1c1oc(-c2ccc(F)cc2)nc1-c1ccc(N2CCS(=O)(=O)CC2)cc1] | (1R,2R)-N-((R or S)-1-cyano-3,3,3-trifluoropropyl)-2-(4-(4-(1,1-dioxidothiomorpholino)phenyl)-2-(4-fluorophenyl)oxazol-5-yl)cyclohexanecarboxamide | 619.1 | 0.65 | 14 |
| 132 | 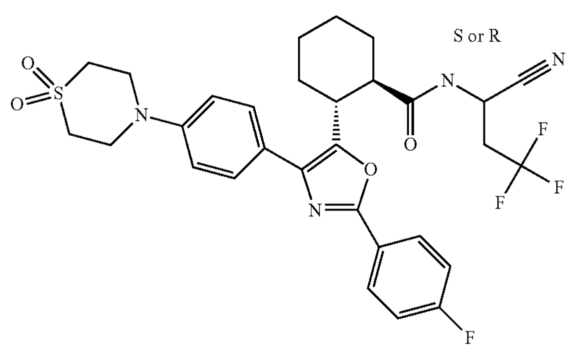 [SMILES: N#CC(CC(F)(F)F)NC(=O)[C@@H]1CCCC[C@H]1c1oc(-c2ccc(F)cc2)nc1-c1ccc(N2CCS(=O)(=O)CC2)cc1] | (1R,2R)-N-((S or R)-1-cyano-3,3,3-trifluoropropyl)-2-(4-(4-(1,1-dioxidothiomorpholino)phenyl)-2-(4-fluorophenyl)oxazol-5-yl)cyclohexanecarboxamide | 619.1 | 1.77 | 670 |
| 133 | 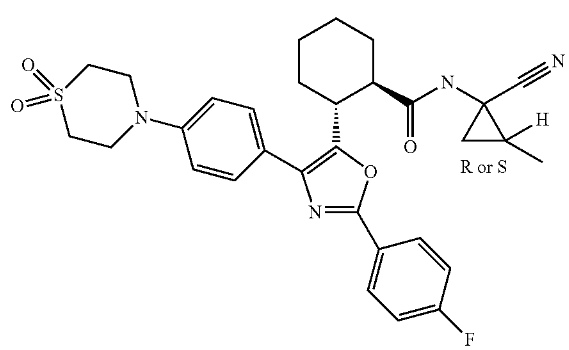 [SMILES: CC1CC1(C#N)NC(=O)[C@@H]1CCCC[C@H]1c1oc(-c2ccc(F)cc2)nc1-c1ccc(N2CCS(=O)(=O)CC2)cc1] | (1R,2R)-N-((2R or 2S)-1-cyano-2-methylcyclopropyl)-2-(4-(4-(1,1-dioxidothiomorpholino)phenyl)-2-(4-fluorophenyl)oxazol-5-yl)cyclohexanecarboxamide | 577.1 | 2.53 | 3,143 |

-continued

| | Structure | Name | LC-MS m/z (M + H) | hrbC at K IP (nM) | hCat F IP (nM) |
|---|---|---|---|---|---|
| 134 | 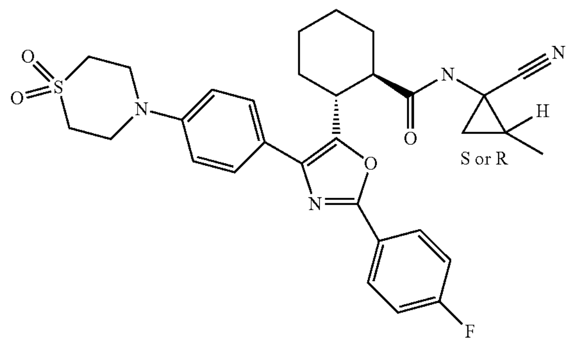 [SMILES: CC1CC1(C#N)NC(=O)[C@@H]1CCCC[C@H]1c1oc(-c2ccc(F)cc2)nc1-c1ccc(N2CCS(=O)(=O)CC2)cc1] | (1R,2R)-N-((2S or 2R)-1-cyano-2-methylcyclopropyl)-2-(4-(4-(1,1-dioxidothiomorpholino)phenyl)-2-(4-fluorophenyl)oxazol-5-yl)cyclohexanecarboxamide | 577.1 | 2,901.0 | 10,000 |
| 135 | 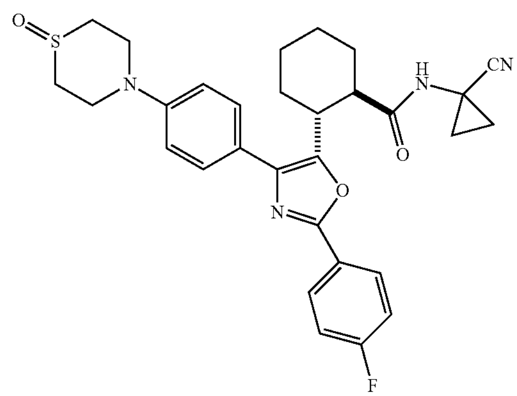 | (1R,2R)-N-(1-cyanocyclopropyl)-2-(2-(4-fluorophenyl)-4-(4-(1-oxidothiomorpholino)phenyl)oxazol-5-yl)cyclohexanecarboxamide | 547.3 | 1.39 | 458 |
| 136 | 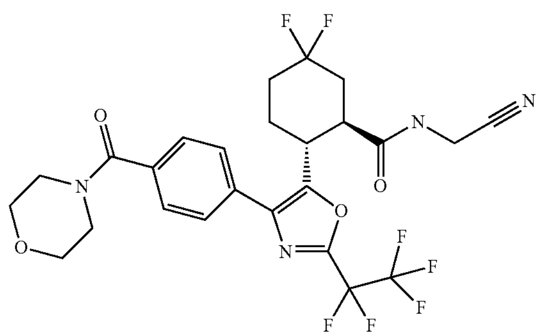 [SMILES: N#CCNC(=O)[C@@H]1CC(F)(F)CC[C@H]1c1oc(C(F)(F)C(F)(F)F)nc1-c1ccc(C(=O)N2CCOCC2)cc1] | (1R,2R)-N-(cyanomethyl)-5,5-difluoro-2-(4-(4-(morpholine-4-carbonyl)phenyl)-2-(perfluoroethyl)oxazol-5-yl)cyclohexanecarboxamide | 577.0 | 0.74 | 319 |
| 137 | 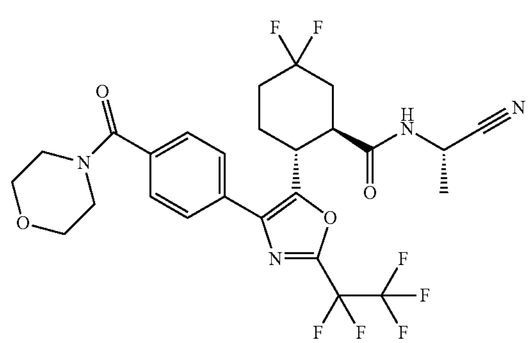 [SMILES: C[C@@H](C#N)NC(=O)[C@@H]1CC(F)(F)CC[C@H]1c1oc(C(F)(F)C(F)(F)F)nc1-c1ccc(C(=O)N2CCOCC2)cc1] | (1R,2R)-N-((S)-1-cyanoethyl)-5,5-difluoro-2-(4-(4-(morpholine-4-carbonyl)phenyl)-2-(perfluoroethyl)oxazol-5-yl)cyclohexanecarboxamide | 591.3 | 0.39 | 295 |

| | Structure | Name | LC-MS m/z (M + H) | hrbC at K IP (nM) | hCat F IP (nM) |
|---|---|---|---|---|---|
| 138 | 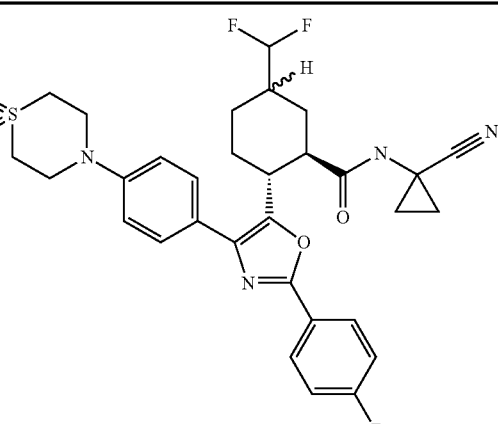 | (1R,2R,5R and 1R,2R,5S)-N-(1-cyanocyclopropyl)-5-(difluoromethyl)-2-(4-(4-(1,1-dioxidothiomorpholino)phenyl)-2-(4-fluorophenyl)oxazol-5-yl)cyclohexanecarboxamide | 613.4 | 12.39 | 151 |
| 139 | 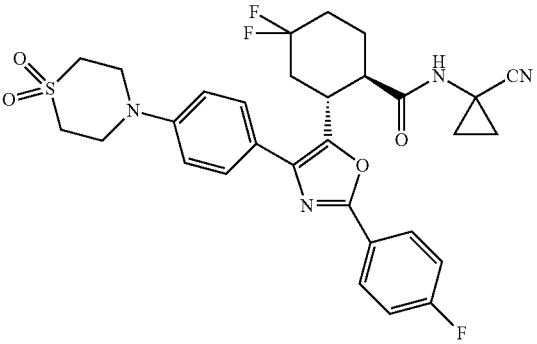 [SMILES: N#CC1(NC(=O)[C@@H]2CCC(F)(F)C[C@H]2c2oc(-c3ccc(F)cc3)nc2-c2ccc(N3CCS(=O)(=O)CC3)cc2)CC1] | (1R,2R)-N-(1-cyanocyclopropyl)-2-(4-(4-(1,1-dioxidothiomorpholino)phenyl)-2-(4-fluorophenyl)oxazol-5-yl)-4,4-difluorocyclohexane-carboxamide | 599.3 | 3.84 | 2,423 |
| 140 | 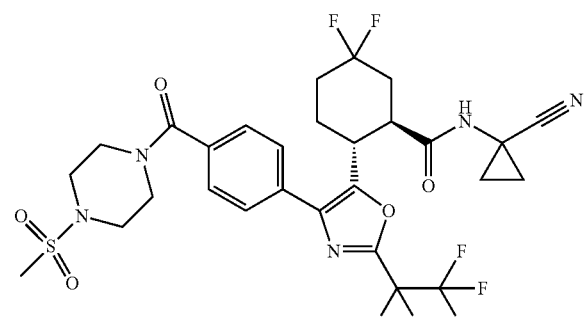 | (1R,2R)-N-(1-cyanocyclopropyl)-5,5-difluoro-2-(4-(4-(4-(methylsulfonyl)piperazine-1-carbonyl)phenyl)-2-(perfluoroethyl)oxazol-5-yl)cyclohexanecarboxamide | 680.5 | 1.93 | 372 |
| 141 | 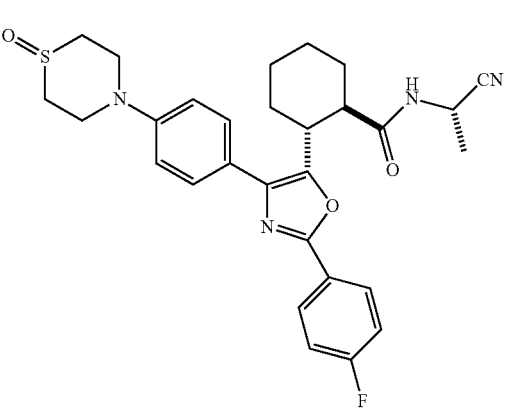 | (1R,2R)-N-((S)-1-cyanoethyl)-2-(2-(4-fluorophenyl)-4-(4-(1-oxidothiomorpholino)phenyl)oxazol-5-yl)cyclohexanecarboxamide | 535.2 | 0.90 | 167 |

-continued

| | Structure | Name | LC-MS m/z (M + H) | hrbC at K IP (nM) | hCat F IP (nM) |
|---|---|---|---|---|---|
| 142 | R or S | (1R,2R)-N-((R or S)-1-cyano-3,3,3-trifluoropropyl)-5,5-difluoro-2-(4-(4-(morpholine-4-carbonyl)phenyl)-2-(perfluoroethyl)oxazol-5-yl)cyclohexanecarboxamide | 659.6 | 1.06 | 446 |
| 143 | S or R | (1R,2R)-N-((S or R)-1-cyano-3,3,3-trifluoropropyl)-5,5-difluoro-2-(4-(4-(morpholine-4-carbonyl)phenyl)-2-(perfluoroethyl)oxazol-5-yl)cyclohexanecarboxamide | 659.5 | 0.54 | 14 |
| 144 | R or S | (1R,2R)-N-((R or S)-cyano(tetrahydro-2H-pyran-4-yl)methyl)-5,5-difluoro-2-(4-(4-(morpholine-4-carbonyl)phenyl)-2-(perfluoroethyl)oxazol-5-yl)cyclohexanecarboxamide | 661.2 | 1,517 | 10,000 |
| 145 | S or R | (1R,2R)-N-((S or R)-cyano(tetrahydro-2H-pyran-4-yl)methyl)-5,5-difluoro-2-(4-(4-(morpholine-4-carbonyl)phenyl)-2-(perfluoroethyl)oxazol-5-yl)cyclohexanecarboxamide | 661.3 | 3.00 | 1,086 |

| | Structure | Name | LC-MS m/z (M + H) | hrbC at K IP (nM) | hCat F IP (nM) |
|---|---|---|---|---|---|
| 146 | 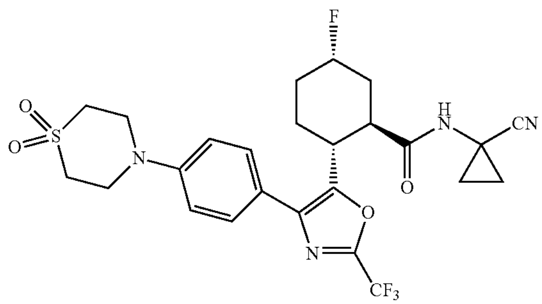 [SMILES: N#CC1(NC(=O)[C@@H]2C[C@@H](F)CC[C@H]2c2oc(C(F)(F)F)nc2-c2ccc(N3CCS(=O)(=O)CC3)cc2)CC1] | (1R,2R,5S)-N-(1-cyanocyclopropyl)-2-(4-(4-(1,1-dioxidothiomorpholino)phenyl)-2-(trifluoromethyl)oxazol-5-yl)-5-fluorocyclohexane-carboxamide | 555.1 | 1.92 | 352 |
| 147 | 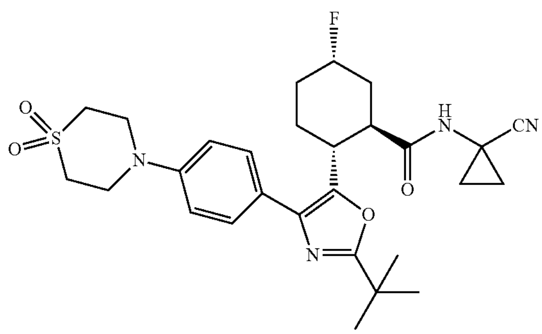 [SMILES: CC(C)(C)c1nc(-c2ccc(N3CCS(=O)(=O)CC3)cc2)c([C@@H]2CC[C@H](F)C[C@H]2C(=O)NC2(C#N)CC2)o1] | (1R,2R,5S)-2-(2-(tert-butyl)-4-(4-(1,1-dioxidothiomorpholino)phenyl)oxazol-5-yl)-N-(1-cyanocyclopropyl)-5-fluorocyclohexane-carboxamide | 543.2 | 1.50 | 2,415 |
| 148 | 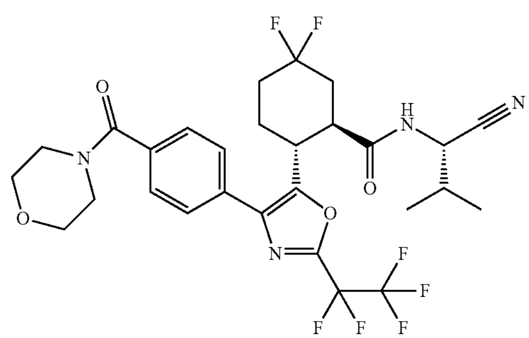 [SMILES: CC(C)[C@@H](C#N)NC(=O)[C@@H]1CC(F)(F)CC[C@H]1c1oc(C(F)(F)C(F)(F)F)nc1-c1ccc(C(=O)N2CCOCC2)cc1] | (1R,2R)-N-((S)-1-cyano-2-methylpropyl)-5,5-difluoro-2-(4-(4-(morpholine-4-carbonyl)phenyl)-2-(perfluoroethyl)oxazol-5-yl)cyclohexanecarboxamide | 619.2 | 1.03 | 280 |
| 149 | 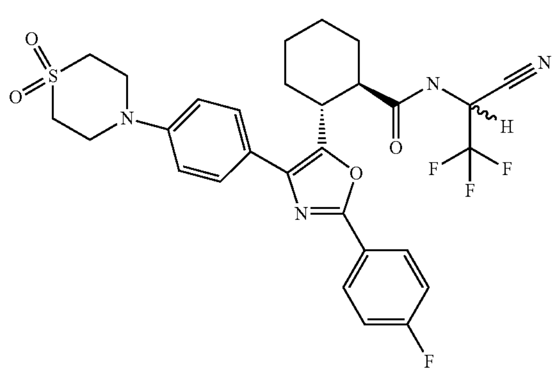 [SMILES: N#CC(NC(=O)[C@@H]1CCCC[C@H]1c1oc(-c2ccc(F)cc2)nc1-c1ccc(N2CCS(=O)(=O)CC2)cc1)C(F)(F)F] | (1R,2R)-N-((S and R)-1-cyano-2,2,2-trifluoroethyl)-2-(4-(4-(1,1-dioxidothiomorpholino)phenyl)-2-(4-fluorophenyl)oxazol-5-yl)cyclohexanecarboxamide | 605.4 | 1.30 | 53 |

-continued

| | Structure | Name | LC-MS m/z (M + H) | hrbC at K IP (nM) | hCat F IP (nM) |
|---|---|---|---|---|---|
| 150 | 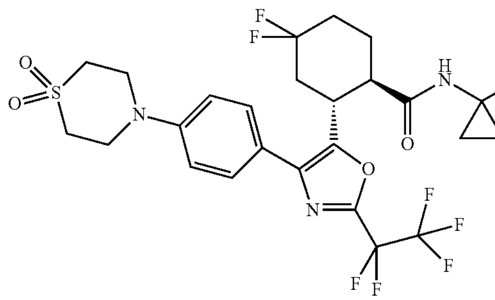 | (1R,2R)-N-(1-cyanocyclopropyl)-2-(4-(4-(1,1-dioxidothiomorpholino)phenyl)-2-(perfluoroethyl)oxazol-5-yl)-4,4-difluorocyclohexanecarboxamide | 623.0 | 4.70 | 10,000 |
| 151 | 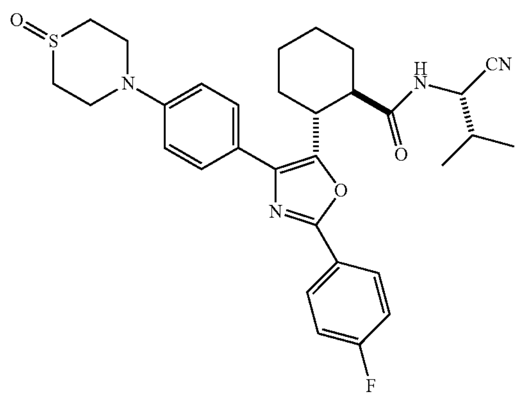 | (1R,2R)-N-((S)-1-cyano-2-methylpropyl)-2-(2-(4-fluorophenyl)-4-(4-(1-oxidothiomorpholino)phenyl)oxazol-5-yl)cyclohexanecarboxamide | 563.2 | 3.11 | 628 |
| 152 | 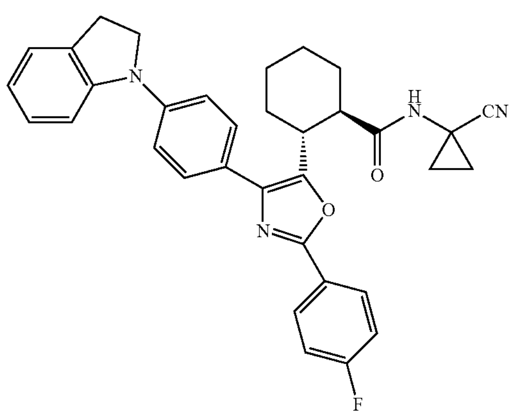 [SMILES: N#CC1(NC(=O)[C@@H]2CCCC[C@H]2c2oc(-c3ccc(F)cc3)nc2-c2ccc(N3CCc4ccccc43)cc2)CC1] | (1R,2R)-N-(1-cyanocyclopropyl)-2-(2-(4-fluorophenyl)-4-(4-(indolin-1-yl)phenyl)oxazol-5-yl)cyclohexanecarboxamide | 547.2 | 89.72 | 839 |
| 153 | 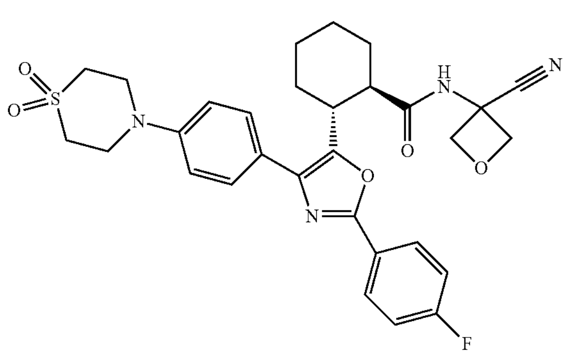 [SMILES: N#CC1(NC(=O)[C@@H]2CCCC[C@H]2c2oc(-c3ccc(F)cc3)nc2-c2ccc(N3CCS(=O)(=O)CC3)cc2)COC1] | (1R,2R)-N-(3-cyanooxetan-3-yl)-2-(4-(4-(1,1-dioxidothiomorpholino)phenyl)-2-(4-fluorophenyl)oxazol-5-yl)cyclohexanecarboxamide | 579.2 | 0.67 | 210 |

-continued

| | Structure | Name | LC-MS m/z (M + H) | hrbC at K IP (nM) | hCat F IP (nM) |
|---|---|---|---|---|---|
| 154 | 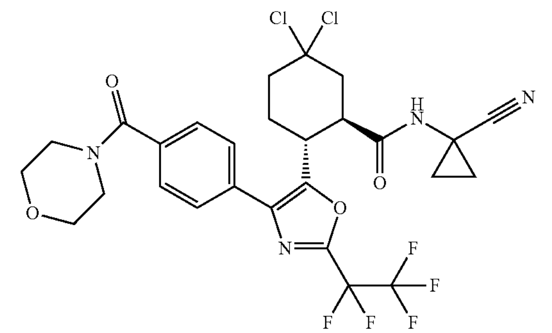 [SMILES: N#CC1(NC(=O)[C@@H]2CC(Cl)(Cl)CC[C@H]2c2oc(C(F)(F)C(F)(F)F)nc2-c2ccc(C(=O)N3CCOCC3)cc2)CC1] | (1R,2R)-5,5-dichloro-N-(1-cyanocyclopropyl)-2-(4-(4-(morpholine-4-carbonyl)phenyl)-2-(perfluoroethyl)oxazol-5-yl)cyclohexanecarboxamide | 635.1 | 0.68 | 259 |
| 155 | 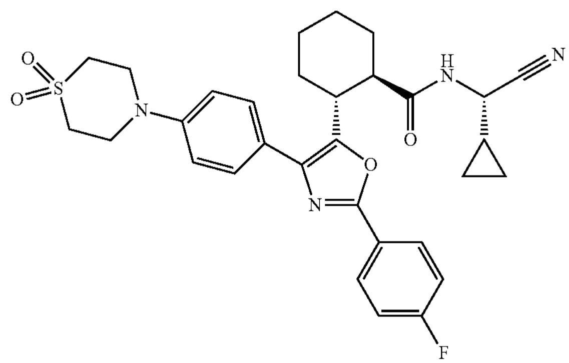 [SMILES: N#C[C@@H](NC(=O)[C@@H]1CCCC[C@H]1c1oc(-c2ccc(F)cc2)nc1-c1ccc(N2CCS(=O)(=O)CC2)cc1)C1CC1] | (1R,2R)-N-((S)-cyano(cyclopropyl)methyl)-2-(4-(4-(1,1-dioxidothiomorpholino)phenyl)-2-(4-fluorophenyl)oxazol-5-yl)cyclohexanecarboxamide | 577.5 | 0.73 | 37 |
| 156 | 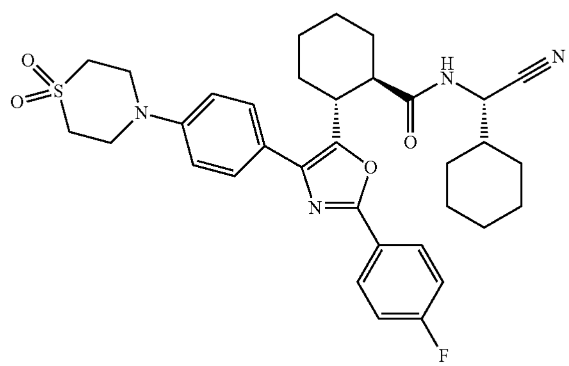 [SMILES: N#C[C@@H](NC(=O)[C@@H]1CCCC[C@H]1c1oc(-c2ccc(F)cc2)nc1-c1ccc(N2CCS(=O)(=O)CC2)cc1)C1CCCCC1] | (1R,2R)-N-((S)-cyano(cyclohexyl)methyl)-2-(4-(4-(1,1-dioxidothiomorpholino)phenyl)-2-(4-fluorophenyl)oxazol-5-yl)cyclohexanecarboxamide | 619.5 | 2.41 | 179 |
| 157 | 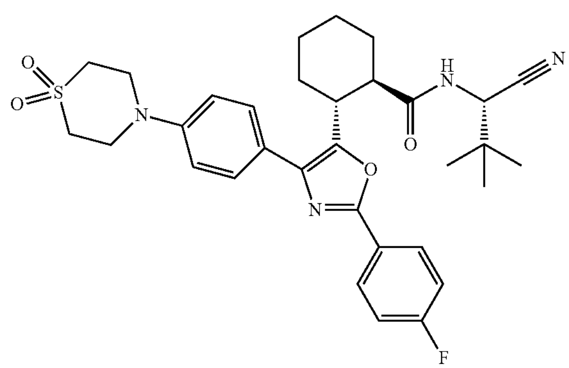 [SMILES: CC(C)(C)[C@@H](C#N)NC(=O)[C@@H]1CCCC[C@H]1c1oc(-c2ccc(F)cc2)nc1-c1ccc(N2CCS(=O)(=O)CC2)cc1] | (1R,2R)-N-((S)-1-cyano-2,2-dimethylpropyl)-2-(4-(4-(1,1-dioxidothiomorpholino)phenyl)-2-(4-fluorophenyl)oxazol-5-yl)cyclohexanecarboxamide | 593.5 | 288.80 | 2,329 |

| | | LC-MS m/z (M + H) | hrbC at K IP (nM) | hCat F IP (nM) |
|---|---|---|---|---|
| Structure | Name | | | |
| 158 [structure] R or S | (1R,2R)-N-((R or S)-1-cyano-2-hydroxy-2-methylpropyl)-2-(4-(4-(1,1-dioxidothiomorpholino)phenyl)-2-(4-fluorophenyl)oxazol-5-yl)cyclohexanecarboxamide | 595.5 | 9,745.00 | 10,000 |
| 159 [structure] S or R | (1R,2R)-N-((S or R)-1-cyano-2-hydroxy-2-methylpropyl)-2-(4-(4-(1,1-dioxidothiomorpholino)phenyl)-2-(4-fluorophenyl)oxazol-5-yl)cyclohexanecarboxamide | 595.5 | 43.20 | 6,860 |

Pharmaceutical Composition

As a specific embodiment of this invention, 100 mg of a compound of Example 1, is formulated with sufficient finely divided lactose to provide a total amount of 580 to 590 mg to fill a size 0, hard-gelatin capsule.

What is claimed is:

1. A compound of the formula:

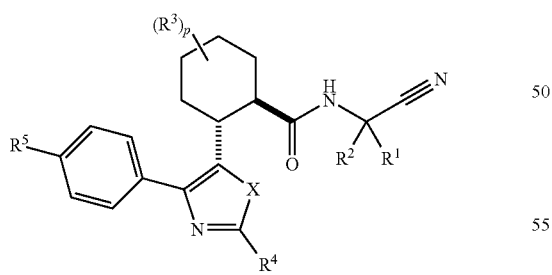

wherein X is oxygen or sulfur;

$R^1$ is hydrogen, $C_{1-6}$ alkyl, $C_{2-6}$ alkenyl, $C_{3-8}$ cycloalkyl or heterocyclyl, wherein said alkyl and alkenyl groups are optionally substituted with $C_{3-6}$ cycloalkyl, one to six halo, hydroxy or $R^8$;

and wherein said cycloalkyl and heterocyclyl groups are optionally substituted with one or two substituents selected from the group consisting of $C_{1-6}$ alkyl, halo, $OR^6$ and keto;

$R^2$ is hydrogen, $C_{1-6}$ alkyl or $C_{2-6}$ alkenyl wherein said alkyl and alkenyl groups are optionally substituted with $C_{3-6}$ cycloalkyl, one to six halo or $R^8$;

or $R^1$ and $R^2$ can be taken together with the carbon atom to which they are attached to form a $C_{3-8}$ cycloalkyl or heterocyclyl ring wherein said cycloalkyl and heterocyclyl rings are optionally substituted with one or two substituents independently selected from the group consisting of $R^6$, $C_{1-6}$ haloalkyl and halo;

Each $R^3$ is independently selected from the group consisting of hydrogen, halo and $C_{1-2}$ alkyl, wherein said alkyl group is optionally substituted with one to three halo; or two $R^3$ groups can be taken together with the carbon atom to which they are attached to form a $C_{3-4}$ cycloalkyl ring, wherein said ring is optionally substituted with one to three halo;

$R^4$ is hydrogen, $C_{1-6}$ alkyl, $C_{2-6}$ alkenyl, $C_{2-3}$ alkynyl, $NR^6R^7$, $OR^6$, $OR^8$ or $R^8$ wherein said alkyl groups are optionally substituted with one to six substituents independently selected from the group consisting of $OR^7$, halo, hydroxy, cyano and $R^8$;

$R^5$ is hydrogen, $C_{1-6}$ alkyl, $C_{2-6}$ alkenyl, aryl, heteroaryl, $C_{3-8}$ cycloalkyl, heterocyclyl, $C(O)NR^6R^8$, $C(O)R^8$ or $NR^6C(O)OR^7$, wherein said aryl, heteroaryl, $C_{3-8}$ cycloalkyl and heterocyclyl groups are optionally substituted with one to five substituents independently selected from the group consisting of $C_{1-6}$ alkyl, halo, oxo, cyano, $C_{1-6}$ haloalkyl and $SO_mR^6$;

R⁶ is hydrogen or C₁₋₆ alkyl which is optionally substituted with one to three substituents independently selected from the group consisting of halo, hydroxy, cyano and O(C₁₋₆ alkyl);

R⁷ is hydrogen or C₁₋₆ alkyl which is optionally substituted with one to three substituents independently selected from the group consisting of halo, hydroxy, cyano and O(C₁₋₆ alkyl);

R⁸ is C₃₋₈ cycloalkyl, aryl, heteroaryl or heterocyclyl, wherein said cycloalkyl, aryl, heteroaryl and heterocyclyl groups are optionally substituted with one to four substituents independently selected from the group consisting of halo, cyano, oxo, C₁₋₆ haloalkyl, R⁶, OR⁶, C₃₋₆ cycloalkyl, aryl, heteroaryl, heterocyclyl, SO_mR⁶ and SF₅;

m is an integer from zero to two;

p is an integer from zero to two;

or a pharmaceutically acceptable salt thereof.

2. The compound of claim 1 wherein R¹ is hydrogen, C₁₋₃ alkyl, C₃₋₈ cycloalkyl or heterocyclyl, wherein said alkyl group is optionally substituted with one to six halo;

or a pharmaceutically acceptable salt thereof.

3. The compound of claim 2 wherein R² is hydrogen or C₁₋₃ alkyl, wherein said alkyl group is optionally substituted with one to six halo; or a pharmaceutically acceptable salt thereof.

4. The compound of claim 1 wherein or R¹ and R² can be taken together with the carbon atom to which they are attached to form a C₃₋₆ cycloalkyl ring; or a pharmaceutically acceptable salt thereof.

5. The compound of claim 1 wherein each R³ is independently selected from the group consisting of hydrogen or halo, or two R³ groups can be taken together with the carbon atom to which they are attached to form a C₃₋₄ cycloalkyl ring, wherein said ring is optionally substituted with one to three halo; or a pharmaceutically acceptable salt thereof.

6. The compound of claim 5 wherein R⁴ is hydrogen, C₁₋₆ alkyl, OR⁶ or R⁸, wherein said alkyl groups are optionally substituted with one to six substituents independently selected from the group consisting of OR⁷, halo, hydroxy, cyano and R⁸; or a pharmaceutically acceptable salt thereof.

7. The compound of claim 6 wherein R⁵ is heteroaryl, heterocyclyl, C(O)NR⁶R⁸, C(O)R⁸ or NR⁶C(O)OR⁷, wherein said heteroaryl and heterocyclyl groups are optionally substituted with one to five substituents independently selected from the group consisting of C₁₋₆ alkyl, halo, oxo, cyano, C₁₋₆ haloalkyl and SO_mR⁶; or a pharmaceutically acceptable salt thereof.

8. The compound of claim 1 which is:

(1R,2R)-N-(1-cyanocyclopropyl)-2-(2-(3,4-difluorophenyl)-4-(4-(1,1-dioxidothiomorpholino)phenyl)oxazol-5-yl)cyclohexanecarboxamide;

(1R,2R)-N-(1-cyanocyclopropyl)-5,5-difluoro-2-(4-(4-(morpholine-4-carbonyl)phenyl)-2-(perfluoroethyl)oxazol-5-yl)cyclohexanecarboxamide;

(1R,2R)-N-(1-cyanocyclopropyl)-2-(4-(4-(1,1-dioxidothiomorpholino)phenyl)-2-(perfluoroethyl)oxazol-5-yl)cyclohexanecarboxamide;

(1R,2R)-N-(1-cyanocyclopropyl)-2-(2-(4,4-difluoropiperidin-1-yl)-4-(4-(1,1-dioxidothiomorpholino)phenyl)oxazol-5-yl)cyclohexanecarboxamide;

(1R,2R)-2-(2-(3-chlorophenyl)-4-(4-(1,1-dioxidothiomorpholino)phenyl)oxazol-5-yl)-N-(1-cyanocyclopropyl)cyclohexanecarboxamide;

(1R,2R)-2-(2-(3-chloro-2-fluorophenyl)-4-(4-(1,1-dioxidothiomorpholino)phenyl)oxazol-5-yl)-N-(1-cyanocyclopropyl)cyclohexanecarboxamide;

(1R,2R)-N-(1-Cyanocyclopropyl)-2-{4-[4-(1,1-dioxido-1λ⁶-thiomorpholin-4-yl)phenyl]-2-(4-fluorophenyl)-1,3-oxazol-5-yl}cyclohexanecarboxamide;

(1S,3R,4R,6R or 1R,3R,4R,6S)-N-(1-Cyanocyclopropyl)-4-(4-(4-(1,1-dioxidothiomorpholino)phenyl)-2-(5-fluoropyridin-2-yl)oxazol-5-yl)bicyclo[4.1.0]heptane-3-carboxamide;

(1R,3R,4R,6S or 1S,3R,4R,6R)-N-(1-cyanocyclopropyl)-4-(4-(4-(1,1-dioxidothiomorpholino)phenyl)-2-(5-fluoropyridin-2-yl)oxazol-5-yl)bicyclo[4.1.0]heptane-3-carboxamide;

(1R,2R)-2-(2-(tert-butyl)-4-(4-(1,1-dioxidothiomorpholino)phenyl)thiazol-5-yl)-N-(1-cyanocyclopropyl)cyclohexanecarboxamide;

(1R,2R)-2-(2-(tert-butyl)-4-(4-(1,1-dioxidothiomorpholino)phenyl)oxazol-5-yl)-N-(1-cyanocyclopropyl)cyclohexanecarboxamide;

(1R,2R)-N-(cyanomethyl)-2-(4-(4-(1,1-dioxidothiomorpholino)phenyl)-2-methyloxazol-5-yl)-5,5-difluorocyclohexanecarboxamide;

(1R,2R)-N-(1-cyanocyclopropyl)-2-(4-(4-(1,1-dioxidothiomorpholino)phenyl)-2-(trifluoromethyl)oxazol-5-yl)cyclohexanecarboxamide;

(1R,2R)-N-(1-cyanocyclopropyl)-2-(4-(4-(1,1-dioxidothiomorpholino)phenyl)-2-methyloxazol-5-yl)cyclohexanecarboxamide;

(1R,2R)-N-(1-cyanocyclopropyl)-2-(4-(4-(1,1-dioxidothiomorpholino)phenyl)-2-(2,2,2-trifluoroethyl)oxazol-5-yl)cyclohexanecarboxamide;

(1R,2R)-N-(1-cyanocyclopropyl)-2-(4-(4-(1,1-dioxidothiomorpholino)phenyl)-2-(2,2,2-trifluoroethyl)oxazol-5-yl)-5,5-difluorocyclohexanecarboxamide;

(1R,2R)-N-(1-cyanocyclopropyl)-2-(2-(4-fluorophenyl)-4-(4-morpholinophenyl)oxazol-5-yl)cyclohexanecarboxamide;

(1R,2R)-N-(1-cyanocyclopropyl)-2-(4-(4-(1,1-dioxidothiomorpholino)phenyl)-2-methyloxazol-5-yl)-5,5-difluorocyclohexanecarboxamide;

(1R,2R)-2-(2-(tert-butyl)-4-(4-(1,1-dioxidothiomorpholino)phenyl)oxazol-5-yl)-N-(1-cyanocyclopropyl)-5,5-difluorocyclohexanecarboxamide;

(1R,2R)-N-(1-cyanocyclopropyl)-2-(4-(4-(1,1-dioxidothiomorpholino)phenyl)-2-(4-fluorophenyl)oxazol-5-yl)-5,5-difluorocyclohexanecarboxamide;

N-(1-cyanocyclopropyl)-4-(5-((1R,2R)-2-((1-cyanocyclopropyl)carbamoyl)cyclohexyl)-2-methyloxazol-4-yl)benzamide;

(1R,2R)-N-(1-cyanocyclopropyl)-2-(2-methyl-4-(4-(morpholine-4-carbonyl)phenyl)oxazol-5-yl)cyclohexanecarboxamide;

(1R,2R)-N-(1-cyanocyclopropyl)-2-(4-(4-(3-(methylsulfonyl)azetidin-1-yl)phenyl)-2-(perfluoroethyl)oxazol-5-yl)cyclohexanecarboxamide;

(1R,2R)-N-(1-cyanocyclopropyl)-5,5-difluoro-2-(2-(4-fluorophenyl)-4-(4-(morpholine-4-carbonyl)phenyl)oxazol-5-yl)cyclohexanecarboxamide;

(1R,2R)-N-(1-cyanocyclopropyl)-2-(4-(4-(3-(methylsulfonyl)azetidin-1-yl)phenyl)-2-(trifluoromethyl)oxazol-5-yl)cyclohexanecarboxamideyl)cyclohexanecarboxamide;

(1R,2R)-N-(1-cyanocyclopropyl)-2-(4-(4-(morpholine-4-carbonyl)phenyl)-2-(perfluoroethyl)oxazol-5-yl)cyclohexanecarboxamide;

(1R,2R)-N-(1-cyanocyclopropyl)-2-(2-(2,4-difluorophenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(pyridin-2-yl)oxazol-5-yl)cyclohexanecarboxamide;

(1R,2R)-N-(1-cyanocyclopropyl)-2-(4-(4-(1,1-dioxidothiomorpholino)phenyl)-2-(pyridin-3-yl)oxazol-5-yl)cyclohexanecarboxamide;

(1R,2R)-N-(1-cyanocyclopropyl)-2-(4-(4-(1,1-dioxidothiomorpholino)phenyl)-2-(3-fluoropyridin-4-yl)oxazol-5-yl)cyclohexanecarboxamide;

(1R,2R,5S)-N-(1-cyanocyclopropyl)-2-(4-(4-(1,1-dioxidothiomorpholino)phenyl)-2-(4-fluorophenyl)oxazol-5-yl)-5-fluorocyclohexanecarboxamide;

(1R,2R)-N-(1-cyanocyclopropyl)-2-(4-(4-(1,1-dioxidothiomorpholino)phenyl)-2-(5-fluoropyridin-2-yl)oxazol-5-yl)cyclohexanecarboxamide;

(1R,2R)-N-(1-cyanocyclopropyl)-2-(4-(4-(1,1-dioxidothiomorpholino)phenyl)-2-(5-fluoropyridin-3-yl)oxazol-5-yl)cyclohexanecarboxamide;

(1R,2R)-N-(1-cyanocyclopropyl)-2-(2-(3,5-difluorophenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(pyrimidin-5-yl)oxazol-5-yl)cyclohexanecarboxamide;

(1R,2R)-2-(2-(3-chloro-4-fluorophenyl)-4-(4-(1,1-dioxidothiomorpholino)phenyl)oxazol-5-yl)-N-(1-cyanocyclopropyl)cyclohexanecarboxamide;

(1R,2R)-2-(2-(2-chloro-4-fluorophenyl)-4-(4-(1,1-dioxidothiomorpholino)phenyl)oxazol-5-yl)-N-(1-cyanocyclopropyl)cyclohexanecarboxamide;

(1R,2R)-2-(2-(4-chlorophenyl)-4-(4-(1,1-dioxidothiomorpholino)phenyl)oxazol-5-yl)-N-(1-cyanocyclopropyl)cyclohexanecarboxamide;

(1R,2R)-N-(1-cyanocyclopropyl)-2-(2-(2,4-difluorophenyl)-4-(4-(3-(methylsulfonyl)azetidin-1-yl)phenyl)oxazol-5-yl)cyclohexanecarboxamide;

(1R,2R)-N-(1-cyanocyclopropyl)-2-(4-(4-(1,1dioxidothiomorpholino)phenyl)-2-(6-(trifluoro methyl)pyridin-3-yl)oxazol-5-yl)cyclohexanecarboxamide;

(1R,2R,5S)-N-(1-cyanocyclopropyl)-2-(2-(2,4-difluorophenyl)-4-(4-(1,1-dioxidothiomorpholino)phenyl)oxazol-5-yl)-5-fluorocyclohexanecarboxamide;

(1R,2R,5S)-N-(1-cyanocyclopropyl)-2-(4-(4-(1,1-dioxidothiomorpholino)phenyl)-2-(perfluoroethyl)oxazol-5-yl)-5-fluorocyclohexanecarboxamide;

(1R,2R)-N-(2-cyanopropan-2-yl)-2-(2-(2,4-difluorophenyl)-4-(4-(1,1-dioxidothiomorpholino)phenyl)oxazol-5-yl)cyclohexanecarboxamide;

(1R,2R)-N-(cyanomethyl)-2-(2-(2,4-difluorophenyl)-4-(4-(1,1-dioxidothiomorpholino)phenyl)oxazol-5-yl)cyclohexanecarboxamide;

(1R,2R)-N-((R or S)-1-cyanoethyl)-2-(2-(2,4-difluorophenyl)-4-(4-(1,1-dioxidothiomorpholino)phenyl)oxazol-5-yl)cyclohexanecarboxamide;

(1R,2R)-N-((S or R)-1-cyanoethyl)-2-(2-(2,4-difluorophenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-morpholinooxazol-5-yl)cyclohexanecarboxamide;

tert-butyl (4-(5-((1R,2R)-2-((1-cyanocyclopropyl)carbamoyl)cyclohexyl)-2-(4-fluorophenyl)oxazol-4-yl)phenyl)(methyl)carbamate.

tert-butyl (4-(5-((1R,2R)-2-((1-cyanocyclopropyl)carbamoyl)cyclohexyl)-2-(4-fluorophenyl)oxazol-4-yl)phenyl)carbamate;

(1R,2R)-2-(2-benzyl-4-(4-(1,1-dioxidothiomorpholino)phenyl)oxazol-5-yl)-N-(1-cyanocyclopropyl)cyclohexanecarboxamide;

(1R,2R)-N-(1-cyanocyclopropyl)-2-(2-(cyclohexylmethyl)-4-(4-(1,1-dioxidothiomorpholino)phenyl)oxazol-5-yl)cyclohexanecarboxamide;

(1R,2R)-N-(1-cyanocyclopropyl)-2-(2-(4,4-difluoro-1-methylcyclohexyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(1,1,4-trimethylsilinan-4-yl)oxazol-5-yl)cyclohexanecarboxamide;

(1R,2R)-N-(1-cyanocyclopropyl)-2-(4-(4-(1,1-dioxidothiomorpholino)phenyl)-2-methylthiazol-5-yl)cyclohexanecarboxamide;

(1R,2R)-N-(1-cyanocyclopropyl)-2-(2-methyl-4-(4-(3-(methylsulfonyl)azetidin-1-yl)phenyl)thiazol-5-yl)cyclohexanecarboxamide;

(1R,2R)-N-(1-cyanocyclopropyl)-2-(4-(4-(1,1-dioxidothiomorpholino)phenyl)-2-(4-fluorophenyl)thiazol-5-yl)cyclohexanecarboxamide;

(1R,2R)-N-(1-cyanocyclopropyl)-2-(4-(4-(1,1-dioxidothiomorpholino)phenyl)-2-(2,2,2-trifluoroethyl)thiazol-5-yl)-5,5-difluorocyclohexanecarboxamide;

(1R,2R)-2-(2-(tert-butyl)-4-(4-(1,1-dioxidothiomorpholino)phenyl)thiazol-5-yl)-N-(1-cyanocyclopropyl)-5,5-difluorocyclohexanecarboxamide;

(1R,2R)-N-(1-cyanocyclopropyl)-2-(4-(4-(1,1-dioxidothiomorpholino)phenyl)-2-methylthiazol-5-yl)-5,5-difluorocyclohexanecarboxamide;

(1R,2R)-N-(1-cyanocyclopropyl)-2-(4-(4-(1,1-dioxidothiomorpholino)phenyl)-2-(trifluoromethyl)thiazol-5-yl)cyclohexanecarboxamide;

(1R,2R)-N-(1-cyanocyclopropyl)-2-(4-(4-(1,1-dioxidothiomorpholino)phenyl)-2-(4-(trifluoromethoxy)phenyl)oxazol-5-yl)cyclohexanecarboxamide;

(1R,2R)-N-(1-cyanocyclopropyl)-2-(4-(4-(1,1-dioxidothiomorpholino)phenyl)-2-(3-fluorophenyl)oxazol-5-yl)cyclohexanecarboxamide;

(1R,2R)-N-(1-cyanocyclopropyl)-2-(4-(4-(1,1-dioxidothiomorpholino)phenyl)-2-(2-(trifluoromethoxy)phenyl)oxazol-5-yl)cyclohexanecarboxamide;

(1R,2R)-N-(1-cyanocyclopropyl)-2-(2-(4-(difluoromethoxy)phenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(4-(trifluoromethyl)phenyl)oxazol-5-yl)cyclohexanecarboxamide;

(1R,2R)-N-(1-cyanocyclopropyl)-2-(4-(4-(1,1-dioxidothiomorpholino)phenyl)-2-(3-(trifluoromethyl)phenyl)oxazol-5-yl)cyclohexanecarboxamide (1R,2R)-N-(1-cyanocyclopropyl)-2-(4-(4-(1,1-dioxidothiomorpholino)phenyl)-2-(2-fluorophenyl)oxazol-5-yl)cyclohexanecarboxamide;

(1R,2R)-N-(1-cyanocyclopropyl)-2-(2-(3-(difluoromethoxy)phenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(2-(trifluoromethyl)phenyl)oxazol-5-yl)cyclohexanecarboxamide;

(1R,2R)-N-(1-cyanocyclopropyl)-2-(4-(4-(1,1-dioxidothiomorpholino)phenyl)-2-(4-methoxyphenyl)oxazol-5-yl)cyclohexanecarboxamide;

(1R,2R)-N-(1-cyanocyclopropyl)-2-(4-(4-(1,1-dioxidothiomorpholino)phenyl)-2-(3-methoxyphenyl)oxazol-5-yl)cyclohexanecarboxamide;

(1R,2R)-N-(1-cyanocyclopropyl)-2-(4-(4-(1,1-dioxidothiomorpholino)phenyl)-2-(2-methoxyphenyl)oxazol-5-yl)cyclohexanecarboxamide;

(1R,2R)-N-(1-cyanocyclopropyl)-2-(4-(4-(1,1-dioxidothiomorpholino)phenyl)-2-(2-methylthiazol-5-yl)oxazol-5-yl)cyclohexanecarboxamide;

(1R,2R)-N-(1-cyanocyclopropyl)-2-(2-(4-cyanophenyl)-4-(4-(1,1-dioxidothiomorpholino)phenyl)oxazol-5-yl)cyclohexanecarboxamide;

(1R,2R)-2-(2-(2-chlorophenyl)-4-(4-(1,1-dioxidothiomorpholino)phenyl)oxazol-5-yl)-N-(1-cyanocyclopropyl)cyclohexanecarboxamide;

(1R,2R)-2-(2-(4-chloro-3-fluorophenyl)-4-(4-(1,1-dioxidothiomorpholino)phenyl)oxazol-5-yl)-N-(1-cyanocyclopropyl)cyclohexanecarboxamide;

(1R,2R)-N-(1-cyanocyclopropyl)-2-(2-(3-cyclopropylphenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(thiazol-2-yl)oxazol-5-yl)cyclohexanecarboxamide;

(1R,2R)-N-(1-cyanocyclopropyl)-2-(2-(2-cyclopropylphenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(3-(trifluoromethyl)pyridin-2-yl)oxazol-5-yl)cyclohexanecarboxamide;

(1R,2R)-N-(1-cyanocyclopropyl)-2-(4-(4-(1,1-dioxidothiomorpholino)phenyl)-2-(5-(trifluoromethyl)pyridin-2-yl)oxazol-5-yl)cyclohexanecarboxamide;

(1R,2R)-N-(1-cyanocyclopropyl)-2-(4-(4-(1,1-dioxidothiomorpholino)phenyl)-2-(2-methylpyrimidin-4-yl)oxazol-5-yl)cyclohexanecarboxamide;

(1R,2R)-N-(1-cyanocyclopropyl)-2-(4-(4-(1,1-dioxidothiomorpholino)phenyl)-2-(4-(trifluoromethyl)pyridin-2-yl)oxazol-5-yl)cyclohexanecarboxamide;

(1R,2R)-N-(1-cyanocyclopropyl)-2-(4-(4-(1,1-dioxidothiomorpholino)phenyl)-2-(3-fluoropyridin-2-yl)oxazol-5-yl)cyclohexanecarboxamide;

(1R,2R)-N-(1-cyanocyclopropyl)-2-(4-(4-(1,1-dioxidothiomorpholino)phenyl)-2-(2-(trifluoromethyl)pyrimidin-5-yl)oxazol-5-yl)cyclohexanecarboxamide;

(1R,2R)-N-(1-cyanocyclopropyl)-2-(4-(4-(1,1-dioxidothiomorpholino)phenyl)-2-(3-(trifluoromethoxy)phenyl)oxazol-5-yl)cyclohexanecarboxamide;

(1R,2R)-N-(1-cyanocyclopropyl)-2-(4-(4-((1R,4R and 1S,4S)-2,2-dioxido-2-thia-5-azabicyclo[2.2.1]heptan-5-yl)phenyl)-2-(4-fluorophenyl)oxazol-5-yl)cyclohexanecarboxamide;

(1R,2R)-N-(1-cyanocyclopropyl)-2-(4-(4-(1,1-dioxidothiomorpholino)phenyl)-2-(5-(trifluoromethyl)pyridin-3-yl)oxazol-5-yl)cyclohexanecarboxamide;

(1R,2R)-2-(2-(4-(tert-butyl)phenyl)-4-(4-(1,1-dioxidothiomorpholino)phenyl)oxazol-5-yl)-N-(1-cyanocyclopropyl)cyclohexanecarboxamide;

(1R,2R)-N-(1-cyanocyclopropyl)-2-(4-(4-(1,1-dioxidothiomorpholino)phenyl)-2-(pyrimidin-2-yl)oxazol-5-yl)cyclohexanecarboxamide;

(1R,2R)-N-(1-cyanocyclopropyl)-2-(2-(6-(difluoromethoxy)pyridin-3-yl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(5-(1,1-dioxidothiomorpholino)pyridin-3-yl)oxazol-5-yl)cyclohexanecarboxamide;

(1R,2R)-N-(1-cyanocyclopropyl)-2-(2-(3-cyanophenyl)-4-(4-(1,1-dioxidothiomorpholino)phenyl)oxazol-5-yl)cyclohexanecarboxamide;

(1R,2R)-2-(2-(4-chloro-2-fluorophenyl)-4-(4-(1,1-dioxidothiomorpholino)phenyl)oxazol-5-yl)-N-(1-cyanocyclopropyl)cyclohexanecarboxamide;

(1R,2R)-2-(2-(5-chloropyridin-3-yl)-4-(4-(1,1-dioxidothiomorpholino)phenyl)oxazol-5-yl)-N-(1-cyanocyclopropyl)cyclohexanecarboxamide;

(1R,2R)-N-(1-cyanocyclopropyl)-2-(2-(2-(difluoromethoxy)phenyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(pyridazin-3-yl)oxazol-5-yl)cyclohexanecarboxamide;

(1R,2R)-2-(2-(bicyclo[1.1.1]pentan-2-yl)-4-(4-(1,1-dioxidothiomorpholino)phenyl)oxazol-5-yl)-N-(1-cyanocyclopropyl)cyclohexanecarboxamide;

(1R,2R)-N-(1-cyanocyclopropyl)-2-(4-(4-(1,1-dioxidothiomorpholino)phenyl)-2-(4-methyltetrahydro-2H-pyran-4-yl)oxazol-5-yl)cyclohexanecarboxamide;

(1R,2R)-N-(1-cyanocyclopropyl)-2-(4-(4-(1,1-dioxidothiomorpholino)phenyl)-2-(6-(trifluoromethyl)pyridin-2-yl)oxazol-5-yl)cyclohexanecarboxamide;

(1R,2R)-N-(1-cyanocyclopropyl)-2-(2-(4-cyclopropylphenyl)-4-(4-(1,1-dioxidothiomorpholino)phenyl)oxazol-5-yl)cyclohexanecarboxamide;

(1R,2R)-2-(4-(3-bromo-4-(1,1-dioxidothiomorpholino)phenyl)-2-(4-fluorophenyl)oxazol-5-yl)-N-(1-cyanocyclopropyl)cyclohexanecarboxamide;

(1R,2R)-N-(1-cyanocyclopropyl)-2-(4-(4-(1,1-dioxidothiomorpholino)phenyl)-2-(2-methylpyrimidin-5-yl)oxazol-5-yl)cyclohexanecarboxamide;

(1R,2R)-N-(1-cyanocyclopropyl)-2-(4-(4-(1,1-dioxidothiomorpholino)phenyl)-2-(4-((trifluoromethyl)sulfonyl)phenyl)oxazol-5-yl)cyclohexanecarboxamide;

(1R,2R)-N-(1-cyanocyclopropyl)-2-(2-(2-cyanophenyl)-4-(4-(1,1-dioxidothiomorpholino)phenyl)oxazol-5-yl)cyclohexanecarboxamide;

(1R,2R)-N-(1-cyanocyclopropyl)-2-(2-(2,4-difluorophenyl)-4-(4-(1-imino-1-oxidothiomorpholino)phenyl)oxazol-5-yl)cyclohexanecarboxamide;

(1R,2R)-N-(1-cyanocyclopropyl)-2-(2-((1S,2R)-4,4-difluoro-2-methylcyclohexyl)-4-(4-(1,1-dioxidothiomorpholino)phenyl)oxazol-5-yl)cyclohexanecarboxamide;

(1R,2R)-N-(1-cyanocyclopropyl)-2-(2-((1S,2S)-4,4-difluoro-2-methylcyclohexyl)-4-(4-(1,1-dioxidothiomorpholino)phenyl)oxazol-5-yl)cyclohexanecarboxamide;

(1R,2R)-N-(1-cyanocyclopropyl)-2-(2-((1R,3R,5S and 1R,3S,5S)-8,8-difluorobicyclo[3.2.1]octan-3-yl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(1-(trifluoromethyl)cyclopropyl)oxazol-5-yl)cyclohexanecarboxamide;

(1R,2R)-N-(1-cyanocyclopropyl)-2-(4-(4-(1,1-dioxidothiomorpholino)phenyl)-2-((1R,4R and 1S,4S)-4-(trifluoromethyl)cyclohexyl)oxazol-5-yl)cyclohexanecarboxamide;

(1R,2R)-N-(cyanomethyl)-2-(4-(4-(1,1-dioxidothiomorpholino)phenyl)-2-(4-fluorophenyl)oxazol-5-yl)cyclohexanecarboxamide;

(1R,2R)-N-(1-cyanocyclopropyl)-2-(4-(4-(1,1-dioxidothiomorpholino)phenyl)-2-(2,2,3,3-tetramethylcyclopropyl)oxazol-5-yl)cyclohexanecarboxamide;

(1R,2R)-N-(1-cyanocyclopropyl)-2-(2-((R and S)-3,3-difluorocyclopentyl)-4-(4-(1,1-dioxidothiomorpholino)phenyl)oxazol-5-yl)cyclohexanecarboxamide;

(1R,2R)-N-(1-cyanocyclopropyl)-2-(4-(4-(1,1-dioxidothiomorpholino)phenyl)-2-(1,1,1-trifluoro-2-methylpropan-2-yl)oxazol-5-yl)cyclohexanecarboxamide;

(1R,2R)-N-(1-cyanocyclopropyl)-2-(4-(4-(1,1-dioxidothiomorpholino)phenyl)-2-((R and S)-2,2,2-trifluoro-1-methoxy-1-phenylethyl)oxazol-5-yl)cyclohexanecarboxamide;

(1R,2R)-N-(1-cyanocyclopropyl)-2-(4-(4-(1,1-dioxidothiomorpholino)phenyl)-2-((1R,3R and 1S,3S)-3-methoxycyclobutyl)oxazol-5-yl)cyclohexanecarboxamide;

(1R,2R)-2-(2-((1R,3R,5S and 1R,3S,5S)-bicyclo[3.1.0]hexan-3-yl)-4-(4-(1,1-dioxidothiomorpholino)phenyl)oxazol-5-yl)-N-(1-cyanocyclopropyl)cyclohexanecarboxamide;

(1R,2R)-N-(1-cyanocyclopropyl)-5,5-difluoro-2-(4-(4-(morpholine-4-carbonyl)phenyl)-2-(perfluoroethyl)oxazol-5-yl)cyclohexanecarboxamide;

(1R,2R)-N-(1-cyanocyclopropyl)-2-(2-(2,4-difluorophenyl)-4-(4-(morpholine-4-carbonyl)phenyl)oxazol-5-yl)cyclohexanecarboxamide;

(1R,2R)-N-((R or S)-1-cyanoethyl)-2-(4-(4-(1,1-dioxidothiomorpholino)phenyl)-2-(4-fluorophenyl)oxazol-5-yl)cyclohexanecarboxamide;

(1R,2R)-N-((S or R)-1-cyanoethyl)-2-(4-(4-(1,1-dioxidothiomorpholino)phenyl)-2-(4-fluorophenyl)oxazol-5-yl)cyclohexanecarboxamide;

(1R,2R)-N-((S or R)-1-cyano-2-methylpropyl)-2-(4-(4-(1,1-dioxidothiomorpholino)phenyl)-2-(4-fluorophenyl)oxazol-5-yl)cyclohexanecarboxamide;

(1R,2R)-N-((R or S)-1-cyano-2-methylpropyl)-2-(4-(4-(1,1-dioxidothiomorpholino)phenyl)-2-(4-fluorophenyl)oxazol-5-yl)cyclohexanecarboxamide;

(1R,2R)-N-((S or R)-1-cyanopropyl)-2-(4-(4-(1,1-dioxidothiomorpholino)phenyl)-2-(4-fluorophenyl)oxazol-5-yl)cyclohexanecarboxamide;

(1R,2R)-N-((R or S)-1-cyanopropyl)-2-(4-(4-(1,1-dioxidothiomorpholino)phenyl)-2-(4-fluorophenyl)oxazol-5-yl)cyclohexanecarboxamide;

(1R,2R)-N-((R)-cyano(tetrahydro-2H-pyran-4-yl)methyl)-2-(4-(4-(1,1-dioxidothiomorpholino)phenyl)-2-(4-fluorophenyl)oxazol-5-yl)cyclohexanecarboxamide;

(1R,2R)-N-((S)-cyano(tetrahydro-2H-pyran-4-yl)methyl)-2-(4-(4-(1,1-dioxidothiomorpholino)phenyl)-2-(4-fluorophenyl)oxazol-5-yl)cyclohexanecarboxamide;

(1R,2R)-N-(1-cyanocyclopropyl)-2-(2-(2,4-difluorophenyl)-4-(4-(4-(methylsulfonyl)piperazine-1-carbonyl)phenyl)oxazol-5-yl)cyclohexanecarboxamide;

(1R,2R)-N-(1-cyanocyclopropyl)-2-(2-(difluoro(phenyl)methyl)-4-(4-(1,1-dioxidothiomorpholino)phenyl)oxazol-5-yl)cyclohexanecarboxamide;

(1R,2R)-N-((R or S)-1-cyano-3,3,3-trifluoropropyl)-2-(4-(4-(1,1-dioxidothiomorpholino)phenyl)-2-(4-fluorophenyl)oxazol-5-yl)cyclohexanecarboxamide;

(1R,2R)-N-((S or R)-1-cyano-3,3,3-trifluoropropyl)-2-(4-(4-(1,1-dioxidothiomorpholino)phenyl)-2-(4-fluorophenyl)oxazol-5-yl)cyclohexanecarboxamide;

(1R,2R)-N-((2R or 2S)-1-cyano-2-methylcyclopropyl)-2-(4-(4-(1,1-dioxidothiomorpholino)phenyl)-2-(4-fluorophenyl)oxazol-5-yl)cyclohexanecarboxamide;

(1R,2R)-N-((2S or 2R)-1-cyano-2-methylcyclopropyl)-2-(4-(4-(1,1-dioxidothiomorpholino)phenyl)-2-(4-fluorophenyl)oxazol-5-yl)cyclohexanecarboxamide;

(1R,2R)-N-(1-cyanocyclopropyl)-2-(2-(4-fluorophenyl)-4-(4-(1-oxidothiomorpholino)phenyl)oxazol-5-yl)cyclohexanecarboxamide;

(1R,2R)-N-(cyanomethyl)-5,5-difluoro-2-(4-(4-(morpholine-4-carbonyl)phenyl)-2-(perfluoroethyl)oxazol-5-yl)cyclohexanecarboxamide;

(1R,2R)-N-((S)-1-cyanoethyl)-5,5-difluoro-2-(4-(4-(morpholine-4-carbonyl)phenyl)-2-(perfluoroethyl)oxazol-5-yl)cyclohexanecarboxamide;

(1R,2R,5R and 1R,2R,5S)-N-(1-cyanocyclopropyl)-5-(difluoromethyl)-2-(4-(4-(1,1-dioxidothiomorpholino)phenyl)-2-(4-fluorophenyl)oxazol-5-yl)cyclohexanecarboxamide;

(1R,2R)-N-(1-cyanocyclopropyl)-2-(4-(4-(1,1-dioxidothiomorpholino)phenyl)-2-(4-fluorophenyl)oxazol-5-yl)-4,4-difluorocyclohexanecarboxamide;

(1R,2R)-N-(1-cyanocyclopropyl)-5,5-difluoro-2-(4-(4-(methyl sulfonyl)piperazine-1-carbonyl)phenyl)-2-(perfluoroethyl)oxazol-5-yl)cyclohexanecarboxamide;

(1R,2R)-N-((S)-1-cyanoethyl)-2-(2-(4-fluorophenyl)-4-(4-(1-oxidothiomorpholino)phenyl)oxazol-5-yl)cyclohexanecarboxamide;

(1R,2R)-N-((R or S)-1-cyano-3,3,3-trifluoropropyl)-5,5-difluoro-2-(4-(4-(morpholine-4-carbonyl)phenyl)-2-(perfluoroethyl)oxazol-5-yl)cyclohexanecarboxamide;

(1R,2R)-N-((S or R)-1-cyano-3,3,3-trifluoropropyl)-5,5-difluoro-2-(4-(4-(morpholine-4-carbonyl)phenyl)-2-(perfluoroethyl)oxazol-5-yl)cyclohexanecarboxamide;

(1R,2R)-N-((R or S)-cyano(tetrahydro-2H-pyran-4-yl)methyl)-5,5-difluoro-2-(4-(4-(morpholine-4-carbonyl)phenyl)-2-(perfluoroethyl)oxazol-5-yl)cyclohexanecarboxamide;

(1R,2R)-N-((S or R)-cyano(tetrahydro-2H-pyran-4-yl)methyl)-5,5-difluoro-2-(4-(4-(morpholine-4-carbonyl)phenyl)-2-(perfluoroethyl)oxazol-5-yl)cyclohexanecarboxamide;

(1R,2R,5S)-N-(1-cyanocyclopropyl)-2-(4-(4-(1,1-dioxidothiomorpholino)phenyl)-2-(trifluoromethyl)oxazol-5-yl)-5-fluorocyclohexanecarboxamide;

(1R,2R,5S)-2-(2-(tert-butyl)-4-(4-(1,1-dioxidothiomorpholino)phenyl)oxazol-5-yl)-N-(1-cyanocyclopropyl)-5-fluorocyclohexanecarboxamide;

(1R,2R)-N-((S)-1-cyano-2-methylpropyl)-5,5-difluoro-2-(4-(4-(morpholine-4-carbonyl)phenyl)-2-(perfluoroethyl)oxazol-5-yl)cyclohexanecarboxamide;

(1R,2R)-N-((S and R)-1-cyano-2,2,2-trifluoroethyl)-2-(4-(4-(1,1-dioxidothiomorpholino)phenyl)-2-(4-fluorophenyl)oxazol-5-yl)cyclohexanecarboxamide;

(1R,2R)-N-(1-cyanocyclopropyl)-2-(4-(4-(1,1-dioxidothiomorpholino)phenyl)-2-(perfluoroethyl)oxazol-5-yl)-4,4-difluorocyclohexanecarboxamide;

(1R,2R)-N-((S)-1-cyano-2-methylpropyl)-2-(2-(4-fluorophenyl)-4-(4-(1-oxidothiomorpholino)phenyl)oxazol-5-yl)cyclohexanecarboxamide;

(1R,2R)-N-(1-cyanocyclopropyl)-2-(2-(4-fluorophenyl)-4-(4-(indolin-1-yl)phenyl)oxazol-5-yl)cyclohexanecarboxamide;

(1R,2R)-N-(3-cyanooxetan-3-yl)-2-(4-(4-(1,1-dioxidothiomorpholino)phenyl)-2-(4-fluorophenyl)oxazol-5-yl)cyclohexanecarboxamide;

(1R,2R)-5,5-dichloro-N-(1-cyanocyclopropyl)-2-(4-(4-(morpholine-4-carbonyl)phenyl)-2-(perfluoroethyl)oxazol-5-yl)cyclohexanecarboxamide;

(1R,2R)-N-((S)-cyano(cyclopropyl)methyl)-2-(4-(4-(1,1-dioxidothiomorpholino)phenyl)-2-(4-fluorophenyl)oxazol-5-yl)cyclohexanecarboxamide;

(1R,2R)-N-((S)-cyano(cyclohexyl)methyl)-2-(4-(4-(1,1-dioxidothiomorpholino)phenyl)-2-(4-fluorophenyl)oxazol-5-yl)cyclohexanecarboxamide;

(1R,2R)-N-((S)-1-cyano-2,2-dimethylpropyl)-2-(4-(4-(1,1-dioxidothiomorpholino)phenyl)-2-(4-fluorophenyl)oxazol-5-yl)cyclohexanecarboxamide;

(1R,2R)-N-((R or S)-1-cyano-2-hydroxy-2-methylpropyl)-2-(4-(4-(1,1-dioxidothiomorpholino)phenyl)-2-(4-fluorophenyl)oxazol-5-yl)cyclohexanecarboxamide; or (1R,2R)-N-((S or R)-1-cyano-2-hydroxy-2-methylpropyl)-2-(4-(4-(1,1-dioxidothiomorpholino)phenyl)-2-(4-fluorophenyl)oxazol-5-yl)cyclohexanecarboxamide;

or a pharmaceutically acceptable salt thereof.

9. A pharmaceutical composition comprising a compound of claim 1 and a pharmaceutically acceptable carrier.

10. A pharmaceutical composition comprising a compound of claim 1 and an agent selected from the group consisting of: an organic bisphosphonate, a selective estrogen receptor modulator, an estrogen receptor beta modulator, an androgen receptor modulator, an inhibitor of osteoclast proton ATPase, an inhibitor of HMG-CoA reductase, an integrin receptor antagonist, or an osteoblast anabolic agent, vitamin D, a synthetic Vitamin D analogue, a Nonsteroidal anti-inflammatory drug, a selective cyclooxygenase-2 inhibitor, an inhibitor of interleukin-1 beta, and a LOX/COX inhibitor, and the pharmaceutically acceptable salts and mixtures thereof.

11. A method of treating osteoporosis, glucocorticoid induced osteoporosis, Paget's disease, abnormally increased bone turnover, periodontal disease, tooth loss, bone fractures, rheumatoid arthritis, osteoarthritis, periprosthetic osteolysis, osteogenesis imperfecta, atherosclerosis, obesity, glaucoma, chronic obstructive pulmonary disease, metastatic bone disease, hypercalcemia of malignancy or multiple myeloma in a mammal in need thereof, comprising administering a therapeutically effective amount of a compound of claim 1 or a pharmaceutically acceptable salt thereof.

12. The method of claim 11 comprising administering an agent selected from the group consisting of: an organic bisphosphonate, a selective estrogen receptor modulator, an androgen receptor modulator, an inhibitor of osteoclast proton ATPase, an inhibitor of HMG-CoA reductase, an integrin receptor antagonist, an osteoblast anabolic agent, vitamin D, a synthetic Vitamin D analogue, a Nonsteroidal anti-inflammatory drug, a selective cyclooxygenase-2 inhibitor, an inhibitor of interleukin-1 beta, and a LOX/COX inhibitor, and the pharmaceutically acceptable salts and mixtures thereof.

13. A method of treating osteoporosis in a mammal in need thereof, comprising administering a compound of claim 1 or a pharmaceutically acceptable salt thereof.

14. (1R,2R)-N-(1-Cyanocyclopropyl)-2-{4-[4-(1,1-dioxo-1$\lambda^6$-thiomorpholin-4-yl)phenyl]-2-(4-fluorophenyl)-1,3-oxazol-5-yl}cyclohexanecarboxamide, or a pharmaceutically acceptable salt thereof.

15. The compound of the formula

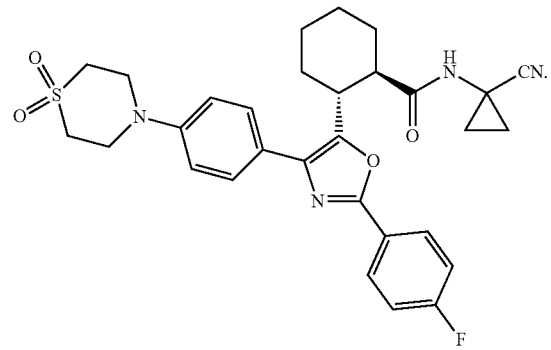 [SMILES: N#CC1(NC(=O)[C@@H]2CCCC[C@H]2c2oc(-c3ccc(F)cc3)nc2-c2ccc(N3CCS(=O)(=O)CC3)cc2)CC1]

* * * * *